United States Patent
Bakaletz

(10) Patent No.: US 10,722,568 B2
(45) Date of Patent: Jul. 28, 2020

(54) **TRANSCUTANEOUS *HAEMOPHILIUS INFLUENZAE* VACCINE FORMULATIONS AND METHODS**

(71) Applicant: RESEARCH INSTITUTE AT NATIONWIDE CHILDREN'S HOSPITAL, Columbus, OH (US)

(72) Inventor: Lauren O. Bakaletz, Hilliard, OH (US)

(73) Assignee: RESEARCH INSTITUTE AT NATIONWIDE CHILDREN'S HOSPITAL, Columbus, OH (US)

( * ) Notice: Subject to any disclaimer, the term of this patent is extended or adjusted under 35 U.S.C. 154(b) by 0 days.

(21) Appl. No.: 15/824,387

(22) Filed: Nov. 28, 2017

(65) Prior Publication Data

US 2018/0071381 A1    Mar. 15, 2018

Related U.S. Application Data

(62) Division of application No. 14/773,556, filed as application No. PCT/US2014/022871 on Mar. 10, 2014, now Pat. No. 9,855,326.

(60) Provisional application No. 61/775,132, filed on Mar. 8, 2013.

(51) Int. Cl.
| | |
|---|---|
| *A61K 39/102* | (2006.01) |
| *A61K 9/00* | (2006.01) |
| *A61K 9/70* | (2006.01) |
| *A61K 39/00* | (2006.01) |
| *A61K 39/385* | (2006.01) |

(52) U.S. Cl.
CPC .......... *A61K 39/102* (2013.01); *A61K 9/0014* (2013.01); *A61K 9/7084* (2013.01); *A61K 39/385* (2013.01); *A61K 2039/54* (2013.01); *A61K 2039/541* (2013.01); *A61K 2039/545* (2013.01); *A61K 2039/55544* (2013.01); *A61K 2039/60* (2013.01); *A61K 2039/6068* (2013.01)

(58) Field of Classification Search
CPC .......... A61K 2039/54; A61K 2039/541; A61K 2039/545; A61K 2039/55544; A61K 2039/60; A61K 2039/2039; A61K 2039/6068; A61K 39/102; A61K 39/385; A61K 9/0014; A61K 9/7084
See application file for complete search history.

(56) References Cited

U.S. PATENT DOCUMENTS

| | | | |
|---|---|---|---|
| 5,766,608 A | 6/1998 | Kolattukudy et al. | |
| 5,843,464 A | 12/1998 | Bakaletz et al. | |
| 6,268,171 B1 | 7/2001 | Meyer et al. | |
| 6,506,581 B1 | 1/2003 | Fleischmann et al. | |
| 7,501,131 B2 | 3/2009 | Bakaletz et al. | |
| 7,893,237 B2 | 2/2011 | Bakaletz et al. | |
| 8,399,000 B2 | 3/2013 | Bakaletz et al. | |
| 9,309,294 B2 | 4/2016 | Bakaletz et al. | |
| 2004/0137004 A1* | 7/2004 | Glenn | A61K 9/7061 424/184.1 |
| 2004/0146534 A1* | 7/2004 | Glenn | A61K 9/0019 424/257.1 |
| 2004/0202670 A1 | 10/2004 | Apicella | |
| 2005/0232983 A1 | 10/2005 | Sandage | |
| 2006/0276483 A1 | 12/2006 | Surber et al. | |
| 2008/0311110 A1 | 12/2008 | Bakaletz et al. | |
| 2011/0182976 A1 | 7/2011 | Wu et al. | |
| 2011/0236306 A1 | 9/2011 | Goodman et al. | |
| 2013/0142803 A1 | 6/2013 | Bakaletz et al. | |
| 2016/0175424 A1 | 6/2016 | Bakaletz et al. | |

FOREIGN PATENT DOCUMENTS

| | | |
|---|---|---|
| WO | WO-1999/064067 A2 | 12/1999 |
| WO | WO-2005/063802 A2 | 7/2005 |
| WO | WO-2006/138527 A2 | 12/2006 |
| WO | WO-2011/075688 A1 | 6/2011 |
| WO | WO-2012/154121 A1 | 11/2012 |
| WO | WO-2013/160335 A2 | 10/2013 |

OTHER PUBLICATIONS

Anderson et al., Human serum activities against *Hemophilus influenzae*, Type B. *J. Clin. Invest.* 51: 31-8 (1972).

Bakaletz et al., Demonstration of type IV pilus expression and a twitching phenotype by *Haemophilus influenzae*. *Infect. Immun.* 73(3): 1635-43 (2005).

Bakaletz et al., Evidence for transduction of specific antibodies into the middle ear of parenterally immunized chinchillas after an upper respiratory infection with adenovirus. *Clin. Diag. Lab. Immunol.* 4(2): 223-5 (1997).

Bakaletz et al., Frequency of fimbriation of nontypable *Haemophilus influenzae* and its ability to adhere to chinchilla and human respiratory epithelium. *Infect. Immun.* 56(2): 331-5 (1988).

Bakaletz et al., Modeling adenovirus type 1-induced otitis media in the chinchilla: Effect on ciliary activity and fluid transport function of eustachian tube mucosal epithelium. *J. Infect. Dis.* 168: 865-72 (1993).

Bakaletz et al., Protection against development of otitis media induced by nontypeable Haemophilus influenzae by both active and passive immunization in a chinchilla model of virus-bacterium superinfection, *Infect. Immun.*, 67:2746-62 (1999).

(Continued)

*Primary Examiner* — Michael B. Pallay
(74) *Attorney, Agent, or Firm* — Marshall, Gerstein & Borun LLP

(57) ABSTRACT

Provided are topical delivery systems and methods for treating and/or preventing a disease or disorder in a subject, or for eliciting an immune response in a subject including applying, to at least a portion of the subject's post-auricular region, a topical delivery system including a therapeutically effective amount of a topical pharmaceutical composition comprising at least one active agent and a pharmaceutically acceptable carrier and/or adjuvant. The topical pharmaceutical composition can include a topical immunogenic composition. The topical delivery system can further include a flexible substrate in communication with the topical immunogenic composition. The subject can be a pediatric subject.

17 Claims, 6 Drawing Sheets

Specification includes a Sequence Listing.

(56) References Cited

OTHER PUBLICATIONS

Bakaletz et al., Relative immunogenicity and efficacy of two synthetic chimeric peptides of fimbrin as vaccinogens against nasopharyngeal colonization by nontypeable *Haemophilus infulenzae* in the chinchilla. Vaccine, 15(9): 955-61 (1997).
Baldwin et al., Effects of otitis media on child development. Am. J. OtoL 14: 601-4 (1993).
Bardy et al., Prokaryotic motility structures. *Microbiol.* 149: 295-304 (2003).
Barenkamp et al., Outer membrane protein and biotype analysis of pathogenic nontypable *Haemophilus influenzae. Infect. Immun.* 36(2): 535-40 (1982).
Berman et al., Theoretical cost effectiveness of management options for children with persisting middling ear effusions. Pediatrics. 93: 353-63 (1994).
Black et al., Efficacy, safety and immunogenicity of heptavalent pneumococcal conjugate vaccine in children. Ped. Infect. Dis. J. 19(3): 187-95 (2000).
Bright et al., The prevalence of tympanostomy tubes in children in the United States. Am. J. Public Health. 83: 1026-8 (1993).
Catlin et al., The type B capsulation locus of Haemophilus influenzae: Map location and size. J. Microbiol. 70: 411-22 (1972).
Cimons et al., Lurid reports obscure reality of strep A outbreaks. ASM News. 60: 527-30 (1994).
Clemans et al., Comparative analysis of Haemophilus influenzae hifA (philin) genes. Infect. Immun. 66(2): 656-63 (1998).
Coleman et al., Chemically defined media for growth of Haemophilus influenzae strains. J. Clin. Micro. 41: 4408-10 (2003).
Coleman et al., Molecular cloning, expression, and sequence of the Pilin gene from nontypeable Haemophilus influenzae M37. Infect. Immunity. 59: 1716-22 (1991).
Daines et al., Haemophilus influenzae Rd KW20 has virulence properties. J. Med. Microbiol. 52: 277-82 (2003).
Darzins et al., Molecular genetic analysis of type-4 pilus biogenesis and twitching motility using Pseudomonas aeruginosa as a model system—a review. Gene. 192: 109-15 (1997).
DeMaria, et al., Immunization with Outer Membrane Protein P6 from Nontypeable Haemophilus influenzae Induces Bactericidal Antibody and Affords Protection in the Chinchilla Model of Otitis Media. Infection and Immunity, 64(12): 5187-5192 (Dec. 1996).
Devereux et al., A comprehensive set of sequence analysis programs for the VAX. Nucl Acids. Res. 12(1): 387-395 (1984).
Dougherty et al., Identification of Haemophilus influenzae Rd transformation genes using cassette mutagenesis. Microbiology. 145: 401-9 (1999).
Doughty et al., The type 4 fimbrial subunit gene of Pasteurella multocida. Vet. Microbiol. 72: 79-90 (2000).
Ehrlich et al., Mucosal biofilm formation of middle-ear mucosa in the chinchilla model of otitis media. JAMA. 287: 1710-5 (2002).
Eskola et al., Efficacy of a pneumococcal conjugate vaccine against acute otitis media. N. Engl. J. Med. 344(6): 403-9 (2001).
Eskola et al., Potential of bacterial vaccines in the prevention of acute otitis media. Ped. Infect. Dis. J. 19(5): S72-8 (2000).
Fleischmann et al., Whole-genome random sequence and assembly of Haemophilus influenzae Rd. Science,269: 496-512 (1995).
Friedrich et al., Molecular analyses of the natural transformation machinery and identification of pilus structures in the extremely thermophilic bacterium Thermus termophilus strain HB27. Appl. Environ. Microbiol. 68: 745-55 (2002).
Friedrich et al., Pilin-like proteins in the extremely thermophilic bacterium Thermus thermophilus HB27: Implications in competence for natural transformation and links to type IV pilus biogenesis. Appl. Environ. Microbiol. 69: 3695-700 (2003).
Fussenegger et al., Tranformation competence and type-4 pilus biogenesis in Neisseria gonorrhoeae—a review. Gene. 192: 125-34 (1997).
Genbank Accession No. P45285, Peptide transport periplasmic protein sapA precursor, Sep. 13, 2005.

Genbank Accession No. U32837, Haemophilus /nfluenzae Rd KW20 section 152 of 163 of the complete genome, Jun. 2, 2004.
Giebink, Immunology: Promise of New Vaccines, Ped. Infect Dis. J., 13(11): 1064-1068 (1994).
Gilsdorf et al., Role of pili in Haemophilus influenzae adherence and colonization. Infect. lmmun. 65: 2997-3002 (1997).
Gilsdorf et al., Role of pili in Haemophilus influenzae adherence to, and internalization by, respiratory cells. Pediatr. Res. 39: 343-8 (1996).
Holmes, et al., Adherence of Non-Typeable Haemophilus influenzae Promotes Reorganization of the Actin Cytoskeleton in Human or Chinchilla Epithelial Cells in vitro, Microbial Pathogenesis, 23: 157-166 (1997).
Hunter et al., Identification of hearing loss in children with otitis media. Ann. Otol. Rhinol. Laryngol. Suppl. 163: 59-61 (1994).
Jansen et al., Immunotoxins: Hybrid molecules combining high specificity and potent cytotoxicity. Immun. Rev. 62: 185-216 (1982).
Jesaitis et al., Compromised host defence on Pseudomonas aeruginosa biofilms: Characterization of neutrophil and biofilm interactions. J. Immunol. 171: 4329-39 (2003).
Kaplan et al., Overall cost in the treatment of otitis media. Pediatr. Infect. Dis. J. 16: S9-1 1 (1997).
Karma et al., Immunological Aspects of Otitis Media: Present Views on Possibilities of Immunoprophylazis of Acute Otitis Media in Infants and Children, Int. J. Pediat. Otorhinolaryngology, 32 (Suppl.): S127-S134 (1995).
Karudapuram et al.,The Haemophilus influenzae dprABC genes constitute a competence-inducible operon that requires the product of the tfoX(sxy) gene for transcriptional activation. J. Bacteriology. 179(15): 4815-20 (1997).
Keizer et al., Structure of a pilin monomer from Pseudomonas aeruginosa. J. Biol. Chem. 276: 24186-93 (2001).
Kennedy et al., Passive transfer of antiserum specific for immunogens derived from a nontypeable Haemophilus influenzae adhesin and lipoprotein D prevents otitis media after heterologous challenge. Infect. Immun. 68(5): 2756-65 2000).
Klausen et al., Biofilm formation by Pseudomonas aeruginosa wild type, flagella and type IV pill mutants. Mol. Microbiol. 48: 1511-24 (2003).
Klausen et al., Involvement of bacterial migration in the development of complex multicellular structures in Pseudomonas aeruginosa biofilms. Mol. Microbiol. 50: 61-8 (2003).
Klein, Role of nontypeable Haemophilus influenzae in pediatric respiratory tract infections. Pedriatr. Infect. Dis. J. 16: S5-8 (1997).
Klein, The burden of otitis media. Vaccine, 19(Suppl. 1): S2-8 (2001).
Kyd et al., Potential of a novel protein, OMP26, from nontypeable Haemophilus influenzae to enhance pulmonary clearance in a rat model. Infect. Immun. 66: 2272-8 (1998).
Lopez-Solanilla et al., Inactivation of the sapA to sapF locus of Erwinia chrysanthemi reveals common features in plant and animal bacterial pathogenesis. Plant Cell, 10: 917-24 (1998).
Mason et al., Nontypeable Haemophilus influenzae gene expression induced in vivo in a chinchilla model of otitis media. Infect. Immunol. 71: 3454-62 (2003).
Matteucci et al., Synthesis of deoxyoligonucleotides on a polymer support. J. Am. Chem. Soc. 103: 3185 (1981).
Mattick, Type IV pili and twitching motility. Annu. Rev. Microbiol. 56: 289-314 (2002).
McCoy et al., Identification of Proteas mirabilis with Increased Sensitivity AntiMicrobial Peptides. Antimicrob. Agents Chemother. 45(7): 2030-7 (2001).
Merz et al., Pilus retraction powers bacterial twitching motility. Nature, 407: 98-102 (2000).
Mhlanga-Mutangadura et al., Evolution of the major pilus gene cluster of Haemophilus influenzae. J. Bacteriol. 180(17): 4693-703 (1998).
Mudannayake et al., Whole genome analysis of gene expression changes during competence development in Haemophilus influenzae. Abstracts of the General Meeting of the American Society for Microbiology. 103: D-001 (2003).

(56) References Cited

OTHER PUBLICATIONS

Musser et al., Genetic relationships of serologically nontypable and serotype b strains of Haemophilus influenzae. Infect. Immun. 52(1): 183-91 (1986).
Novotny et al., Epitope mapping of the outer membrane protein P5-homologous fimbrin adhesin of nontypeable Haemophilus influenzae. InfectImmun. 68(4): 2119-28 (2000).
Novotny et al., The fourth surface-exposed region of the outer membrane protein P5-homologous adhesion of nontypable Haemophilus influenzae is an immunodominant but nonprotective decoying epitope. J. Immunol. 171: 1978-83 (2003).
O'Toole et al., Flagellar and twitching motility are necessary for Pseudomonas aeruginosa biofilm development. Mol. Microbiol. 30: 295-304 (1998).
Paap, Management of otitis media with effusion in young children. Ann. Pharmacother. 30(11): 1291-7 (1996).
Parra-Lopez et al., A *salmonella* protein that is required for resistance to antimicrobial peptides and transport of potassium. EMBO J. 13(17): 3964-72 (1994).
Parra-Lopez et al., Molecular genetic analysis of a locus required for resistance to antimicrobial peptides in *Salmonella* typhimurium. EMBO J. 12(11): 4053-4062 (1993).
Perez-Casal et al., Mry, a trans-acting positive regulator of the M protein gene of *Streptococcus pyogenes* with similarity to the receptor proteins of two-component regulatory systems. J. Bacteriol. 173: 2617-24 (1991).
Poje et al., Haemophilus Influenzae Protocols, Transformation of Haemophilus influenzae, Humana Press Inc., Toronto, pp. 57-70 (2003).
Poolman et al., Developing a nontypeable Haemophilus influenzae (NTHi) vaccine. Vaccine, 19: S108-15 (2001).
Risberg et al., Structural analysis of the lipopolysaccharide oligosaccharide epitopes expressed by a capsule-deficient strain of Haemophilus influenzae Rd. Eur. J. Biochem. 261: 171-80 (1999).
Ruffolo et al., Identification, purification, and characterization of the type 4 fimbriae of Pasteurella multocida. Infect. Immun. 65: 339-43 (1997).
Semmler et al., A re-examination of twitching motility in Pseudomonas aeruginosa. Microbiology. 145: 2863-73 (1999).
Skerker et al., Direct observation of extension and retraction of type IV pili. Proc. Natl. Acad. Sci. USA. 98: 6901-4 (2001).
Snow, Progress in the prevention of otitis media through immunization. Otology & Neurotology, 23(1): 1-2 (2002).
Spinola et al., Epidemiology of colonization by nontypable Haemophilus influenzae in children: A longitudinal study. J. Infect. Dis. 154(1): 100-9 (1986).

St. Geme III, Molecular and cellular determinants of non-typeable Haemophilus influenzae adherence and invasion. Cell Microbiol. 4: 191-200 (2002).
Stevenson et al., Cloning and characterisation of type 4 fimbrial genes from Actinobacillus pleuropneumoniae. Vet. Microbiol. 92:121-34 (2003).
Strom, Structure-function and biogenesis of the type IV pili. Annu. Rev. Microbiol. 47: 565-96 (1993).
Suzuki et al., Synergistic effect of adenovirus type 1 and nontypeable Haemophilus influenzae in a chinchilla model of experimental otitis media. Infect. Immun. 62(5): 1710-8 (1994).
Swiss Prot Accession No. P31768, dated Jul. 1, 1993.
Swiss Prot Accession No. P31769, dated Jul. 1, 1993.
Swiss Prot Accession No. P31770, dated Jul. 1, 1993.
Swiss Prot Accession No. P31771, dated Jul. 1, 1993.
Swiss Prot Accession No. P31772, dated Jul. 1, 1993.
Swiss Prot Accession No. P31773, dated Jul. 1, 1993.
Teele et al., Otitis media in infancy and intellectual ability, school achievement, speech, and language at age 7 years. J. Infect. Dis. 162: 685-94 (1990).
Tonjum et al., The pilus colonization factor of pathogenic neisserial species : organelle biogenesis and structure/function relationships—a review. Gene, 192: 155-63 (1997).
UniProt Database Accession No. Q5D8E3_HAEIN, PilA, Haemophilus influenzae, dated Mar. 29, 2005.
Wall et al., Type IV pill and cell motility. MoL Microbiol. 32:1-10 (1999).
Watson et al., Identification of a gene, pilF, required for type 4 fimbrial biogenesis and twitching motility in Pseudomonas aeruginosa. Gene, 180: 49-56 (1996).
Wolfgang et al., Components and dynamics of fiber formation define a ubiquitous biogenesis pathway for bacterial pill. EMBO J. 19: 6408-18 (2000).
Zhang et al., Identification of type 4 fimbriae in Actinobacillus pleuropneumoniae. FEMS Microbiol Lett. 189: 15-8 (2000).
Zwahlen et al., Participation of complement in host defense against cCapsule-deficient Haemophilus influenzae. Infect. Immun. 42: 708-15 (1983).
International Preliminary Report on Patentability, PCT/US2014/022871, dated Sep. 8, 2015.
International Search Report and Written Opinion of the International Search Authority, United States Patent Office, PCT/US2014/022871, dated Aug. 15, 2014.
International Search Report, European Patent Office, PCT/US2006/026183, dated Dec. 27, 2006.
Novotny et al., Therapeutic Transcutaneous Immunization with a Band-Aid Vaccine Resolves Experimental Otitis Media, *Clin. Vac. Immunol.*, 22(8):867 (2015).

\* cited by examiner

SEQUENCE LISTING

```
<160> NUMBER OF SEQ ID NOS: 57

<210> SEQ ID NO 1
<211> LENGTH: 4345
<212> TYPE: DNA
<213> ORGANISM: H. influenzae
<220> FEATURE:
<221> NAME/KEY: CDS
<222> LOCATION: (403)..(849)

<400> SEQUENCE: 1
gcgatcatta  aaattgacat  attgcgtaat  tcgcccattt  cgttcgatca  aacaatgtgc        60
tgaaacacgc  atttgataaa  tttctgcaaa  ataaggatga  atcttaggat  ctaattttcc       120
ttgaaaaaaa  tcatccacat  atccgccgcc  aaattgttct  ggcggcagac  taatataatg       180
aataaccaat  aaggaaatat  cctgtggatt  tgggcgttta  tcgaagtgag  gtgactgaat       240
ttgccgacaa  tccaatatac  cttgttcaat  atcttttagt  ttttgcatac  ttttttcctt       300
tttttgcgat  caggatcgca  gaaaaagtgc  ggtcaatttt  acaaacaaat  ttttcctttt       360
cacaatgtcg  tcgctaacaa  aggcttaata  aaaggaaaat  ga atg aaa cta aca            414
                                              Met Lys Leu Thr
                                                1 aca cag caa acc ttg aaa aaa ggg ttt aca tta ata gag cta atg att   462
Thr Gln Gln Thr Leu Lys Lys Gly Phe Thr Leu Ile Glu Leu Met Ile
 5                  10                  15                  20 gtg att gca att att gct att tta gcc act atc gca att ccc tct tat   510
Val Ile Ala Ile Ile Ala Ile Leu Ala Thr Ile Ala Ile Pro Ser Tyr
                 25                  30                  35 caa aat tat act aaa aaa gca gcg gta tct gaa tta ctg caa gcg tca   558
Gln Asn Tyr Thr Lys Lys Ala Ala Val Ser Glu Leu Leu Gln Ala Ser
             40                  45                  50 gcg cct tat aag gct gat gtg gaa tta tgt gta tat agc aca aat gaa   606
Ala Pro Tyr Lys Ala Asp Val Glu Leu Cys Val Tyr Ser Thr Asn Glu
         55                  60                  65 aca aca aac tgt acg ggt gga aaa aat ggt att gca gca gat ata acc   654
Thr Thr Asn Cys Thr Gly Gly Lys Asn Gly Ile Ala Ala Asp Ile Thr
     70                  75                  80
```

| | | |
|---|---|---|
| aca gca aaa ggc tat gta aaa tca gtg aca aca agc aac ggt gca ata<br>Thr Ala Lys Gly Tyr Val Lys Ser Val Thr Thr Ser Asn Gly Ala Ile<br>85                     90                    95                  100 | | 702 |
| aca gta aaa ggg gat ggc aca ttg gca aat atg gaa tat att ttg caa<br>Thr Val Lys Gly Asp Gly Thr Leu Ala Asn Met Glu Tyr Ile Leu Gln<br>                 105                   110                    115 | | 750 |
| gct aca ggt aat gct gca aca ggt gta act tgg aca aca act tgc aaa<br>Ala Thr Gly Asn Ala Ala Thr Gly Val Thr Trp Thr Thr Thr Cys Lys<br>           120                    125                    130 | | 798 |
| gga acg gat gcc tct tta ttt cca gca aat ttt tgc gga agt gtc aca<br>Gly Thr Asp Ala Ser Leu Phe Pro Ala Asn Phe Cys Gly Ser Val Thr<br>          135                    140                    145 | | 846 |
| caa tgacgagcta tgctttactt catactcagc gtgtaaccgc tcaaaatggc<br>Gln | | 899 |
| gagatcttta cgatctcgcc agattttatgg gaacgcaatc agcagcaaca atccttgctc | | 959 |
| ttgcggtatt ttgctttgcc acttaaagaa gaaaataatc gtctttggct aggggttgat | | 1019 |
| tctctctcca atctttcagc ttgtgaaacc attgcgttta acaggaaaa acctgtcgaa | | 1079 |
| ccaattttgt tagaaagcag ccaactcaaa gaactgttac aacaacttac tccgcaccaa | | 1139 |
| atgcaagtgg aagagcaagt taaattctat caacatcaag aaacccattt tgaacaagaa | | 1199 |
| gatgatgaac ctgttatccg cttacttaat cagattttg aatctgcctt acaaaaaaat | | 1259 |
| gcctctgata ttcatttaga aaccttggct gatcagtttc aagtgcggtt tagaattgat | | 1319 |
| ggtgttttac aaccacaacc cttaataagc aaaatattcg ccaatcgtat tatttcacgc | | 1379 |
| ttaaaattac tggctaaatt agatattagt gaaaatcgac ttccacaaga tggacgattt | | 1439 |
| caatttaaaa ccactttttc cgatattctt gattttcgcc tttcaacctt accaacccat | | 1499 |
| tggggcgaaa aaatcgtgtt gcgagcgcaa caaaataaac ctgtagaact agctttgct | | 1559 |
| gaactgggta tgaccgaaaa tcagcaacaa gcatttcaac gctcacttag ccagccacaa | | 1619 |
| ggattaattt tagtaaccgg ccccacagga agtgggaaaa gtatctcgct ttacaccgca | | 1679 |
| cttcagtggc taaatacgcc tgataaacat attatgaccg ctgaagatcc cattgaaatt | | 1739 |
| gaacttgatg gtattattca aagccaaatt aatccgcaga ttggattaga ttttagccgt | | 1799 |
| ctattgcgtg ctttttacg tcaagatccc gacatcatta tgctaggtga aattcgagat | | 1859 |
| gaagaaagtg caaggattgc actacgtgcc gctcaaacgg gacatttggt gctttcaact | | 1919 |
| ttacatacca atgatgcaat atctgccatt tctcgcttac aacaactcgg tattcaacaa | | 1979 |
| catgaaattg aaaacagttt actactcgtc attgcacagc gtcttgtacg aaaaatctgt | | 2039 |
| ccaaagtgcg gtgaaattt aataaattct tgtgattgcc atcaaggtta tcgagggcga | | 2099 |
| atcggcgtgt atcaatttct acattggcaa cagaatggct atcaaacgga ttttgagaat | | 2159 |
| ttacgagaga gtggtttgga aaagttagc caaggcataa cagatgagaa agaaattgaa | | 2219 |
| cgtgtgttag gtaaaaactc atgactaaaa aactcttta ttatcaaggt agtaacgcat | | 2279 |
| taaatcagaa acaaaaggc tcaattattg cggatacgaa acaacaagcg cactttcagt | | 2339 |
| taataagccg cgggcttact cacatcaaat acaacaaaa ctggcaattt ggggcaaaac | | 2399 |
| ccaaaaattc agaaatcagt gaattactca atcaattagc gacattgcta cagtccgtaa | | 2459 |
| ttccgttaaa aaacagccta caaattttgc aacaaaattg tactcaaatt atgctcaaca | | 2519 |
| aatggcttga acgactgctt caatccattg aatctggctt agcattctca caagccattg | | 2579 |
| aacaacaagg aaaatatctc acacaacaag aaattcaact gattcaagtg ggagaaatga | | 2639 |
| caggaaaact tgccgtagtt tgtaaaaaaa tagccacgca ccgtagtcaa tctttggctt | | 2699 |

-continued

```
tacaacgcaa attacagaaa attatgttat atccctcaat ggtattggga atttctctat    2759
tattgacact cgcattactg ctttttatcg cgcctcaatt tgctgaaatg tacagtggca    2819
ataatgcgga gttaccaaca ataaccgcaa tattgctctc aatatctaat ttccttaagc    2879
aaaatattgg cattttgcta ttttttcgtt tgagttttttt tctattttat tatttctatc    2939
taaaacgcca gacttggttt catcaaaaga aaaatcaact tatttctatc acgcctattt    2999
ttggcacaat tcaaaagctt tcacgtttag tgaactttag tcaaagttta caaattatgt    3059
tgcaggccgg cgtaccgctt aatcaggcac tagacagttt tcttcctcgc acacaaactt    3119
ggcaaaccaa gaaaacgctt gtaaacgata tggtattaga taaagaagtg cggtcaattt    3179
tgcaatgggt ttctcaaggc tatgcgtttt ctaatagcgt aagtagcgat cttttcccga    3239
tggaagcaca acaaatgcta caaattggcg aacaaagcgg aaaactcgct ttgatgctag    3299
agcatatcgc agataattac caagaaaaac ttaatcatca aattgactta ctctcacaaa    3359
tgctagaacc attaatgatg gtaatcatcg gcagtctgat tgggattatt atgatgggaa    3419
tgtatttacc tatctttaat atgggatcag ttattcaatg atttacttca caatgttttt    3479
attaggcggc atcttaggga tcgcattgtg gttctaccta tctggtttta ttacgcatt    3539 gcagcaagag atttatgcga cttacgttga attatttcca caaaacagtt ctccatttca    3599
accgcacttt gcctctattc aacaaaaaaa gtgcggtcat attttgaggt attttttttag    3659 tattggggtt ggattatat ttttacaaat tgccttcaaa gattctattt ttactgtatg    3719
gatcggactc acacttatta ttctttggac aatcagttat cttgattggc actatcaact    3779
tatttctacg acaccctgtt tatggttact tactctcggt ttatttggcg cagacaataa    3839
cttttcattg ctaacgttat ctgaaagcat aaaaagtgcg gctagttttt ttattgtttt    3899
ctacgcaatc tattggattg caaaatgtta ttatagaaaa gaagcctttg gacggggaga    3959
ttattggcta gcaatggcat taggaagttt tattcattta gaaaccttac cgcactttt    4019 attattagcc tcagtgcttg gaatatgttt ttcgcttatt cataaaaaga aaaaagaatt    4079 tataccttt gcccctttta tgaacttatc ggctatcatt atttatctcg tcaaatatta    4139
cggatattaa aaaggggaaa acataatatt tttcccttgt tcttcataga agtgcggttg    4199
tttttacgaa cgtttcatca cttcaaaaaa ctcttcgttg gttttcgcca tcatcagctt    4259
atcaatcaag aattccattg catccacttc atccattgga ttaagaatct tacgaagaat    4319
ccacattttt tgtaattcgt ccgctg                                         4345
```

<210> SEQ ID NO 2
<211> LENGTH: 149
<212> TYPE: PRT
<213> ORGANISM: H. influenzae

<400> SEQUENCE: 2

```
Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
65                  70                  75                  80
```

```
Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 3
<211> LENGTH: 131
<212> TYPE: PRT
<213> ORGANISM: H. influenzae

<400> SEQUENCE: 3

Met Gly Ser Ser His His His His His His Ser Gly Leu Val Pro
1               5                   10                  15

Arg Gly Ser His Met Thr Lys Lys Ala Ala Val Ser Glu Leu Leu Gln
            20                  25                  30

Ala Ser Ala Pro Tyr Lys Ala Asp Val Glu Leu Cys Val Tyr Ser Thr
        35                  40                  45

Asn Glu Thr Thr Asn Cys Thr Gly Gly Lys Asn Gly Ile Ala Ala Asp
    50                  55                  60

Ile Thr Thr Ala Lys Gly Tyr Val Lys Ser Val Thr Thr Ser Asn Gly
65                  70                  75                  80

Ala Ile Thr Val Lys Gly Asp Gly Thr Leu Ala Asn Met Glu Tyr Ile
                85                  90                  95

Leu Gln Ala Thr Gly Asn Ala Ala Thr Gly Val Thr Trp Thr Thr Thr
            100                 105                 110

Cys Lys Gly Thr Asp Ala Ser Leu Phe Pro Ala Asn Phe Cys Gly Ser
        115                 120                 125

Val Thr Gln
    130

<210> SEQ ID NO 4
<211> LENGTH: 19
<212> TYPE: PRT
<213> ORGANISM: Artificial sequence
<220> FEATURE:
<223> OTHER INFORMATION: Synthetic Peptide

<400> SEQUENCE: 4

Arg Ser Asp Tyr Lys Phe Tyr Glu Asp Ala Asn Gly Thr Arg Asp His
1               5                   10                  15

Lys Lys Gly

<210> SEQ ID NO 5
<211> LENGTH: 24
<212> TYPE: PRT
<213> ORGANISM: Artificial sequence
<220> FEATURE:
<223> OTHER INFORMATION: Synthetic Peptide

<400> SEQUENCE: 5

Leu Val Arg Ser Asp Tyr Lys Phe Tyr Glu Asp Ala Asn Gly Thr Arg
1               5                   10                  15

Asp His Lys Lys Gly Arg His Thr
```

20

<210> SEQ ID NO 6
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 6

Arg Ser Asp Tyr Lys Leu Tyr Asn Lys Asn Ser Ser Asn Ser Thr
1               5                   10                  15

Leu Lys Asn Leu Gly Glu
            20

<210> SEQ ID NO 7
<211> LENGTH: 19
<212> TYPE: PRT
<213> ORGANISM: Artificial sequence
<220> FEATURE:
<223> OTHER INFORMATION: Synthetic Peptide

<400> SEQUENCE: 7

Arg Ser Asp Tyr Lys Leu Tyr Asn Lys Asn Ser Ser Thr Leu Lys Asp
1               5                   10                  15

Leu Gly Glu

<210> SEQ ID NO 8
<211> LENGTH: 13
<212> TYPE: PRT
<213> ORGANISM: Artificial sequence
<220> FEATURE:
<223> OTHER INFORMATION: Synthetic Peptide

<400> SEQUENCE: 8

Arg Ser Asp Tyr Lys Phe Tyr Asp Asn Lys Arg Ile Asp
1               5                   10

<210> SEQ ID NO 9
<211> LENGTH: 139
<212> TYPE: PRT
<213> ORGANISM: Artificial sequence
<220> FEATURE:
<223> OTHER INFORMATION: Chimeric protein

<400> SEQUENCE: 9

Met Gly Ser Ser His His His His Ser Ser Gly Leu Val Pro Arg
1               5                   10                  15

Gly Ser His Met Thr Lys Lys Ala Ala Val Ser Glu Leu Leu Gln Ala
            20                  25                  30

Ser Ala Pro Tyr Lys Ala Asp Val Glu Leu Cys Arg Ser Asp Tyr Lys
        35                  40                  45

Phe Tyr Glu Asp Ala Asn Gly Thr Arg Asp His Lys Lys Gly Cys Thr
    50                  55                  60

Gly Gly Lys Asn Gly Ile Ala Ala Asp Ile Thr Thr Ala Lys Gly Tyr
65                  70                  75                  80

Val Lys Ser Val Thr Thr Ser Asn Gly Ala Ile Thr Val Lys Gly Asp
                85                  90                  95

Gly Thr Leu Ala Asn Met Glu Tyr Ile Leu Gln Ala Thr Gly Asn Ala
            100                 105                 110

Ala Thr Gly Val Thr Trp Thr Thr Cys Lys Gly Thr Asp Ala Ser Leu
        115                 120                 125

Phe Pro Ala Asn Phe Cys Gly Ser Val Thr Gln
    130                 135

<210> SEQ ID NO 10
<211> LENGTH: 143
<212> TYPE: PRT
<213> ORGANISM: Artificial sequence
<220> FEATURE:
<223> OTHER INFORMATION: Chimeric Protein

<400> SEQUENCE: 10

Met Gly Ser Ser His His His His Ser Ser Gly Leu Val Pro Arg
1               5                   10                  15

Gly Ser His Met Thr Lys Lys Ala Ala Val Ser Glu Leu Leu Gln Ala
                20              25                  30

Ser Ala Pro Tyr Lys Ala Asp Val Glu Leu Cys Leu Val Arg Ser Asp
            35                  40                  45

Tyr Lys Phe Tyr Glu Asp Ala Asn Gly Thr Arg Asp His Lys Lys Gly
    50                  55                  60

His Thr Cys Thr Gly Gly Lys Asn Gly Ile Ala Ala Asp Ile Thr Thr
65                  70                  75                  80

Ala Lys Gly Tyr Val Lys Ser Val Thr Ser Asn Gly Ala Ile Thr
                85                  90                  95

Val Lys Gly Asp Gly Thr Leu Ala Asn Met Glu Tyr Ile Leu Gln Ala
                100                 105                 110

Thr Gly Asn Ala Ala Thr Gly Val Thr Trp Thr Thr Cys Lys Gly Thr
            115                 120                 125

Asp Ala Ser Leu Phe Pro Ala Asn Phe Cys Gly Ser Val Thr Gln
    130                 135                 140

<210> SEQ ID NO 11
<211> LENGTH: 136
<212> TYPE: PRT
<213> ORGANISM: Artificial sequence
<220> FEATURE:
<223> OTHER INFORMATION: Chimeric Protein

<400> SEQUENCE: 11

Met Gly Ser Ser His His His His Ser Ser Gly Leu Val Pro Arg
1               5                   10                  15

Gly Ser His Met Thr Lys Lys Ala Ala Val Ser Glu Leu Leu Gln Ala
                20              25                  30

Ser Ala Pro Tyr Lys Ala Asp Val Glu Leu Cys Val Thr Ser Thr Asn
            35                  40                  45

Glu Thr Thr Asn Cys Thr Gly Gly Lys Asn Gly Ile Ala Ala Asp Ile
    50                  55                  60

Thr Thr Ala Lys Gly Tyr Val Lys Ser Val Thr Ser Asn Gly Ala
65                  70                  75                  80

Ile Thr Val Lys Gly Asp Gly Thr Leu Ala Asn Met Glu Tyr Ile Leu
                85                  90                  95

Gln Ala Thr Gly Asn Ala Ala Thr Gly Val Thr Trp Thr Thr Cys Arg
                100                 105                 110

Ser Asp Tyr Lys Phe Tyr Glu Asp Ala Asn Gly Thr Arg Asp His Lys
            115                 120                 125

Lys Gly Cys Gly Ser Val Thr Gln
    130                 135

<210> SEQ ID NO 12
<211> LENGTH: 141
<212> TYPE: PRT
<213> ORGANISM: Artificial sequence
<220> FEATURE:
<223> OTHER INFORMATION: Chimeric Protein

<400> SEQUENCE: 12

```
Met Gly Ser Ser His His His His Ser Ser Gly Leu Val Pro Arg
1               5                   10                  15

Gly Ser His Met Thr Lys Lys Ala Ala Val Ser Glu Leu Leu Gln Ala
            20                  25                  30

Ser Ala Pro Tyr Lys Ala Asp Val Glu Leu Cys Val Thr Ser Thr Asn
        35                  40                  45

Glu Thr Thr Asn Cys Thr Gly Gly Lys Asn Gly Ile Ala Ala Asp Ile
    50                  55                  60

Thr Thr Ala Lys Gly Tyr Val Lys Ser Val Thr Ser Asn Gly Ala
65                  70                  75                  80

Ile Thr Val Lys Gly Asp Gly Thr Leu Ala Asn Met Glu Tyr Ile Leu
                85                  90                  95

Gln Ala Thr Gly Asn Ala Ala Thr Gly Val Thr Trp Thr Thr Cys Leu
            100                 105                 110

Val Arg Ser Asp Tyr Lys Phe Tyr Glu Asp Ala Asn Gly Thr Arg Asp
        115                 120                 125

His Lys Lys Gly Arg His Thr Cys Gly Ser Val Thr Gln
    130                 135                 140
```

<210> SEQ ID NO 13
<211> LENGTH: 148
<212> TYPE: PRT
<213> ORGANISM: Artificial sequence
<220> FEATURE:
<223> OTHER INFORMATION: Chimeric Protein

<400> SEQUENCE: 13

```
Met Gly Ser Ser His His His His Ser Ser Gly Leu Val Pro Arg
1               5                   10                  15

Gly Ser His Met Thr Lys Lys Ala Ala Val Ser Glu Leu Leu Gln Ala
            20                  25                  30

Ser Ala Pro Tyr Lys Ala Asp Val Glu Leu Cys Val Thr Ser Thr Asn
        35                  40                  45

Glu Thr Thr Asn Cys Thr Gly Gly Lys Asn Gly Ile Ala Ala Asp Ile
    50                  55                  60

Thr Thr Ala Lys Gly Tyr Val Lys Ser Val Thr Ser Asn Gly Ala
65                  70                  75                  80

Ile Thr Val Lys Gly Asp Gly Thr Leu Ala Asn Met Glu Tyr Ile Leu
                85                  90                  95

Gln Ala Thr Gly Asn Ala Ala Thr Gly Val Thr Trp Thr Thr Cys Lys
            100                 105                 110

Gly Thr Asp Ala Ser Leu Phe Pro Ala Asn Phe Cys Gly Ser Val Thr
        115                 120                 125

Gln Arg Ser Asp Tyr Lys Phe Tyr Glu Asp Ala Asn Gly Thr Arg Asp
    130                 135                 140

His Lys Lys Gly
145
```

<210> SEQ ID NO 14
<211> LENGTH: 153

```
<212> TYPE: PRT
<213> ORGANISM: Artificial sequence
<220> FEATURE:
<223> OTHER INFORMATION: Chimeric Protein

<400> SEQUENCE: 14

Met Gly Ser Ser His His His His His Ser Gly Leu Val Pro Arg
1               5                   10                  15

Gly Ser His Met Thr Lys Lys Ala Ala Val Ser Glu Leu Leu Gln Ala
            20                  25                  30

Ser Ala Pro Tyr Lys Ala Asp Val Glu Leu Cys Val Thr Ser Thr Asn
            35                  40                  45

Glu Thr Thr Asn Cys Thr Gly Gly Lys Asn Gly Ile Ala Ala Asp Ile
50                  55                  60

Thr Thr Ala Lys Gly Tyr Val Lys Ser Val Thr Thr Ser Asn Gly Ala
65                  70                  75                  80

Ile Thr Val Lys Gly Asp Gly Thr Leu Ala Asn Met Glu Tyr Ile Leu
                85                  90                  95

Gln Ala Thr Gly Asn Ala Ala Thr Gly Val Thr Trp Thr Thr Cys Lys
            100                 105                 110

Gly Thr Asp Ala Ser Leu Phe Pro Ala Asn Phe Cys Gly Ser Val Thr
            115                 120                 125

Gln Leu Val Arg Ser Asp Tyr Lys Phe Tyr Glu Asp Ala Asn Gly Thr
130                 135                 140

Arg Asp His Lys Lys Gly Arg His Thr
145                 150

<210> SEQ ID NO 15
<211> LENGTH: 142
<212> TYPE: PRT
<213> ORGANISM: Artificial sequence
<220> FEATURE:
<223> OTHER INFORMATION: Chimeric Protein

<400> SEQUENCE: 15

Met Gly Ser Ser His His His His His Ser Gly Leu Val Pro Arg
1               5                   10                  15

Gly Ser His Met Thr Lys Lys Ala Ala Val Ser Glu Leu Leu Gln Ala
            20                  25                  30

Ser Ala Pro Tyr Lys Ala Asp Val Glu Leu Cys Arg Ser Asp Tyr Lys
            35                  40                  45

Leu Tyr Asn Lys Asn Ser Ser Ser Asn Ser Thr Leu Lys Asn Leu Gly
50                  55                  60

Glu Cys Thr Gly Gly Lys Asn Gly Ile Ala Ala Asp Ile Thr Thr Ala
65                  70                  75                  80

Lys Gly Tyr Val Lys Ser Val Thr Thr Ser Asn Gly Ala Ile Thr Val
                85                  90                  95

Lys Gly Asp Gly Thr Leu Ala Asn Met Glu Tyr Ile Leu Gln Ala Thr
            100                 105                 110

Gly Asn Ala Ala Thr Gly Val Thr Trp Thr Thr Cys Lys Gly Thr Asp
            115                 120                 125

Ala Ser Leu Phe Pro Ala Asn Phe Cys Gly Ser Val Thr Gln
130                 135                 140

<210> SEQ ID NO 16
<211> LENGTH: 147
<212> TYPE: PRT
<213> ORGANISM: Artificial sequence
```

<220> FEATURE:
<223> OTHER INFORMATION: Chimeric Protein

<400> SEQUENCE: 16

```
Met Gly Ser Ser His His His His Ser Gly Leu Val Pro Arg
1               5                   10                  15

Gly Ser His Met Thr Lys Lys Ala Ala Val Ser Glu Leu Leu Gln Ala
            20                  25                  30

Ser Ala Pro Tyr Lys Ala Asp Val Glu Leu Cys Leu Val Arg Ser Asp
        35                  40                  45

Tyr Lys Leu Tyr Asn Lys Asn Ser Ser Ser Asn Ser Thr Leu Lys Asn
    50                  55                  60

Leu Gly Glu Arg His Thr Cys Thr Gly Gly Lys Asn Gly Ile Ala Ala
65                  70                  75                  80

Asp Ile Thr Thr Ala Lys Gly Tyr Val Lys Ser Val Thr Ser Asn
                85                  90                  95

Gly Ala Ile Thr Val Lys Gly Asp Gly Thr Leu Ala Asn Met Glu Tyr
                100                 105                 110

Ile Leu Gln Ala Thr Gly Asn Ala Ala Thr Gly Val Thr Trp Thr Thr
                115                 120                 125

Cys Lys Gly Thr Asp Ala Ser Leu Phe Pro Ala Asn Phe Cys Gly Ser
130                 135                 140

Val Thr Gln
145
```

<210> SEQ ID NO 17
<211> LENGTH: 139
<212> TYPE: PRT
<213> ORGANISM: Artificial sequence
<220> FEATURE:
<223> OTHER INFORMATION: Chimeric Protein

<400> SEQUENCE: 17

```
Met Gly Ser Ser His His His His Ser Gly Leu Val Pro Arg
1               5                   10                  15

Gly Ser His Met Thr Lys Lys Ala Ala Val Ser Glu Leu Leu Gln Ala
            20                  25                  30

Ser Ala Pro Tyr Lys Ala Asp Val Glu Leu Cys Val Thr Ser Thr Asn
        35                  40                  45

Glu Thr Thr Asn Cys Thr Gly Gly Lys Asn Gly Ile Ala Ala Asp Ile
    50                  55                  60

Thr Thr Ala Lys Gly Tyr Val Lys Ser Val Thr Thr Ser Asn Gly Ala
65                  70                  75                  80

Ile Thr Val Lys Gly Asp Gly Thr Leu Ala Asn Met Glu Tyr Ile Leu
                85                  90                  95

Gln Ala Thr Gly Asn Ala Ala Thr Gly Val Thr Trp Thr Thr Cys Arg
                100                 105                 110

Ser Asp Tyr Lys Leu Tyr Asn Lys Asn Ser Ser Ser Asn Ser Thr Leu
                115                 120                 125

Lys Asn Leu Gly Glu Cys Gly Ser Val Thr Gln
130                 135
```

<210> SEQ ID NO 18
<211> LENGTH: 144
<212> TYPE: PRT
<213> ORGANISM: Artificial sequence
<220> FEATURE:
<223> OTHER INFORMATION: Chimeric Protein

<400> SEQUENCE: 18

Met Gly Ser Ser His His His His Ser Gly Leu Val Pro Arg
1               5                   10                  15

Gly Ser His Met Thr Lys Lys Ala Ala Val Ser Glu Leu Leu Gln Ala
            20                  25                  30

Ser Ala Pro Tyr Lys Ala Asp Val Glu Leu Cys Val Thr Ser Thr Asn
        35                  40                  45

Glu Thr Thr Asn Cys Thr Gly Gly Lys Asn Gly Ile Ala Ala Asp Ile
    50                  55                  60

Thr Thr Ala Lys Gly Tyr Val Lys Ser Val Thr Thr Ser Asn Gly Ala
65                  70                  75                  80

Ile Thr Val Lys Gly Asp Gly Thr Leu Ala Asn Met Glu Tyr Ile Leu
                85                  90                  95

Gln Ala Thr Gly Asn Ala Ala Thr Gly Val Thr Trp Thr Thr Cys Leu
            100                 105                 110

Val Arg Ser Asp Tyr Lys Leu Tyr Asn Lys Asn Ser Ser Asn Ser
        115                 120                 125

Thr Leu Lys Asn Leu Gly Glu Arg His Thr Cys Gly Ser Val Thr Gln
    130                 135                 140

<210> SEQ ID NO 19
<211> LENGTH: 151
<212> TYPE: PRT
<213> ORGANISM: Artificial sequence
<220> FEATURE:
<223> OTHER INFORMATION: Chimeric Protein

<400> SEQUENCE: 19

Met Gly Ser Ser His His His His Ser Gly Leu Val Pro Arg
1               5                   10                  15

Gly Ser His Met Thr Lys Lys Ala Ala Val Ser Glu Leu Leu Gln Ala
            20                  25                  30

Ser Ala Pro Tyr Lys Ala Asp Val Glu Leu Cys Val Thr Ser Thr Asn
        35                  40                  45

Glu Thr Thr Asn Cys Thr Gly Gly Lys Asn Gly Ile Ala Ala Asp Ile
    50                  55                  60

Thr Thr Ala Lys Gly Tyr Val Lys Ser Val Thr Thr Ser Asn Gly Ala
65                  70                  75                  80

Ile Thr Val Lys Gly Asp Gly Thr Leu Ala Asn Met Glu Tyr Ile Leu
                85                  90                  95

Gln Ala Thr Gly Asn Ala Ala Thr Gly Val Thr Trp Thr Thr Cys Lys
            100                 105                 110

Gly Thr Asp Ala Ser Leu Phe Pro Ala Asn Phe Cys Gly Ser Val Thr
        115                 120                 125

Gln Arg Ser Asp Tyr Lys Leu Tyr Asn Lys Asn Ser Ser Ser Asn Ser
    130                 135                 140

Thr Leu Lys Asn Leu Gly Glu
145                 150

<210> SEQ ID NO 20
<211> LENGTH: 156
<212> TYPE: PRT
<213> ORGANISM: Artificial sequence
<220> FEATURE:
<223> OTHER INFORMATION: Chimeric Protein

<400> SEQUENCE: 20

Met Gly Ser Ser His His His His Ser Ser Gly Leu Val Pro Arg
1               5                   10                  15

Gly Ser His Met Thr Lys Lys Ala Ala Val Ser Glu Leu Leu Gln Ala
            20                  25                  30

Ser Ala Pro Tyr Lys Ala Asp Val Glu Leu Cys Val Thr Ser Thr Asn
        35                  40                  45

Glu Thr Thr Asn Cys Thr Gly Gly Lys Asn Gly Ile Ala Ala Asp Ile
50                  55                  60

Thr Thr Ala Lys Gly Tyr Val Lys Ser Val Thr Thr Ser Asn Gly Ala
65                  70                  75                  80

Ile Thr Val Lys Gly Asp Gly Thr Leu Ala Asn Met Glu Tyr Ile Leu
                85                  90                  95

Gln Ala Thr Gly Asn Ala Ala Thr Gly Val Thr Trp Thr Thr Cys Lys
                100                 105                 110

Gly Thr Asp Ala Ser Leu Phe Pro Ala Asn Phe Cys Gly Ser Val Thr
                115                 120                 125

Gln Leu Val Arg Ser Asp Tyr Lys Leu Tyr Asn Lys Asn Ser Ser Ser
130                 135                 140

Asn Ser Thr Leu Lys Asn Leu Gly Glu Arg His Thr
145                 150                 155

<210> SEQ ID NO 21
<211> LENGTH: 139
<212> TYPE: PRT
<213> ORGANISM: Artificial sequence
<220> FEATURE:
<223> OTHER INFORMATION: Chimeric Protein

<400> SEQUENCE: 21

Met Gly Ser Ser His His His His Ser Ser Gly Leu Val Pro Arg
1               5                   10                  15

Gly Ser His Met Thr Lys Lys Ala Ala Val Ser Glu Leu Leu Gln Ala
            20                  25                  30

Ser Ala Pro Tyr Lys Ala Asp Val Glu Leu Cys Arg Ser Asp Tyr Lys
        35                  40                  45

Leu Tyr Asn Lys Asn Ser Ser Ser Leu Lys Asn Leu Gly Glu Cys Thr
50                  55                  60

Gly Gly Lys Asn Gly Ile Ala Ala Asp Ile Thr Thr Ala Lys Gly Tyr
65                  70                  75                  80

Val Lys Ser Val Thr Thr Ser Asn Gly Ala Ile Thr Val Lys Gly Asp
                85                  90                  95

Gly Thr Leu Ala Asn Met Glu Tyr Ile Leu Gln Ala Thr Gly Asn Ala
                100                 105                 110

Ala Thr Gly Val Thr Trp Thr Thr Cys Lys Gly Thr Asp Ala Ser Leu
                115                 120                 125

Phe Pro Ala Asn Phe Cys Gly Ser Val Thr Gln
            130                 135

<210> SEQ ID NO 22
<211> LENGTH: 145
<212> TYPE: PRT
<213> ORGANISM: Artificial sequence
<220> FEATURE:
<223> OTHER INFORMATION: Chimeric Protein

<400> SEQUENCE: 22

Met Gly Ser Ser His His His His His His Ser Ser Gly Leu Val Pro Arg

```
                1               5                   10                  15
Gly Ser His Met Thr Lys Lys Ala Ala Val Ser Glu Leu Leu Gln Ala
            20                  25                  30

Ser Ala Pro Tyr Lys Ala Asp Val Glu Leu Cys Leu Val Arg Ser Asp
            35                  40                  45

Tyr Lys Leu Tyr Asn Lys Asn Ser Ser Thr Leu Lys Asn Leu Gly
    50                  55                  60

Glu Arg His Thr Cys Thr Gly Lys Asn Gly Ile Ala Ala Asp Ile
65                  70                  75                  80

Thr Thr Ala Lys Gly Tyr Val Lys Ser Val Thr Thr Ser Asn Gly Ala
                85                  90                  95

Ile Thr Val Lys Gly Asp Gly Thr Leu Ala Asn Met Glu Tyr Ile Leu
                100                 105                 110

Gln Ala Thr Gly Asn Ala Ala Thr Gly Val Thr Trp Thr Thr Cys Lys
                115                 120                 125

Gly Thr Asp Ala Ser Leu Phe Pro Ala Asn Phe Cys Gly Ser Val Thr
                130                 135                 140

Gln
145

<210> SEQ ID NO 23
<211> LENGTH: 136
<212> TYPE: PRT
<213> ORGANISM: Artificial sequence
<220> FEATURE:
<223> OTHER INFORMATION: Chimeric Protein

<400> SEQUENCE: 23

Met Gly Ser Ser His His His His Ser Ser Gly Leu Val Pro Arg
1               5                   10                  15

Gly Ser His Met Thr Lys Lys Ala Ala Val Ser Glu Leu Leu Gln Ala
            20                  25                  30

Ser Ala Pro Tyr Lys Ala Asp Val Glu Leu Cys Val Thr Ser Thr Asn
            35                  40                  45

Glu Thr Thr Asn Cys Thr Gly Gly Lys Asn Gly Ile Ala Ala Asp Ile
    50                  55                  60

Thr Thr Ala Lys Gly Tyr Val Lys Ser Val Thr Thr Ser Asn Gly Ala
65                  70                  75                  80

Ile Thr Val Lys Gly Asp Gly Thr Leu Ala Asn Met Glu Tyr Ile Leu
                85                  90                  95

Gln Ala Thr Gly Asn Ala Ala Thr Gly Val Thr Trp Thr Thr Cys Arg
                100                 105                 110

Ser Asp Tyr Lys Leu Tyr Asn Lys Asn Ser Ser Thr Leu Lys Asn Leu
                115                 120                 125

Gly Glu Cys Gly Ser Val Thr Gln
                130             135

<210> SEQ ID NO 24
<211> LENGTH: 141
<212> TYPE: PRT
<213> ORGANISM: Artificial sequence
<220> FEATURE:
<223> OTHER INFORMATION: Chimeric Protein

<400> SEQUENCE: 24

Met Gly Ser Ser His His His His Ser Ser Gly Leu Val Pro Arg
1               5                   10                  15
```

-continued

```
Gly Ser His Met Thr Lys Lys Ala Ala Val Ser Glu Leu Leu Gln Ala
            20                  25                  30

Ser Ala Pro Tyr Lys Ala Asp Val Glu Leu Cys Val Thr Ser Thr Asn
        35                  40                  45

Glu Thr Thr Asn Cys Thr Gly Gly Lys Asn Gly Ile Ala Ala Asp Ile
 50                  55                  60

Thr Thr Ala Lys Gly Tyr Val Lys Ser Val Thr Thr Ser Asn Gly Ala
 65                  70                  75                  80

Ile Thr Val Lys Gly Asp Gly Thr Leu Ala Asn Met Glu Tyr Ile Leu
                85                  90                  95

Gln Ala Thr Gly Asn Ala Ala Thr Gly Val Thr Trp Thr Thr Cys Leu
            100                 105                 110

Val Arg Ser Asp Tyr Lys Leu Tyr Asn Lys Asn Ser Ser Thr Leu Lys
            115                 120                 125

Asn Leu Gly Glu Arg His Thr Cys Gly Ser Val Thr Gln
            130                 135                 140
```

<210> SEQ ID NO 25
<211> LENGTH: 148
<212> TYPE: PRT
<213> ORGANISM: Artificial sequence
<220> FEATURE:
<223> OTHER INFORMATION: Chimeric Protein

<400> SEQUENCE: 25

```
Met Gly Ser Ser His His His His His Ser Ser Gly Leu Val Pro Arg
 1               5                  10                  15

Gly Ser His Met Thr Lys Lys Ala Ala Val Ser Glu Leu Leu Gln Ala
            20                  25                  30

Ser Ala Pro Tyr Lys Ala Asp Val Glu Leu Cys Val Thr Ser Thr Asn
        35                  40                  45

Glu Thr Thr Asn Cys Thr Gly Gly Lys Asn Gly Ile Ala Ala Asp Ile
 50                  55                  60

Thr Thr Ala Lys Gly Tyr Val Lys Ser Val Thr Thr Ser Asn Gly Ala
 65                  70                  75                  80

Ile Thr Val Lys Gly Asp Gly Thr Leu Ala Asn Met Glu Tyr Ile Leu
                85                  90                  95

Gln Ala Thr Gly Asn Ala Ala Thr Gly Val Thr Trp Thr Thr Cys Lys
            100                 105                 110

Gly Thr Asp Ala Ser Leu Phe Pro Ala Asn Phe Cys Gly Ser Val Thr
            115                 120                 125

Gln Arg Ser Asp Tyr Lys Leu Tyr Asn Lys Asn Ser Ser Thr Leu Lys
            130                 135                 140

Asn Leu Gly Glu
145
```

<210> SEQ ID NO 26
<211> LENGTH: 153
<212> TYPE: PRT
<213> ORGANISM: Artificial sequence
<220> FEATURE:
<223> OTHER INFORMATION: Chimeric Protein

<400> SEQUENCE: 26

```
Met Gly Ser Ser His His His His His Ser Ser Gly Leu Val Pro Arg
 1               5                  10                  15

Gly Ser His Met Thr Lys Lys Ala Ala Val Ser Glu Leu Leu Gln Ala
            20                  25                  30
```

```
Ser Ala Pro Tyr Lys Ala Asp Val Glu Leu Cys Val Thr Ser Thr Asn
        35                  40                  45

Glu Thr Thr Asn Cys Thr Gly Gly Lys Asn Gly Ile Ala Ala Asp Ile
 50                  55                  60

Thr Thr Ala Lys Gly Tyr Val Lys Ser Val Thr Thr Ser Asn Gly Ala
 65                  70                  75                  80

Ile Thr Val Lys Gly Asp Gly Thr Leu Ala Asn Met Glu Tyr Ile Leu
                 85                  90                  95

Gln Ala Thr Gly Asn Ala Ala Thr Gly Val Thr Trp Thr Thr Cys Lys
            100                 105                 110

Gly Thr Asp Ala Ser Leu Phe Pro Ala Asn Phe Cys Gly Ser Val Thr
        115                 120                 125

Gln Leu Val Arg Ser Asp Tyr Lys Leu Tyr Asn Lys Asn Ser Ser Thr
    130                 135                 140

Leu Lys Asn Leu Gly Glu Arg His Thr
145                 150
```

<210> SEQ ID NO 27
<211> LENGTH: 133
<212> TYPE: PRT
<213> ORGANISM: Artificial sequence
<220> FEATURE:
<223> OTHER INFORMATION: Chimeric Protein

<400> SEQUENCE: 27

```
Met Gly Ser Ser His His His His His Ser Ser Gly Leu Val Pro Arg
 1               5                  10                  15

Gly Ser His Met Thr Lys Lys Ala Ala Val Ser Glu Leu Leu Gln Ala
                 20                  25                  30

Ser Ala Pro Tyr Lys Ala Asp Val Glu Leu Cys Arg Ser Asp Tyr Lys
        35                  40                  45

Phe Tyr Asp Asn Lys Arg Ile Asp Cys Thr Gly Gly Lys Asn Gly Ile
 50                  55                  60

Ala Ala Asp Ile Thr Thr Ala Lys Gly Tyr Val Lys Ser Val Thr Thr
 65                  70                  75                  80

Ser Asn Gly Ala Ile Thr Val Lys Gly Asp Gly Thr Leu Ala Asn Met
                 85                  90                  95

Glu Tyr Ile Leu Gln Ala Thr Gly Asn Ala Ala Thr Gly Val Thr Trp
            100                 105                 110

Thr Thr Cys Lys Gly Thr Asp Ala Ser Leu Phe Pro Ala Asn Phe Cys
        115                 120                 125

Gly Ser Val Thr Gln
    130
```

<210> SEQ ID NO 28
<211> LENGTH: 138
<212> TYPE: PRT
<213> ORGANISM: Artificial sequence
<220> FEATURE:
<223> OTHER INFORMATION: Chimeric Protein

<400> SEQUENCE: 28

```
Met Gly Ser Ser His His His His His Ser Ser Gly Leu Val Pro Arg
 1               5                  10                  15

Gly Ser His Met Thr Lys Lys Ala Ala Val Ser Glu Leu Leu Gln Ala
                 20                  25                  30

Ser Ala Pro Tyr Lys Ala Asp Val Glu Leu Cys Leu Val Arg Ser Asp
```

```
            35                  40                  45
Tyr Lys Phe Tyr Asp Asn Lys Arg Ile Asp Arg His Thr Cys Thr Gly
 50                  55                  60

Gly Lys Asn Gly Ile Ala Ala Asp Ile Thr Thr Ala Lys Gly Tyr Val
 65                  70                  75                  80

Lys Ser Val Thr Thr Ser Asn Gly Ala Ile Thr Val Lys Gly Asp Gly
                 85                  90                  95

Thr Leu Ala Asn Met Glu Tyr Ile Leu Gln Ala Thr Gly Asn Ala Ala
            100                 105                 110

Thr Gly Val Thr Trp Thr Thr Cys Lys Gly Thr Asp Ala Ser Leu Phe
                115                 120                 125

Pro Ala Asn Phe Cys Gly Ser Val Thr Gln
            130                 135

<210> SEQ ID NO 29
<211> LENGTH: 130
<212> TYPE: PRT
<213> ORGANISM: Artificial sequence
<220> FEATURE:
<223> OTHER INFORMATION: Chimeric Protein

<400> SEQUENCE: 29

Met Gly Ser Ser His His His His Ser Ser Gly Leu Val Pro Arg
 1               5                  10                  15

Gly Ser His Met Thr Lys Lys Ala Ala Val Ser Glu Leu Leu Gln Ala
                 20                  25                  30

Ser Ala Pro Tyr Lys Ala Asp Val Glu Leu Cys Val Thr Ser Thr Asn
            35                  40                  45

Glu Thr Thr Asn Cys Thr Gly Gly Lys Asn Gly Ile Ala Ala Asp Ile
 50                  55                  60

Thr Thr Ala Lys Gly Tyr Val Lys Ser Val Thr Thr Ser Asn Gly Ala
 65                  70                  75                  80

Ile Thr Val Lys Gly Asp Gly Thr Leu Ala Asn Met Glu Tyr Ile Leu
                 85                  90                  95

Gln Ala Thr Gly Asn Ala Ala Thr Gly Val Thr Trp Thr Thr Cys Arg
            100                 105                 110

Ser Asp Tyr Lys Phe Tyr Asp Asn Lys Arg Ile Asp Cys Gly Ser Val
            115                 120                 125

Thr Gln
130

<210> SEQ ID NO 30
<211> LENGTH: 135
<212> TYPE: PRT
<213> ORGANISM: Artificial sequence
<220> FEATURE:
<223> OTHER INFORMATION: Chimeric Protein

<400> SEQUENCE: 30

Met Gly Ser Ser His His His His Ser Ser Gly Leu Val Pro Arg
 1               5                  10                  15

Gly Ser His Met Thr Lys Lys Ala Ala Val Ser Glu Leu Leu Gln Ala
                 20                  25                  30

Ser Ala Pro Tyr Lys Ala Asp Val Glu Leu Cys Val Thr Ser Thr Asn
            35                  40                  45

Glu Thr Thr Asn Cys Thr Gly Gly Lys Asn Gly Ile Ala Ala Asp Ile
 50                  55                  60
```

```
Thr Thr Ala Lys Gly Tyr Val Lys Ser Val Thr Ser Asn Gly Ala
 65                  70                  75                  80

Ile Thr Val Lys Gly Asp Gly Thr Leu Ala Asn Met Glu Tyr Ile Leu
                 85                  90                  95

Gln Ala Thr Gly Asn Ala Ala Thr Gly Val Thr Trp Thr Thr Cys Leu
            100                 105                 110

Val Arg Ser Asp Tyr Lys Phe Tyr Asp Asn Lys Arg Ile Asp Arg His
        115                 120                 125

Thr Cys Gly Ser Val Thr Gln
    130                 135

<210> SEQ ID NO 31
<211> LENGTH: 142
<212> TYPE: PRT
<213> ORGANISM: Artificial sequence
<220> FEATURE:
<223> OTHER INFORMATION: Chimeric Protein

<400> SEQUENCE: 31

Met Gly Ser Ser His His His His Ser Ser Gly Leu Val Pro Arg
 1               5                  10                  15

Gly Ser His Met Thr Lys Lys Ala Ala Val Ser Glu Leu Leu Gln Ala
                 20                  25                  30

Ser Ala Pro Tyr Lys Ala Asp Val Glu Leu Cys Val Thr Ser Thr Asn
            35                  40                  45

Glu Thr Thr Asn Cys Thr Gly Gly Lys Asn Gly Ile Ala Ala Asp Ile
 50                  55                  60

Thr Ala Lys Gly Tyr Val Lys Ser Val Thr Ser Asn Gly Ala
 65                  70                  75                  80

Ile Thr Val Lys Gly Asp Gly Thr Leu Ala Asn Met Glu Tyr Ile Leu
                 85                  90                  95

Gln Ala Thr Gly Asn Ala Ala Thr Gly Val Thr Trp Thr Thr Cys Lys
            100                 105                 110

Gly Thr Asp Ala Ser Leu Phe Pro Ala Asn Phe Cys Gly Ser Val Thr
        115                 120                 125

Gln Arg Ser Asp Tyr Lys Phe Tyr Asp Asn Lys Arg Ile Asp
    130                 135                 140

<210> SEQ ID NO 32
<211> LENGTH: 147
<212> TYPE: PRT
<213> ORGANISM: Artificial sequence
<220> FEATURE:
<223> OTHER INFORMATION: Chimeric Protein

<400> SEQUENCE: 32

Met Gly Ser Ser His His His His Ser Ser Gly Leu Val Pro Arg
 1               5                  10                  15

Gly Ser His Met Thr Lys Lys Ala Ala Val Ser Glu Leu Leu Gln Ala
                 20                  25                  30

Ser Ala Pro Tyr Lys Ala Asp Val Glu Leu Cys Val Thr Ser Thr Asn
            35                  40                  45

Glu Thr Thr Asn Cys Thr Gly Gly Lys Asn Gly Ile Ala Ala Asp Ile
 50                  55                  60

Thr Ala Lys Gly Tyr Val Lys Ser Val Thr Ser Asn Gly Ala
 65                  70                  75                  80

Ile Thr Val Lys Gly Asp Gly Thr Leu Ala Asn Met Glu Tyr Ile Leu
                 85                  90                  95
```

```
Gln Ala Thr Gly Asn Ala Ala Thr Gly Val Thr Trp Thr Thr Cys Lys
            100                 105                 110
Gly Thr Asp Ala Ser Leu Phe Pro Ala Asn Phe Cys Gly Ser Val Thr
        115                 120                 125
Gln Leu Val Arg Ser Asp Tyr Lys Phe Tyr Asp Asn Lys Arg Ile Asp
130                 135                 140
Arg His Thr
145

<210> SEQ ID NO 33
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 33 atg aaa tta aca aca cag caa acc ttg aaa aaa ggg ttt aca tta ata      48
Met Lys Leu Thr Thr Gln Gln Thr Leu Lys Lys Gly Phe Thr Leu Ile
1               5                   10                  15 gag cta atg att gtg att gca att att gct att tta gcc act atc gca      96
Glu Leu Met Ile Val Ile Ala Ile Ile Ala Ile Leu Ala Thr Ile Ala
                20                  25                  30 att ccc tct tat caa aat tat act aaa aaa gca gcg gta tct gaa tta     144
Ile Pro Ser Tyr Gln Asn Tyr Thr Lys Lys Ala Ala Val Ser Glu Leu
            35                  40                  45 ctg caa gcg tca gcg cct tat aag gct gat gtg gaa tta tgt gta tat     192
Leu Gln Ala Ser Ala Pro Tyr Lys Ala Asp Val Glu Leu Cys Val Tyr
        50                  55                  60 agc aca aat gaa aca aca aac tgt acg ggt gga aaa aat ggt att gca     240
Ser Thr Asn Glu Thr Thr Asn Cys Thr Gly Gly Lys Asn Gly Ile Ala
65                  70                  75                  80 gca gat ata acc aca gca aaa ggc tat gta aaa tca gtg aca aca agc     288
Ala Asp Ile Thr Thr Ala Lys Gly Tyr Val Lys Ser Val Thr Thr Ser
                85                  90                  95 aac ggt gca ata aca gta aaa ggg gat ggc aca ttg gca aat atg gaa     336
Asn Gly Ala Ile Thr Val Lys Gly Asp Gly Thr Leu Ala Asn Met Glu
            100                 105                 110 tat att ttg caa gct aca ggt aat gct gca aca ggt gta act tgg aca     384
Tyr Ile Leu Gln Ala Thr Gly Asn Ala Ala Thr Gly Val Thr Trp Thr
        115                 120                 125 aca act tgc aaa gga acg gat gcc tct tta ttt cca gca aat ttt tgc     432
Thr Thr Cys Lys Gly Thr Asp Ala Ser Leu Phe Pro Ala Asn Phe Cys
130                 135                 140 gga agt gtc aca caa                                                 447
Gly Ser Val Thr Gln
145

<210> SEQ ID NO 34
<211> LENGTH: 149
<212> TYPE: PRT
<213> ORGANISM: H. influenzae

<400> SEQUENCE: 34

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
                20                  25                  30

Ile Pro Ser Tyr Gln Asn Tyr Thr Lys Lys Ala Ala Val Ser Glu Leu
```

```
                    35                  40                  45
Leu Gln Ala Ser Ala Pro Tyr Lys Ala Asp Val Glu Leu Cys Val Tyr
 50                  55                  60

Ser Thr Asn Glu Thr Thr Asn Cys Thr Gly Gly Lys Asn Gly Ile Ala
 65                  70                  75                  80

Ala Asp Ile Thr Thr Ala Lys Gly Tyr Val Lys Ser Val Thr Thr Ser
                     85                  90                  95

Asn Gly Ala Ile Thr Val Lys Gly Asp Gly Thr Leu Ala Asn Met Glu
                100                 105                 110

Tyr Ile Leu Gln Ala Thr Gly Asn Ala Ala Thr Gly Val Thr Trp Thr
                115                 120                 125

Thr Thr Cys Lys Gly Thr Asp Ala Ser Leu Phe Pro Ala Asn Phe Cys
130                 135                 140

Gly Ser Val Thr Gln
145

<210> SEQ ID NO 35
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 35 atg aaa tta aca aca cag caa acc ttg aaa aaa ggg ttt aca tta ata        48
Met Lys Leu Thr Thr Gln Gln Thr Leu Lys Lys Gly Phe Thr Leu Ile
 1               5                  10                  15 gag cta atg att gtg att gca att att gct att tta gcc act atc gca        96
Glu Leu Met Ile Val Ile Ala Ile Ile Ala Ile Leu Ala Thr Ile Ala
                 20                  25                  30 att ccc tct tat caa aat tat act aaa aaa gca gcg gta tct gaa tta       144
Ile Pro Ser Tyr Gln Asn Tyr Thr Lys Lys Ala Ala Val Ser Glu Leu
             35                  40                  45 ctg caa gcg tca gcg cct tat aag gct gat gtg gaa tta tgt gta tat       192
Leu Gln Ala Ser Ala Pro Tyr Lys Ala Asp Val Glu Leu Cys Val Tyr
 50                  55                  60 agc aca aat gaa aca aca aac tgt acg ggt gga aaa aat ggt att gca       240
Ser Thr Asn Glu Thr Thr Asn Cys Thr Gly Gly Lys Asn Gly Ile Ala
 65                  70                  75                  80 gca gat ata acc aca gca aaa ggc tat gta aaa tca gtg aca aca agc       288
Ala Asp Ile Thr Thr Ala Lys Gly Tyr Val Lys Ser Val Thr Thr Ser
                 85                  90                  95 aac ggt gca ata aca gta aaa ggg gat ggc aca ttg gca aat atg gaa       336
Asn Gly Ala Ile Thr Val Lys Gly Asp Gly Thr Leu Ala Asn Met Glu
                100                 105                 110 tat att ttg caa gct aca ggt aat gct gca aca ggt gta act tgg aca       384
Tyr Ile Leu Gln Ala Thr Gly Asn Ala Ala Thr Gly Val Thr Trp Thr
            115                 120                 125 aca act tgc aaa gga acg gat gcc tct tta ttt cca gca aat ttt tgc       432
Thr Thr Cys Lys Gly Thr Asp Ala Ser Leu Phe Pro Ala Asn Phe Cys
130                 135                 140 gga agt gtc aca caa                                                    447
Gly Ser Val Thr Gln
145

<210> SEQ ID NO 36
<211> LENGTH: 149
<212> TYPE: PRT
<213> ORGANISM: H. influenzae
```

<400> SEQUENCE: 36

```
Met Lys Leu Thr Thr Gln Gln Thr Leu Lys Lys Gly Phe Thr Leu Ile
1               5                   10                  15
Glu Leu Met Ile Val Ile Ala Ile Ile Ala Ile Leu Ala Thr Ile Ala
            20                  25                  30
Ile Pro Ser Tyr Gln Asn Tyr Thr Lys Lys Ala Ala Val Ser Glu Leu
        35                  40                  45
Leu Gln Ala Ser Ala Pro Tyr Lys Ala Asp Val Glu Leu Cys Val Tyr
    50                  55                  60
Ser Thr Asn Glu Thr Thr Asn Cys Thr Gly Gly Lys Asn Gly Ile Ala
65                  70                  75                  80
Ala Asp Ile Thr Thr Ala Lys Gly Tyr Val Lys Ser Val Thr Thr Ser
                85                  90                  95
Asn Gly Ala Ile Thr Val Lys Gly Asp Gly Thr Leu Ala Asn Met Glu
            100                 105                 110
Tyr Ile Leu Gln Ala Thr Gly Asn Ala Ala Thr Gly Val Thr Trp Thr
        115                 120                 125
Thr Thr Cys Lys Gly Thr Asp Ala Ser Leu Phe Pro Ala Asn Phe Cys
    130                 135                 140
Gly Ser Val Thr Gln
145
```

<210> SEQ ID NO 37
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 37

```
atg aaa tta aca aca cag caa acc ttg aaa aaa ggg ttt aca tta ata    48
Met Lys Leu Thr Thr Gln Gln Thr Leu Lys Lys Gly Phe Thr Leu Ile
1               5                   10                  15 gag cta atg att gtg att gca att att gct att tta gcc act atc gca    96
Glu Leu Met Ile Val Ile Ala Ile Ile Ala Ile Leu Ala Thr Ile Ala
            20                  25                  30 att ccc tct tat caa aat tat act aaa aaa gca gcg gta tct gaa tta   144
Ile Pro Ser Tyr Gln Asn Tyr Thr Lys Lys Ala Ala Val Ser Glu Leu
        35                  40                  45 ctg caa gcg tca gcg cct tat aag gct gat gtg gaa tta tgt gta tat   192
Leu Gln Ala Ser Ala Pro Tyr Lys Ala Asp Val Glu Leu Cys Val Tyr
    50                  55                  60 agc aca aat gaa aca aca aac tgt acg ggt gga aaa aat ggt att gca   240
Ser Thr Asn Glu Thr Thr Asn Cys Thr Gly Gly Lys Asn Gly Ile Ala
65                  70                  75                  80 gca gat ata acc aca gca aaa ggc tat gta aaa tca gtg aca aca agc   288
Ala Asp Ile Thr Thr Ala Lys Gly Tyr Val Lys Ser Val Thr Thr Ser
                85                  90                  95 aac ggt gca ata aca gta aaa ggg gat ggc aca ttg gca aat atg gaa   336
Asn Gly Ala Ile Thr Val Lys Gly Asp Gly Thr Leu Ala Asn Met Glu
            100                 105                 110 tat att ttg caa gct aca ggt aat gct gca aca ggt gta act tgg aca   384
Tyr Ile Leu Gln Ala Thr Gly Asn Ala Ala Thr Gly Val Thr Trp Thr
        115                 120                 125 aca act tgc aaa gga acg gat gcc tct tta ttt cca gca aat ttt tgc   432
Thr Thr Cys Lys Gly Thr Asp Ala Ser Leu Phe Pro Ala Asn Phe Cys
    130                 135                 140
```

```
gga agt gtc aca caa                                              447
Gly Ser Val Thr Gln
145

<210> SEQ ID NO 38
<211> LENGTH: 149
<212> TYPE: PRT
<213> ORGANISM: H. influenzae

<400> SEQUENCE: 38

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 39
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 39 atg aaa tta aca aca cag caa acc ttg aaa aaa ggg ttt aca tta ata     48
Met Lys Leu Thr Thr Gln Gln Thr Leu Lys Lys Gly Phe Thr Leu Ile
1               5                   10                  15 gag cta atg att gtg att gca att att gct att tta gcc act atc gca     96
Glu Leu Met Ile Val Ile Ala Ile Ile Ala Ile Leu Ala Thr Ile Ala
            20                  25                  30 att ccc tct tat caa aat tat act aaa aaa gca gcg gta tct gaa tta    144
Ile Pro Ser Tyr Gln Asn Tyr Thr Lys Lys Ala Ala Val Ser Glu Leu
        35                  40                  45 ctg caa gcg tca gcg cct tat aag gct gat gtg gaa tta tgt gta tat    192
Leu Gln Ala Ser Ala Pro Tyr Lys Ala Asp Val Glu Leu Cys Val Tyr
    50                  55                  60 agc aca aat gaa aca aca aac tgt acg ggt gga aaa aat ggt att gca    240
Ser Thr Asn Glu Thr Thr Asn Cys Thr Gly Gly Lys Asn Gly Ile Ala
65                  70                  75                  80 gca gat ata acc aca gca aaa ggc tat gta aaa tca gtg aca aca agc    288
Ala Asp Ile Thr Thr Ala Lys Gly Tyr Val Lys Ser Val Thr Thr Ser
                85                  90                  95 aac ggt gca ata aca gta aaa ggg gat ggc aca ttg gca aat atg gaa    336
Asn Gly Ala Ile Thr Val Lys Gly Asp Gly Thr Leu Ala Asn Met Glu
```

```
                Asn Gly Ala Ile Thr Val Lys Gly Asp Gly Thr Leu Ala Asn Met Glu
                                100                 105                 110 tat att ttg caa gct aca ggt aat gct gca aca ggt gta act tgg aca         384
Tyr Ile Leu Gln Ala Thr Gly Asn Ala Ala Thr Gly Val Thr Trp Thr
            115                 120                 125 aca act tgc aaa gga acg gat gcc tct tta ttt cca gca aat ttt tgc         432
Thr Thr Cys Lys Gly Thr Asp Ala Ser Leu Phe Pro Ala Asn Phe Cys
        130                 135                 140 gga agt gtc aca caa                                                     447
Gly Ser Val Thr Gln
145

<210> SEQ ID NO 40
<211> LENGTH: 149
<212> TYPE: PRT
<213> ORGANISM: H. influenzae

<400> SEQUENCE: 40

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 41
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 41 atg aaa tta aca aca cag caa acc ttg aaa aaa ggt ttt aca tta atc         48
Met Lys Leu Thr Thr Gln Gln Thr Leu Lys Lys Gly Phe Thr Leu Ile
1               5                   10                  15 gag cta atg att gtg att gca att att gct att tta gcc act atc gca         96
Glu Leu Met Ile Val Ile Ala Ile Ile Ala Ile Leu Ala Thr Ile Ala
            20                  25                  30 att cct tct tat caa aat tat acc aaa aaa gct tcg gta tcc gaa tta         144
Ile Pro Ser Tyr Gln Asn Tyr Thr Lys Lys Ala Ser Val Ser Glu Leu
        35                  40                  45 ctg caa gca tct gca cct tat aag gct gat gtg gaa tta tgt gta tat         192
Leu Gln Ala Ser Ala Pro Tyr Lys Ala Asp Val Glu Leu Cys Val Tyr
    50                  55                  60
```

```
agc aca aat gaa aca aca aac tgt acg ggt gga aaa aat ggt att gca      240
Ser Thr Asn Glu Thr Thr Asn Cys Thr Gly Gly Lys Asn Gly Ile Ala
 65                  70                  75                  80 gct gat att aca aca gca aaa ggc tat gta gcc tca gtg aaa act caa      288
Ala Asp Ile Thr Thr Ala Lys Gly Tyr Val Ala Ser Val Lys Thr Gln
                 85                  90                  95 tcg ggt ggc att aca gta aaa ggg aat ggc aca ttg gca aat atg gaa      336
Ser Gly Gly Ile Thr Val Lys Gly Asn Gly Thr Leu Ala Asn Met Glu
            100                 105                 110 tat att ttg caa gct aaa ggt aat gct aca gca ggt gta act tgg aca      384
Tyr Ile Leu Gln Ala Lys Gly Asn Ala Thr Ala Gly Val Thr Trp Thr
        115                 120                 125 aca acc tgc aaa gga acg gat gcc tct tta ttt cca gca aat ttt tgc      432
Thr Thr Cys Lys Gly Thr Asp Ala Ser Leu Phe Pro Ala Asn Phe Cys
    130                 135                 140 aga agt gtc aca aaa                                                   447
Arg Ser Val Thr Lys
145

<210> SEQ ID NO 42
<211> LENGTH: 149
<212> TYPE: PRT
<213> ORGANISM: H. influenzae

<400> SEQUENCE: 42

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ser Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asn Gly Thr Leu Ala Asn Met Glu
            100                 105                 110

Tyr Ile Leu Gln Ala Lys Gly Asn Ala Thr Ala Gly Val Thr Trp Thr
        115                 120                 125

Thr Thr Cys Lys Gly Thr Asp Ala Ser Leu Phe Pro Ala Asn Phe Cys
    130                 135                 140

Arg Ser Val Thr Lys
145

<210> SEQ ID NO 43
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 43 atg aaa tta aca aca cag caa acc ttg aaa aaa ggg ttt aca tta ata       48
Met Lys Leu Thr Thr Gln Gln Thr Leu Lys Lys Gly Phe Thr Leu Ile
1               5                   10                  15 gag cta atg att gtg att gca att att gct att tta gcc acc atc gca       96
```

```
       Glu Leu Met Ile Val Ile Ala Ile Ile Ala Ile Leu Ala Thr Ile Ala
                        20                  25                  30 att cct tct tat aaa aat tat act aaa aaa gca gcg gta tct gaa tta         144
Ile Pro Ser Tyr Lys Asn Tyr Thr Lys Lys Ala Ala Val Ser Glu Leu
         35                  40                  45 ctg caa gct tct gcg cct tat aag gct gat gtg gaa tta tgt gta tat         192
Leu Gln Ala Ser Ala Pro Tyr Lys Ala Asp Val Glu Leu Cys Val Tyr
 50                  55                  60 agc aca aat gaa ata aca aat tgt atg ggt gga aaa aat ggt att gca         240
Ser Thr Asn Glu Ile Thr Asn Cys Met Gly Gly Lys Asn Gly Ile Ala
 65                  70                  75                  80 gct gat att aca aca gca aaa ggc tat gta gcc tca gtg aaa act caa         288
Ala Asp Ile Thr Thr Ala Lys Gly Tyr Val Ala Ser Val Lys Thr Gln
                 85                  90                  95 tcg ggt ggc att acc gta aaa ggg gat ggc aca ttg gca aat atg gaa         336
Ser Gly Gly Ile Thr Val Lys Gly Asp Gly Thr Leu Ala Asn Met Glu
                100                 105                 110 tat att ttg caa gct aca ggt aat gct gca gca ggt gta act tgg aca         384
Tyr Ile Leu Gln Ala Thr Gly Asn Ala Ala Ala Gly Val Thr Trp Thr
            115                 120                 125 aca acc tgc aaa gga acg gat gcc tct tta ttt cca gca aat ttt tgc         432
Thr Thr Cys Lys Gly Thr Asp Ala Ser Leu Phe Pro Ala Asn Phe Cys
        130                 135                 140 gga agt atc aca caa                                                     447
Gly Ser Ile Thr Gln
145

<210> SEQ ID NO 44
<211> LENGTH: 149
<212> TYPE: PRT
<213> ORGANISM: H. influenzae

<400> SEQUENCE: 44

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Lys Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Ile Thr Asn Cys Met Gly Gly Lys Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asp Gly Thr Leu Ala Asn Met Glu
            100                 105                 110

Tyr Ile Leu Gln Ala Thr Gly Asn Ala Ala Ala Gly Val Thr Trp Thr
        115                 120                 125

Thr Thr Cys Lys Gly Thr Asp Ala Ser Leu Phe Pro Ala Asn Phe Cys
    130                 135                 140

Gly Ser Ile Thr Gln
145

<210> SEQ ID NO 45
<211> LENGTH: 447
<212> TYPE: DNA
<213> ORGANISM: H. influenzae
<220> FEATURE:
```

-continued

```
<221> NAME/KEY: CDS
<222> LOCATION: (1)..(447)

<400> SEQUENCE: 45 atg aaa tta aca aca ctg caa acc ttg aaa aaa ggg ttt aca tta atc      48
Met Lys Leu Thr Thr Leu Gln Thr Leu Lys Lys Gly Phe Thr Leu Ile
1               5                   10                  15 gag cta atg att gtg att gca att att gct att tta gcc act atc gca      96
Glu Leu Met Ile Val Ile Ala Ile Ile Ala Ile Leu Ala Thr Ile Ala
            20                  25                  30 att cct tct tat caa aat tat acc aaa aaa gct gcg gta tcc gaa tta     144
Ile Pro Ser Tyr Gln Asn Tyr Thr Lys Lys Ala Ala Val Ser Glu Leu
        35                  40                  45 ctg caa gct tct gcg cct tat aag gct gat gtg gaa tta tgc gtt tat     192
Leu Gln Ala Ser Ala Pro Tyr Lys Ala Asp Val Glu Leu Cys Val Tyr
    50                  55                  60 agc aca ggc aaa cct tct act tgc tca gga gga agc aat gga att gca     240
Ser Thr Gly Lys Pro Ser Thr Cys Ser Gly Gly Ser Asn Gly Ile Ala
65                  70                  75                  80 gct gat att acg aca gca aaa ggc tat gta gcc tca gtg aaa act caa     288
Ala Asp Ile Thr Thr Ala Lys Gly Tyr Val Ala Ser Val Lys Thr Gln
                85                  90                  95 tca ggt ggt att aca gta aaa ggg aat ggc aca ttg gca aat atg gaa     336
Ser Gly Gly Ile Thr Val Lys Gly Asn Gly Thr Leu Ala Asn Met Glu
            100                 105                 110 tat att ttg caa gct aca ggt aat gct gca aca ggt gta act tgg aca     384
Tyr Ile Leu Gln Ala Thr Gly Asn Ala Ala Thr Gly Val Thr Trp Thr
        115                 120                 125 aca act tgc aaa gga acg gat gcc tct tta ttt cca gca aat ttt tgc     432
Thr Thr Cys Lys Gly Thr Asp Ala Ser Leu Phe Pro Ala Asn Phe Cys
    130                 135                 140 gga agt gtc aca caa                                                  447
Gly Ser Val Thr Gln
145

<210> SEQ ID NO 46
<211> LENGTH: 149
<212> TYPE: PRT
<213> ORGANISM: H. influenzae

<400> SEQUENCE: 46

Met Lys Leu Thr Thr Leu Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Gly Lys Pro Ser Thr Cys Ser Gly Gly Ser Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asn Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140
```

Gly Ser Val Thr Gln
145

<210> SEQ ID NO 47
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 47

| | | | | | | | | | | | | | | | | |
|---|---|---|---|---|---|---|---|---|---|---|---|---|---|---|---|---|
| atg | aaa | tta | aca | aca | ctg | caa | acc | ttg | aaa | aaa | ggg | ttt | aca | tta | atc | 48 |
| Met | Lys | Leu | Thr | Thr | Leu | Gln | Thr | Leu | Lys | Lys | Gly | Phe | Thr | Leu | Ile | |
| 1 | | | | 5 | | | | | 10 | | | | | 15 | | |
| gag | cta | atg | att | gtg | att | gca | att | att | gct | att | tta | gcc | act | atc | gca | 96 |
| Glu | Leu | Met | Ile | Val | Ile | Ala | Ile | Ile | Ala | Ile | Leu | Ala | Thr | Ile | Ala | |
| | | | 20 | | | | | 25 | | | | | 30 | | | |
| att | cct | tct | tat | caa | aat | tat | acc | aaa | aaa | gct | gcg | gta | tcc | gaa | tta | 144 |
| Ile | Pro | Ser | Tyr | Gln | Asn | Tyr | Thr | Lys | Lys | Ala | Ala | Val | Ser | Glu | Leu | |
| | | 35 | | | | | 40 | | | | | 45 | | | | |
| ctg | caa | gct | tct | gcg | cct | tat | aag | gct | gat | gtg | gaa | tta | tgc | gtt | tat | 192 |
| Leu | Gln | Ala | Ser | Ala | Pro | Tyr | Lys | Ala | Asp | Val | Glu | Leu | Cys | Val | Tyr | |
| 50 | | | | | 55 | | | | | 60 | | | | | | |
| agc | aca | ggc | aaa | ctt | tct | act | tgc | tca | gga | gga | agc | aat | gga | att | gca | 240 |
| Ser | Thr | Gly | Lys | Leu | Ser | Thr | Cys | Ser | Gly | Gly | Ser | Asn | Gly | Ile | Ala | |
| 65 | | | | | 70 | | | | | 75 | | | | | 80 | |
| gct | gat | att | aca | aca | gca | aaa | ggc | tat | gta | gcc | tca | gtg | aaa | act | caa | 288 |
| Ala | Asp | Ile | Thr | Thr | Ala | Lys | Gly | Tyr | Val | Ala | Ser | Val | Lys | Thr | Gln | |
| | | | | 85 | | | | | 90 | | | | | 95 | | |
| tca | ggt | ggt | att | aca | gta | aaa | ggg | aat | ggc | aca | ttg | gca | aat | atg | gaa | 336 |
| Ser | Gly | Gly | Ile | Thr | Val | Lys | Gly | Asn | Gly | Thr | Leu | Ala | Asn | Met | Glu | |
| | | | 100 | | | | | 105 | | | | | 110 | | | |
| tat | att | ttg | caa | gct | aaa | ggt | aat | gct | aca | gca | ggt | gta | act | tgg | aca | 384 |
| Tyr | Ile | Leu | Gln | Ala | Lys | Gly | Asn | Ala | Thr | Ala | Gly | Val | Thr | Trp | Thr | |
| | | 115 | | | | | 120 | | | | | 125 | | | | |
| aca | acc | tgc | aaa | gga | acg | gat | gcc | tct | tta | ttt | cca | gca | aat | ttt | tgc | 432 |
| Thr | Thr | Cys | Lys | Gly | Thr | Asp | Ala | Ser | Leu | Phe | Pro | Ala | Asn | Phe | Cys | |
| 130 | | | | | 135 | | | | | 140 | | | | | | |
| gga | agt | gtc | aca | aaa | | | | | | | | | | | | 447 |
| Gly | Ser | Val | Thr | Lys | | | | | | | | | | | | |
| 145 | | | | | | | | | | | | | | | | |

<210> SEQ ID NO 48
<211> LENGTH: 149
<212> TYPE: PRT
<213> ORGANISM: H. influenzae

<400> SEQUENCE: 48

Met Lys Leu Thr Thr Leu Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Gly Lys Leu Ser Thr Cys Ser Gly Gly Ser Asn Gly Ile Ala
65                  70                  75                  80

Ala Asp Ile Thr Thr Ala Lys Gly Tyr Val Ala Ser Val Lys Thr Gln

```
                    85                  90                  95
Ser Gly Gly Ile Thr Val Lys Gly Asn Gly Thr Leu Ala Asn Met Glu
            100                 105                 110

Tyr Ile Leu Gln Ala Lys Gly Asn Ala Thr Ala Gly Val Thr Trp Thr
            115                 120                 125

Thr Thr Cys Lys Gly Thr Asp Ala Ser Leu Phe Pro Ala Asn Phe Cys
            130                 135                 140

Gly Ser Val Thr Lys
145

<210> SEQ ID NO 49
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 49 atg aaa tta aca aca cag caa acc ttg aaa aaa ggt ttt aca tta atc      48
Met Lys Leu Thr Thr Gln Gln Thr Leu Lys Lys Gly Phe Thr Leu Ile
  1               5                  10                  15 gag cta atg att gtg att gca att att gct att tta gcc act atc gca      96
Glu Leu Met Ile Val Ile Ala Ile Ile Ala Ile Leu Ala Thr Ile Ala
             20                  25                  30 att cct tct tat caa aat tat acc aaa aaa gct tcg gta tcc gaa tta     144
Ile Pro Ser Tyr Gln Asn Tyr Thr Lys Lys Ala Ser Val Ser Glu Leu
         35                  40                  45 ctg caa gct tcc gca cct tat aag tca gat gtg gaa tta tgc gtt tat     192
Leu Gln Ala Ser Ala Pro Tyr Lys Ser Asp Val Glu Leu Cys Val Tyr
     50                  55                  60 agc aca ggc aaa cct tct act tgc tca gga gga agc aat gga att gca     240
Ser Thr Gly Lys Pro Ser Thr Cys Ser Gly Gly Ser Asn Gly Ile Ala
 65                  70                  75                  80 gct gat att aca aca gca aaa ggc tat gta gcc tca gtg aaa act caa     288
Ala Asp Ile Thr Thr Ala Lys Gly Tyr Val Ala Ser Val Lys Thr Gln
                 85                  90                  95 tca ggt ggt att aca gta aaa ggg aat ggc aca ttg gca aat atg gaa     336
Ser Gly Gly Ile Thr Val Lys Gly Asn Gly Thr Leu Ala Asn Met Glu
            100                 105                 110 tat att ttg caa gct aaa ggt aat gct aca gca ggt gta act tgg aca     384
Tyr Ile Leu Gln Ala Lys Gly Asn Ala Thr Ala Gly Val Thr Trp Thr
            115                 120                 125 aca acc tgc aaa gga acg gat gcc tct tta ttt cca gca aat ttt tgc     432
Thr Thr Cys Lys Gly Thr Asp Ala Ser Leu Phe Pro Ala Asn Phe Cys
            130                 135                 140 aga agt gtc aca aaa                                                  447
Arg Ser Val Thr Lys
145

<210> SEQ ID NO 50
<211> LENGTH: 149
<212> TYPE: PRT
<213> ORGANISM: H. influenzae

<400> SEQUENCE: 50

Met Lys Leu Thr Thr Gln Gln Thr Leu Lys Lys Gly Phe Thr Leu Ile
  1               5                  10                  15

Glu Leu Met Ile Val Ile Ala Ile Ile Ala Ile Leu Ala Thr Ile Ala
             20                  25                  30
```

```
Ile Pro Ser Tyr Gln Asn Tyr Thr Lys Lys Ala Ser Val Ser Glu Leu
        35                  40                  45

Leu Gln Ala Ser Ala Pro Tyr Lys Ser Asp Val Glu Leu Cys Val Tyr
 50                  55                  60

Ser Thr Gly Lys Pro Ser Thr Cys Ser Gly Gly Ser Asn Gly Ile Ala
 65                  70                  75                  80

Ala Asp Ile Thr Thr Ala Lys Gly Tyr Val Ala Ser Val Lys Thr Gln
                 85                  90                  95

Ser Gly Gly Ile Thr Val Lys Gly Asn Gly Thr Leu Ala Asn Met Glu
            100                 105                 110

Tyr Ile Leu Gln Ala Lys Gly Asn Ala Thr Ala Gly Val Thr Trp Thr
            115                 120                 125

Thr Thr Cys Lys Gly Thr Asp Ala Ser Leu Phe Pro Ala Asn Phe Cys
        130                 135                 140

Arg Ser Val Thr Lys
145
```

```
<210> SEQ ID NO 51
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 51
```

```
atg aaa tta aca aca cag caa acc ttg aaa aaa ggg ttt aca tta ata     48
Met Lys Leu Thr Thr Gln Gln Thr Leu Lys Lys Gly Phe Thr Leu Ile
 1               5                  10                  15 gag cta atg att gtg att gca att att gct att tta gcc act atc gca     96
Glu Leu Met Ile Val Ile Ala Ile Ile Ala Ile Leu Ala Thr Ile Ala
                 20                  25                  30 att ccc tct tat caa aat tat act aaa aaa gcg gcg gta tct gaa tta    144
Ile Pro Ser Tyr Gln Asn Tyr Thr Lys Lys Ala Ala Val Ser Glu Leu
        35                  40                  45 ctg caa gcg tca gcg cct tat aag gct gat gtg gaa tta tgt gta tat    192
Leu Gln Ala Ser Ala Pro Tyr Lys Ala Asp Val Glu Leu Cys Val Tyr
 50                  55                  60 agt aca ggt aaa cct tcc agt tgc tcg gga gga agc aat gga att gcg    240
Ser Thr Gly Lys Pro Ser Ser Cys Ser Gly Gly Ser Asn Gly Ile Ala
 65                  70                  75                  80 gct gat att aca aca gca aaa ggc tat gta aaa tca gtg aca aca agc    288
Ala Asp Ile Thr Thr Ala Lys Gly Tyr Val Lys Ser Val Thr Thr Ser
                 85                  90                  95 aac ggt gca ata aca gta aaa ggg gat ggc aca ttg gca aat atg gaa    336
Asn Gly Ala Ile Thr Val Lys Gly Asp Gly Thr Leu Ala Asn Met Glu
            100                 105                 110 tat att ttg caa gcc agt ggt aat gct gca aca ggt gta act tgg aca    384
Tyr Ile Leu Gln Ala Ser Gly Asn Ala Ala Thr Gly Val Thr Trp Thr
            115                 120                 125 aca act tgc aaa gga acg gat gcc tct tta ttt cca gca aat ttt tgc    432
Thr Thr Cys Lys Gly Thr Asp Ala Ser Leu Phe Pro Ala Asn Phe Cys
        130                 135                 140 gga agt gtc aca caa                                                 447
Gly Ser Val Thr Gln
145
```

```
<210> SEQ ID NO 52
<211> LENGTH: 149
<212> TYPE: PRT
```

<213> ORGANISM: H. influenzae

<400> SEQUENCE: 52

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Gly Lys Pro Ser Ser Cys Ser Gly Gly Ser Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Ser Gly Asn Ala Ala Thr Gly Val Thr Trp Thr
        115                 120                 125

Thr Thr Cys Lys Gly Thr Asp Ala Ser Leu Pro Ala Asn Phe Cys
    130                 135                 140

Gly Ser Val Thr Gln
145

<210> SEQ ID NO 53
<211> LENGTH: 40
<212> TYPE: PRT
<213> ORGANISM: Artificial sequence
<220> FEATURE:
<223> OTHER INFORMATION: Synthetic Peptide

<400> SEQUENCE: 53

Arg Ser Asp Tyr Lys Phe Tyr Glu Asp Ala Asn Gly Thr Arg Asp His
1               5                   10                  15

Lys Lys Gly Pro Ser Leu Lys Leu Leu Ser Leu Ile Lys Gly Val Ile
            20                  25                  30

Val His Arg Leu Glu Gly Val Glu
        35                  40

<210> SEQ ID NO 54
<211> LENGTH: 129
<212> TYPE: PRT
<213> ORGANISM: Artificial sequence
<220> FEATURE:
<223> OTHER INFORMATION: Chimeric protein

<400> SEQUENCE: 54

Gly Ser His Met Thr Lys Lys Ala Ala Val Ser Glu Leu Leu Gln Ala
1               5                   10                  15

Ser Ala Pro Tyr Lys Ala Asp Val Glu Leu Cys Leu Val Arg Ser Asp
            20                  25                  30

Tyr Lys Phe Tyr Glu Asp Ala Asn Gly Thr Arg Asp His Lys Lys Gly
        35                  40                  45

Arg His Thr Cys Thr Gly Gly Lys Asn Gly Ile Ala Ala Asp Ile Thr
    50                  55                  60

Thr Ala Lys Gly Tyr Val Lys Ser Val Thr Thr Ser Asn Gly Ala Ile
65                  70                  75                  80

Thr Val Lys Gly Asp Gly Thr Leu Ala Asn Met Glu Tyr Ile Leu Gln

```
                85                  90                  95
Ala Thr Gly Asn Ala Ala Thr Gly Val Thr Trp Thr Thr Cys Lys
            100                 105                 110

Gly Thr Asp Ala Ser Leu Phe Pro Ala Asn Phe Cys Gly Ser Val Thr
            115                 120                 125

Gln

<210> SEQ ID NO 55
<211> LENGTH: 126
<212> TYPE: PRT
<213> ORGANISM: Artificial sequence
<220> FEATURE:
<223> OTHER INFORMATION: Chimeric protein

<400> SEQUENCE: 55

Gly Ser His Met Thr Lys Lys Ala Ala Val Ser Glu Leu Leu Gln Ala
1               5                   10                  15

Ser Ala Pro Tyr Lys Ala Asp Val Glu Leu Cys Val Tyr Ser Thr Asn
                20                  25                  30

Glu Thr Thr Asn Cys Thr Gly Gly Lys Asn Gly Ile Ala Ala Asp Ile
            35                  40                  45

Thr Thr Ala Lys Gly Tyr Val Lys Ser Val Thr Ser Asn Gly Ala
        50                  55                  60

Ile Thr Val Lys Gly Asp Gly Thr Leu Ala Asn Met Glu Tyr Ile Leu
65                  70                  75                  80

Gln Ala Thr Gly Asn Ala Ala Thr Gly Val Thr Trp Thr Thr Cys
                85                  90                  95

Leu Val Arg Ser Asp Tyr Lys Phe Tyr Glu Asp Ala Asn Gly Thr Arg
            100                 105                 110

Asp His Lys Lys Gly Arg His Thr Cys Gly Ser Val Thr Gln
        115                 120                 125

<210> SEQ ID NO 56
<211> LENGTH: 138
<212> TYPE: PRT
<213> ORGANISM: Artificial sequence
<220> FEATURE:
<223> OTHER INFORMATION: Chimeric protein

<400> SEQUENCE: 56

Gly Ser His Met Thr Lys Lys Ala Ala Val Ser Glu Leu Leu Gln Ala
1               5                   10                  15

Ser Ala Pro Tyr Lys Ala Asp Val Glu Leu Cys Val Tyr Ser Thr Asn
                20                  25                  30

Glu Thr Thr Asn Cys Thr Gly Gly Lys Asn Gly Ile Ala Ala Asp Ile
            35                  40                  45

Thr Thr Ala Lys Gly Tyr Val Lys Ser Val Thr Ser Asn Gly Ala
        50                  55                  60

Ile Thr Val Lys Gly Asp Gly Thr Leu Ala Asn Met Glu Tyr Ile Leu
65                  70                  75                  80

Gln Ala Thr Gly Asn Ala Ala Thr Gly Val Thr Trp Thr Thr Cys
                85                  90                  95

Lys Gly Thr Asp Ala Ser Leu Phe Pro Ala Asn Phe Cys Gly Ser Val
            100                 105                 110

Thr Gln Leu Val Arg Ser Asp Tyr Lys Phe Tyr Glu Asp Ala Asn Gly
        115                 120                 125

Thr Arg Asp His Lys Lys Gly Arg His Thr
```

-continued

```
               130             135

<210> SEQ ID NO 57
<211> LENGTH: 144
<212> TYPE: PRT
<213> ORGANISM: Artificial sequence
<220> FEATURE:
<223> OTHER INFORMATION: Chimeric protein

<400> SEQUENCE: 57

Gly Ser His Met Leu Val Arg Ser Asp Tyr Lys Phe Tyr Glu Asp Ala
1               5                   10                  15

Asn Gly Thr Arg Asp His Lys Lys Gly Arg His Thr Gly Pro Ser Leu
            20                  25                  30

Lys Leu Thr Lys Lys Ala Ala Val Ser Glu Leu Leu Gln Ala Ser Ala
        35                  40                  45

Pro Tyr Lys Ala Asp Val Glu Leu Cys Val Tyr Ser Thr Asn Glu Thr
    50                  55                  60

Thr Asn Cys Thr Gly Gly Lys Asn Gly Ile Ala Ala Asp Ile Thr Thr
65                  70                  75                  80

Ala Lys Gly Tyr Val Lys Ser Val Thr Thr Ser Asn Gly Ala Ile Thr
                85                  90                  95

Val Lys Gly Asp Gly Thr Leu Ala Asn Met Glu Tyr Ile Leu Gln Ala
            100                 105                 110

Thr Gly Asn Ala Ala Thr Gly Val Thr Trp Thr Thr Thr Cys Lys Gly
        115                 120                 125

Thr Asp Ala Ser Leu Phe Pro Ala Asn Phe Cys Gly Ser Val Thr Gln
    130                 135                 140
```

TRANSCUTANEOUS *HAEMOPHILIUS INFLUENZAE* VACCINE FORMULATIONS AND METHODS

This application is a divisional application of U.S. patent application Ser. No. 14/773,556, filed Sep. 8, 2015, which is a national phase filing of International Application No. PCT US145/22871, filed Mar. 10, 2014, which claimed priority benefit of U.S. Provisional Application No. 61/775,132, all of which are incorporated herein by reference in their entirety.

STATEMENT AS TO FEDERALLY SPONSORED RESEARCH

This invention was made with government support under grant number DC003915 awarded by National Institutes of Health. The government has certain rights in the invention.

FIELD

The present subject matter is related to topical dosage forms and the topical delivery of active ingredients by the administration of a transcutaneous dosage form to the post-auricular region of a subject.

BACKGROUND

Topical dosage forms, including, e.g., creams, gels, liniments, balms, lotions, ointments, and patches, etc., are known to be effective delivery systems for a wide range of active ingredients. However, formulating topical dosage forms can be difficult as challenges, including, topical delivery specific issues, such as, penetration of the stratum corneum, poor storage-stability and generally low patient compliance, among others, are often not easy to overcome. Accordingly, there is a need for an improved storage-stable, topical dosage form, and/or method for administering the same, for treating and/or preventing one or more disease or disorder.

SUMMARY

The present subject matter provides topical delivery systems and methods of administering or using the same to treat or prevent diseases and/or elicit an immune response.

The topical delivery systems may include an active ingredient. The active ingredient may be a topical immunogenic composition. The topical immunogenic composition may be any topical immunogenic composition, including, e.g., a chimeric protein. The chimeric protein may include one or more one active agents. The active chimeric protein may include residues 40-149 of SEQ ID NO: 2 and SEQ ID NO: 4, SEQ ID NO: 4 being inserted before residue 40 of SEQ ID NO: 2. The active chimeric protein may include the amino acid sequence of SEQ ID NO: 57.

The topical delivery systems may include, e.g., a topical immunogenic composition as described herein and a flexible substrate in communication with the topical immunogenic composition. The topical immunogenic composition may also include one or more pharmaceutically acceptable topical carriers and/or adjuvants. The adjuvant may be any adjuvant. For example, the adjuvant may be any known adjuvant, including a mucosal adjuvant dmLT.

The active agent in the topical composition may be any active agent. For example the active agent may be an immunogenic active agent. The immunogenic active agent may be at least one vaccine or other active agent capable of eliciting an immune response. For example, the immunogenic active agent may include one or more chimeric protein, or fragments thereof. In this regard the immunogenic active agent may include an immunogenic PilA peptide selected from the group consisting of the amino acid sequence of SEQ ID NO: 6, SEQ ID NO: 7, SEQ ID NO: 8 and residues 40 to 149 of SEQ ID NO: 2. The immunogenic active agent may also include a portion of the LB1 peptide. The portion of the LB1 peptide, for example, may be selected from the group consisting of the amino acid sequence of SEQ ID NO: 4 and SEQ ID NO: 5, wherein the LB1 peptide is inserted before the immunogenic PilA peptide. The PilA peptide may be any PilA peptide. For example the PilA peptide may include, among others, residues 40-149 of SEQ ID NO: 2 and wherein the LB1 peptide comprises SEQ ID NO: 4. The chimeric protein comprises may include any amino acid sequence, including, e.g., the amino acid sequence of SEQ ID NO: 57.

The topical composition may also include one or more adjuvant or other pharmaceutically acceptable carriers. For example, the composition may include one or more mucosal adjuvant. The mucosal adjuvant may be any mucosal adjuvant, including, e.g., dmLT.

The topical delivery system comprises a flexible substrate. The flexible substrate may be any flexible substrate including, e.g., a patch, a poultice, a tape, etc. The flexible substrate may include a skin-contacting surface. In addition, the topical the topical pharmaceutical composition may be provided in or on the flexible substrate.

The flexible substrate may also include a backing. The backing may be an adhesive or occlusive backing. The backing may have one or more surfaces upon which one or more active agent may be in direct or indirect communication. For example, the backing may be in communication with an active containing layer that includes the at least one active agent or the topical pharmaceutical composition. The active agent containing layer may have a skin-contacting surface provided on one or more surface of the backing. The backing may include one or more polymers. The polymers may form a matrix as a layer in communication with the backing. In addition the polymers alone, or in combination may be adhesive. For example, a polymer matrix layer that does or does not comprises the topical composition may form a pressure-sensitive adhesive matrix layer. The polymeric matrix layer may release the active agent at a predetermined controlled rate.

According to the present methods and delivery systems, the topical delivery system may or may not contain a permeation enhancer and/or may or may not be applied using a penetration enhancer. Accordingly, hydration of the skin, as well as other permeation and penetration enhancers, are not required prior to the application of the topical delivery system.

The topical delivery system may be applied to the skin of a subject at a location proximate to a lymph node in the post-auricular region of the subject. The post-auricular region according to the present subject matter may not include of the subject's pinnae.

The present subject matter also provides methods for treating and/or preventing a disease or disorder in a subject. The methods may include applying, to at least a portion of the subject's post-auricular region, a topical delivery system comprising a therapeutically effective amount of a topical pharmaceutical composition comprising at least one active agent and a pharmaceutically acceptable carrier and/or adjuvant.

The disease or disorder to be prevented or treated may be any known disease disorder or pathological condition. For example, the disease or disorder may be an influenzae infection. The influenzae infection may be one or more of nontypeable *H. influenzae* (NTHi) infection, an *H. influenzae* a infection, an *H. influenzae* b infection, an *H. influenzae* c infection, an *H. influenzae* d infection, and/or an *H. influenzae* e infection.

In the event that the disease or disorder is an NTHi infection, the NTHi infection may be one or more of a middle ear NTHi infection, a nasopharynx NTHi infection or a lower airway NTHi infection.

In addition, the disease or disorder may be one or more pathological condition selected from the group consisting of otitis media, pneumonia, sinusitis, septicemia, endocarditis, epiglottitis, septic arthritis, meningitis, postpartum and neonatal infections, postpartum and neonatal sepsis, acute and chronic salpingitis, pericardis, cellulitis, osteomyelitis, endocarditis, cholecystitis, intraabdominal infections, urinary tract infection, mastoiditis, aortic graft infection, conjunctitivitis, Brazilian purpuric fever, occult bacteremia and exacerbation of underlying lung diseases such as chronic bronchitis, bronchietasis and cystic fibrosis.

The present subject matter further provides a method for eliciting an immune response to any bacteria. For example the bacteria may be an NTHi bacteria, including, e,g., an *H. influenzae* bacteria. The bacteria may also be, e.g., a *Streptococcus pneumnoniae* and/or *Moraxella catarrhalis*, among others. The method may include topically administering to at least a portion of a subject's post-auricular region, where the patient at risk of an NTHi bacterial infection, a topical delivery system including a topical immunogenic composition. The immunogenic composition may include at least one active agent. The at least one active agent may include an immunogenic dose of a protein. For example the protein may me a chimeric protein including, e.g., an immunogenic PilA peptide selected from the group consisting of the amino acid sequence of SEQ ID NO: 6, SEQ ID NO: 7, SEQ ID NO: 8, and residues 40 to 149 of SEQ ID NO: 2, and a portion of the LB1 peptide selected from the group consisting of the amino acid sequence of SEQ ID NO: 4 and SEQ ID NO: 5. The LB1 peptide may be inserted before the immunogenic PilA peptide. The PilA peptide may include residues 40-149 of SEQ ID NO: 2. The LB1 peptide may include SEQ ID NO: 4. Also, the protein may be a chimeric protein including the amino acid sequence of SEQ ID NO: 57. The topical immunogenic composition may also include one or more adjuvant, e.g., a mucosal adjuvant such as dmLT.

According to the present methods, the bacterial infection may be associated with or causes one or more disease or disorder selected from the group consisting of otitis media, pneumonia, sinusitis, septicemia, endocarditis, epiglottitis, septic arthritis, meningitis, sepsis, salpingitis, epiglottis, pericardis, cellulitis, osteomyelitis, endocarditis, cholecystitis, intraabdominal infections, urinary tract infection, mastoiditis, aortic graft infection, conjunctitivitis, Brazilian purpuric fever, occult bacteremia, chronic obstructive pulmonary disease, chronic bronchitis, bronchietasis, and cystic fibrosis.

The presently described subject matter is directed to a method wherein administering comprises applying the topical delivery system at least once.

The presently described subject matter is directed to a method wherein administering comprises applying the topical delivery system once a week, at weekly intervals, for a pre-determined period of time.

The presently described subject matter is directed to a method wherein the predetermined period of time is from 2 weeks to 10 weeks.

The presently described subject matter is directed to a method wherein the predetermined period of time is 2 weeks.

The presently described subject matter is directed to a method wherein the topical delivery system remains on the patient for a period of at least 24 hours.

DETAILED DESCRIPTION

Definitions

Figure 1:
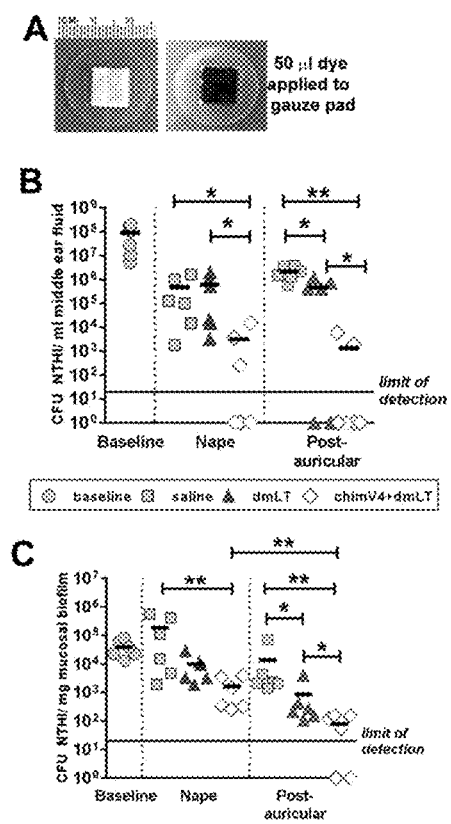
FIG. 1 is a graphical representation of resolution of clinically-relevant signs of experimental OM as determined by video otoscopy and tympanometry. Boxes around days 0 and 7 on x-axis indicate days of vaccination. *$p<0.05$ compared to receipt of saline; +$p<0.05$ compared to receipt of dmLT alone. N=4 middle ears per cohort on day 0; N=6 middle ears per cohort on days 3-14.

The term "about" as used herein refers to a quantity, level, value, dimension, size, or amount that varies to some extent based on the context in which it is used. For example, such variation can be by as much as 5%. At the least, each numerical parameter can be construed in light of the number of reported significant digits and by applying ordinary rounding techniques.

As used herein, the terms "administer," "administering," and "administration," refer to any method which, in sound medical practice, delivers the composition to a subject in such a manner as to provide a therapeutic effect.

As used herein, the term "adjuvant" refers to a substance added to a topical pharmaceutical composition to assist the action of the active agent.

As used herein, the term "mucosal adjuvant" refers to protein or oligonucleotides with immunopotentiating properties that can be co-administered with pathogen derived antigens. Such adjuvants can include dmLT and mutants of heat labile enterotoxin from Escherichia coli and cholera toxin from Vibrio cholera including two mutants of the enzymatic A subunit, LTK63 and LTR72, maintain a high degree of adjuvanticity. LTK63 results from the substitution of serine 63 with a lysine in the A subunit, which renders it enzymatically inactive and non-toxic. LTR72 is derived from a substitution of alanine 72 with an arginine in the A subunit, and has approximately 0.6% of the enzymatic activity of wild-type LT. LTR72 is shown to be 100,000 times less toxic than wild-type LT in Y1 cells in vitro and 25-100 times less toxic than wild-type LT in the rabbit ileal loop assay.

As used herein, the term "particulate mucosal adjuvant" refers to adjuvants including emulsions, microparticles, iscoms, and liposomes that can have comparable dimensions to the pathogens that the immune system has evolved to combat. Such particulate adjuvants can include, for example, particles including polymers or proteins which self-assemble into particles, biodegradable and biocompatible polyesters, the polylactide-coglycolides (PLG), where the antigen is associated with the particles, for example, by encapsulation or adsorption onto the particle surface. The presently described topical pharmaceutical compositions can comprise one or more adjuvants including one or more mucosal adjuvants and/or particulate mucosal adjuvants.

As used herein, the term "backing" refers to a layer for application to an area of skin that conforms to the skin.

As used herein, the term "adhesive backing" refers to a layer for application to an area of skin of which at least a portion of the backing adheres and conforms to the skin to which it is applied.

As used herein, the term "occlusive backing" refers to a layer for application to an area of skin that retains moisture and heat while increasing the concentration and absorption of an active agent being topically applied. An occlusive backing can be an adhesive occlusive backing. The occlusive backing conforms to the area of skin to which it is applied.

As used herein, the phrases an "effective amount" or a "therapeutically effective amount" of an active agent or ingredient, or pharmaceutically active agent or ingredient, which are synonymous herein, refer to an amount of the pharmaceutically active agent sufficient enough to have a therapeutic effect upon administration. A therapeutically effective amount of the pharmaceutically active agent may, will, or is expected to cause a relief of symptoms. Effective amounts of the pharmaceutically active agent will vary with the particular condition or conditions being treated, the severity of the condition, the duration of the treatment, the specific components of the composition being used, and like factors.

The term "flexible substrate," as used herein, refers to a substrate comprising single or multiple layers for the transdermal delivery of one or more active agents when applied to an area of skin of a patient, for example, a pediatric patient. Suitable flexible substrates can include, but are not limited to, bandages, cotton pads, gauze pads, poultices, tapes, and skin patches. Skin patches can include, but are not limited to, "reservoir" patches and "matrix" patches. Patches may be single- or multi-layered. A "reservoir" patch can have a liquid or gel compartment containing the drug solution or suspension separated by a membrane and a layer of adhesive. In a "matrix" patch, the drug can be present, for example, dispersed or suspended, in a semi-solid or solid layer, which may or may not be adhesive or comprise an adhesive material. Such flexible substrates can include a backing and/or an active containing layer. A topical pharmaceutical composition containing at least one active agent or at least one active agent can be in contact or communication with the backing and/or any other layer, for example a polymeric matrix layer, provided the active agent is in contact with an area of skin to which the system is applied, during use. One or more active agents can be dispersed in, suspended in, or coated on a skin-contacting surface of an active agent containing layer.

As used herein, the term "influenzae infection" refers to a bacterial infection caused by the microbe *Haemophilus influenza*.

As used herein, the terms "optional" or "optionally" mean that the subsequently described event or circumstance may or may not occur, and that the description includes instances where said event or circumstance occurs and instances where it does not.

The phrase "pharmaceutically acceptable topical carrier" as used herein refers to any inactive ingredient present in one of the herein described compositions in an amount effective to enhance the stability, effectiveness, or otherwise of the composition. Non-limiting examples of such pharmaceutically acceptable carriers include diluents, excipients, suspending agents, adjuvants, vehicles, delivery systems, emulsifiers, disintegrants, absorbants, adsorbents, preservatives, surfactants, colorants, flavorants, emollients, buffers, pH modifiers, thickeners, water softening agents, humectants, fragrances, stabilizers, conditioning agents, chelating agents, sweeteners, propellants, viscosity increasing agents, solubilizers, plasticizers, penetration enhancing agents, film forming agents, antioxidants, stiffening agents, wetting agents, or any mixture of one or more of these components.

As used herein, the term "polymeric matrix layer" refers to a layer comprising one or more polymers for the release of one or more active agents. The polymeric matrix layer can be an adhesive, i.e., an adhesive polymeric matrix layer that adheres and conforms to an area of skin to which it is applied. The polymeric matrix layer can be a pressure-sensitive adhesive polymeric matrix layer, comprising for example, one or more of polyurethane, PMMA, styrene-butadiene copolymer, and silicone. The polymeric matrix layer can comprise one or more active agents.

The polymer matrix layer can include an active agent homogeneously combined in a biocompatible pressure sensitive polymer adhesive which may or may not also contain other components. The topical delivery system can comprise an adhesive patch having an impermeable film backing and, before transdermal application, a release liner on the surface of the adhesive opposite the film backing. The topical delivery system can comprise a unit dosage form of an active agent in a topical pharmaceutical composition that is in a matrix comprising an adhesive polymer. The pressure sensitive adhesive and the topical pharmaceutical composition containing the active agent can be homogeneously combined.

As used herein, the term "postauricular region" refers to the area behind the auricle of the ear. The postauricular region may include the skin near or proximate the postauricular lymph node. The postauricular region does not include any portion of the pinnae.

As used herein the term "preservative" refers to any known pharmaceutically acceptable preservative that functions by inhibiting bacteria and/or fungi, and/or yeast, and/or mold, and/or other microbe, and/or by inhibiting oxidation. Suitable preservatives can include but are not limited to antimicrobial agents and/or antioxidants. Suitable antimicrobial agents can include but are not limited to benzoates, benzyl alcohol, sodium benzoate, sorbates, propionates, and nitrites. Suitable antioxidants can include but are not limited to vitamin C, butylated hydroxytoluene (BHT), sulphites, and vitamin E.

The term "prevent," "preventing," or "prevention," as used herein refers to any reduction, no matter how slight, of a subject's predisposition or risk for developing a disease or disorder. The term "prevention" includes either preventing the onset of a clinically evident disease or disorder altogether or preventing the onset of a pre-clinically evident infection in individuals at risk. This includes prophylactic treatment of subjects at risk of developing a disease or disorder as presently described.

The phrase "substantially pure" as used herein refers to an individual compound form, which is substantially devoid of all other forms, as well as degradation products of a form, and any residual solvent, and is at least 85 wt % pure, unless otherwise specified. The compound form can have at least 90 wt % purity, at least 93 wt % purity, at least 95 wt % purity, or at least 97 wt % purity.

As used herein, "subject" or "individual" or "animal" or "patient" or "mammal," refers to any subject, particularly a mammalian subject, for whom diagnosis, prognosis, or therapy is desired, for example, a human, for example a pediatric human patient.

As used herein, the term "topical delivery system" refers to a pharmaceutical dosage form that comprises a flexible substrate and at least one topical pharmaceutical composition. The flexible substrate may include a backing or backing layer that provides a protective outer surface for the system, as well as a release liner or layer that covers an adhesive portion of the system that is used to affix the same to the skin of a patient. The release liner is removed prior to application, thereby exposing the adhesive portion of the system, which can be a pressure-sensitive adhesive. The topical delivery system can be storage-stable at room temperature.

The flexible substrate can include single or multiple layers for the transdermal delivery of one or more active agents when applied to an area of skin of a patient, for example, a pediatric patient. Suitable topical delivery systems can include, but are not limited to, skin patches, including "reservoir" patches and "matrix" patches. Patches may be single- or multi-layered. A "reservoir" patch essentially has a liquid or gel compartment containing the active agent in solution or suspension separated by a membrane and a layer of adhesive. In a "matrix" patch, the active agent can be present, for example, dispersed or suspended, in a semi-solid or solid layer, which may or may not be adhesive or comprise an adhesive material. Such systems can include a backing or backing layer and/or an active containing layer. An active agent can be in contact or communication with the backing and/or any other layer, for example a polymeric matrix layer, provided the active agent is in contact with an area of skin to which the system is applied, during use. One or more active agents can be dispersed in, suspended in, or coated on a skin-contacting surface of an active containing layer.

A patch can comprise a backing layer and a reservoir provided on a portion of the backing layer. The reservoir can be configured for releaseably containing at least one active agent for transdermal delivery when applied to an area of skin of a patient, for example a pediatric patient. The reservoir can be mounted on a portion of a lower surface the backing layer.

The patch can comprise a skin adhesive layer disposed on at least a portion of a lower surface of the backing layer of the patch such that the patch can be applied or releasably applied to an area of skin of the patient.

As used herein, the term "transdermal" means the application of one or more active agents, to the skin. Transdermal application can result in transdermal delivery, where the active agent is delivered across one or more layers of the skin. Likewise, as used herein, the term "transcutaneous" means the application of a composition and/or one or more active agents, to the epidermis which may result in the delivery of the one or more active agents across at least the epidermis.

As used herein, the term "transcutaneous immunization" means the application of an immunogenic substance, e.g., a vaccine onto skin, to induce an immune response, which may include, e.g., engaging antigen-presenting cells present within the epidermis and dermis, the Langerhan's cells and dermal dendritic cells respectively.

As used herein, a "treatment" or "treating" of a disease, disorder, or condition encompasses alleviation of at least one symptom thereof, a reduction in the severity thereof, or the delay or inhibition of the progression thereof. Treatment need not mean that the disease, disorder, or condition is totally cured. A useful composition herein needs only to reduce the severity of a disease, disorder, or condition, reduce the severity of symptoms associated therewith, provide improvement to a patient or subject's quality of life, or delay or inhibit the onset of a disease, disorder, or condition.

Any concentration ranges, percentage range, or ratio range recited herein are to be understood to include concentrations, percentages or ratios of any integer within that range and fractions thereof, such as one tenth and one hundredth of an integer, unless otherwise indicated.

Any number range recited herein relating to any physical feature, such as polymer subunits, size or thickness, are to be understood to include any integer within the recited range, unless otherwise indicated.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a," "an" and "at least one" are used interchangeably in this application. For example, "a" thickener refers to both one thickener or a mixture comprising two or more thickeners.

Unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained.

Throughout the application, descriptions of various embodiments use "comprising" language; however, it will be understood by one of skill in the art, that in some specific instances, an embodiment can alternatively be described using the language "consisting essentially of" or "consisting of."

For the purpose of clarity, any element or feature of any method or composition described herein, can be combined with any other element or feature of any other method or composition described herein.

Other terms as used herein are meant to be defined by their well-known meanings in the art.

NTHi Type IV Pilus (PilA) Polynucleotides and Polypeptides

The chimeric proteins of the presently described subject matter may comprise the full length or a portion of the major subunit of the NTHi Type IV Pilus which is encoded by the gene pilA. The PilA protein of the NTHi isolate 86-028NP is encoded by the nucleic acid sequence set out as SEQ ID NO: 2, which is described in U.S. patent application Ser. No. 11/019,005, incorporated by reference herein in its entirety. Also provided are polynucleotides encoding PilA polypeptides from NTHi clinical isolates 1728MEE, 1729MEE, 3224A, 10548MEE, 1060MEE, 1885MEE, 1714MEE, 1236MEE, 1128MEE and 214NP. The amino acid sequences of these PilA polypeptides are set out in SEQ ID NOS: 34, 36, 38, 40, 42, 44, 46, 48, 50 and 52 respectively. The possibility of alternative codon usage is specifically contemplated in polynucleotides encoding the polypeptides. In one embodiment, the polypeptides are respectively encoded by the nucleotide sequences set out in SEQ ID NOS: 33, 35, 37, 39, 41, 43, 45, 47, 49 and 51.

The presently described subject matter provides for polynucleotides that hybridize under stringent conditions to (a) the complement of the nucleotide sequences set out in SEQ ID NOS: 1, 33, 35, 37, 39, 41, 43, 45, 47, 49 and 51; (b) a polynucleotide which is an allelic variant of any polynucleotides recited above; (c) a polynucleotide which encodes a species homolog of any of the proteins recited above; or (d) a polynucleotide that encodes a polypeptide comprising a specific domain or truncation of the polypeptides of the presently described subject matter. PilA polynucleotides from other non-typeable *H. influenzae* strains and from *H. influenzae* strains a, b, c, e and f are specifically contemplated. These polynucleotides can be identified and isolated by techniques standard in the art such as hybridization and polymerase chain reaction using part or all of the polynucleotides of SEQ ID NOS: 1, 33, 35, 37, 39, 41, 43, 45, 47, 49 and 51 as probes or primers, respectively.

The polynucleotides of the presently described subject matter also include nucleotide sequences that are substantially equivalent to the polynucleotides recited above. Polynucleotides according to the presently described subject matter can have, e.g., at least 65%, at least 70%, at least 75%, at least 80%, 81%, 82%, 83%, 84%, 85%, 86%, 87%, 88%, or 89%, more typically at least 90%, 91%, 92%, 93%, or 94% and even more typically at least 95%, 96%, 97%, 98%, or 99% sequence identity to the NTHi polynucleotides recited above.

Included within the scope of the nucleic acid sequences of the presently described subject matter are nucleic acid sequence fragments that hybridize under stringent conditions to the NTHi nucleotide sequences of SEQ ID NOS: 1, 33, 35, 37, 39, 41, 43, 45, 47, 49 and 51, or complements thereof, which fragment is greater than about 5 nucleotides, 7 nucleotides, greater than 7 nucleotides, greater than 9 nucleotides, and greater than 17 nucleotides. Fragments of, e.g., 15, 17, or 20 nucleotides or more that are selective for (i.e., specifically hybridize to any one of the PilA polynucleotides of the presently described subject matter) are suitable. These nucleic acid sequence fragments capable of specifically hybridizing to an NTHi PilA polynucleotide of the presently described subject matter can be used as probes to detect NTHi PilA polynucleotides of the presently described subject matter and/or can differentiate NTHi PilA polynucleotides of the presently described subject matter from other bacterial genes, and are preferably based on unique nucleotide sequences.

The term "stringent" is used herein to refer to conditions that are commonly understood in the art as stringent. Hybridization stringency is principally determined by temperature, ionic strength, and the concentration of denaturing agents such as formamide. Examples of stringent conditions for hybridization and washing are 0.015 M sodium chloride, 0.0015 M sodium citrate at 65-68° C. or 0.015 M sodium chloride, 0.0015M sodium citrate, and 50% folinamide at 42° C. See Sambrook et al., Molecular Cloning: A Laboratory Manual, 2nd Ed., Cold Spring Harbor Laboratory, (Cold Spring Harbor, N.Y. 1989).

More stringent conditions (such as higher temperature, lower ionic strength, higher formamide, or other denaturing agent) may also be used; however, the rate of hybridization will be affected. In instances where hybridization of deoxyoligonucleotides is concerned, additional exemplary stringent hybridization conditions include washing in 6×SSC 0.05% sodium pyrophosphate at 37° C. (for 14-base oligos), 48° C. (for 17-base oligos), 55° C. (for 20-base oligos), and 60° C. (for 23-base oligos).

Other agents may be included in the hybridization and washing buffers for the purpose of reducing non-specific and/or background hybridization. Examples include 0.1% bovine serum albumin, 0.1% polyvinyl-pyrrolidone, 0.1% sodium pyrophosphate, 0.1% sodium dodecylsulfate, NaDodSO4, (SDS), ficoll, Denhardt's solution, sonicated salmon sperm DNA (or other non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4, however, at typical ionic strength conditions, the rate of hybridization is nearly independent of pH. See Anderson et al., Nucleic Acid Hybridisation: A Practical Approach, Ch. 4, IRL Press Limited (Oxford, England). Hybridization conditions can be adjusted by one skilled in the art in order to accommodate these variables and allow DNAs of different sequence relatedness to form hybrids.

As noted above, suitable polynucleotides are not limited to the specific PilA polynucleotides of SEQ ID NOS: 1, 33, 35, 37, 39, 41, 43, 45, 47, 49 and 51, but also include, for example, allelic and species variations thereof. Allelic and species variations can be routinely determined by comparing the sequence provided in SEQ ID NOS: 1, 33, 35, 37, 39, 41, 43, 45, 47, 49 and 51, preferably the open reading frames therein, a representative fragment thereof, or a nucleotide sequence at least 90% identical, preferably 95% identical, to the open reading frames within SEQ ID NOS: 1, 33, 35, 37, 39, 41, 43, 45, 47, 49 and 51 with a sequence from another isolate of the same species or another species. Computer program methods to determine identity and similarity between two sequences include, but are not limited to, the GCG program package, including GAP (Devereux et al., Nucl. Acid. Res., 12: 387, 1984; Genetics Computer Group, University of Wisconsin, Madison, Wis.), BLASTP, BLASTN, and FASTA (Altschul et al., J. Mol. Biol., 215: 403-410, 1990). The BLASTX program is publicly available from the National Center for Biotechnology Information (NCBI) and other sources (BLAST Manual, Altschul et al. NCB/NLM/NIH Bethesda, Md. 20894; Altschul et aL, supra). The well known Smith-Waterman algorithm may also be used to determine identity.

Polynucleotides of the presently described subject matter may be isolated from natural sources or may be synthesized by standard chemical techniques, e.g., the phosphotriester method described in Matteucci et al., J Am Chem Soc., 103: 3185 (1981).

The presently described subject matter provides for chimeric proteins comprising a portion of NTHi PilA protein. The polypeptides can comprise the NTHi 86-028NP amino acid sequences respectively set out in SEQ ID NO: 2. Polypeptides of the presently described subject matter may also include PilA polypeptides set out in SEQ ID NOS: 34, 36, 38, 40, 42, 44, 46, 48, 50 and 52. The PilA polypeptides of the presently described subject matter can be those of other non-typeable H. influenzae strains and from H. influenzae strains a, b, c, e and f.

Polypeptides of the presently described subject matter specifically include peptide fragments (i.e., peptides) or fragments of the PilA polypeptide that retain one or more biological or immunogenic properties of a full length polypeptide of the presently described subject matter. In one embodiment, PilA peptide fragments provided by the presently described subject matter are designated TfpQ2, TfpQ3, TfpQ4 and OLP3 and respectively comprise amino acids 35 through 68 of SEQ ID NO: 2, amino acids 69 through 102 of SEQ ID NO: 2, amino acids 103 through 137 of SEQ ID NO: 2, and amino acids 21 through 35 of SEQ ID NO: 2. Another PilA peptide fragment provided by the presently described subject matter comprises amino acids 40 through 149 of SEQ ID NO: 2.

The presently described subject matter also provides for chimeric proteins comprising a portion of a PilA polypeptide with one or more conservative amino acid substitutions that do not affect the biological and/or immunogenic activity of the PilA polypeptide. Alternatively, the PilA polypeptides of the presently described subject matter can have conservative amino acids substitutions which may or may not alter biological activity. The term "conservative amino acid substitution" refers to a substitution of a native amino acid residue with a nonnative residue, including naturally occurring and nonnaturally occurring amino acids, such that there is little or no effect on the polarity or charge of the amino acid residue at that position. For example, a conservative substitution results from the replacement of a non-polar residue in a polypeptide with any other non-polar residue. Further, any native residue in the polypeptide may also be substituted with alanine, according to the methods of "alanine scanning mutagenesis." Naturally occurring amino acids are characterized based on their side chains as follows: basic: arginine, lysine, histidine; acidic: glutamic acid, aspartic acid; uncharged polar: glutamine, asparagine, serine, threonine, tyrosine; and non-polar: phenylalanine, tryptophan, cysteine, glycine, alanine, valine, proline, methionine, leucine, norleucine, isoleucine. General rules for amino acid substitutions are set forth in Table 1 below.

TABLE 1

Amino Acid Substitutions

| Original Residues | Exemplary Substitutions | Preferred Substitutions |
| --- | --- | --- |
| Ala | Val, Leu, Ile | Val |
| Arg | Lys, Gln, Asn | Lys |
| Asn | Gin | Gln |
| Asp | Glu | Glu |
| Cys | Ser, Ala | Ser |
| Gln | Asn | Asn |
| Glu | Asp | Asn |
| Gly | Pro, Ala | Ala |
| His | Asn, Gln, Lys, Arg | Arg |
| Ile | Leu, Val, Met, Ala, Phe, | Leu |
| Leu | Norleucine, Ile, Val, Met, | Leu |
| Lys | Arg, 1,4 Diaminobutyric | Arg |
| Met | Leu, Phe, Ile | Leu |
| Phe | Leu, Val, Ile, Ala, Tyr | Arg |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, | Leu |

The presently described subject matter also provides for chimeric proteins comprising a portion of a variants of the NTHi PilA polypeptides of the presently described subject matter (e.g., a polypeptide exhibiting at least about 65%, at least about 70%, at least about 75%, at least about 80%, at least about 85%, 86%, 87%, 88%, 89%, at least about 90%, 91%, 92%, 93%, 94%, at least about 95%, 96%, 97%, at least about 98%, or at least about 99% amino acid identity to a polypeptide of SEQ ID NOS: 2, 34, 36, 38, 40, 42, 44, 46, 48, 50 and 52) that retain biological and/or immunogenic activity.

The presently described subject matter is directed to PilA polynucleotides of the presently described subject matter that may be inserted in a vector for amplification or expression. For expression, the polynucleotides are operatively linked to appropriate expression control sequences such as promoter and polyadenylation signal sequences. Further provided are host cells comprising polynucleotides of the presently described subject matter. Exemplary prokaryotic host cells can include bacteria such as E. coli, Bacillus, Streptomyces, Pseudonzonas, Salmonella, and Serratia. The presently described subject matter is directed to methods of producing the polypeptides of the presently described subject matter by growing the host cells and isolating polypeptide from the host cells or growth medium. Alternatively, polypeptides of the presently described subject matter can be prepared by chemical synthesis using standard means. Particularly convenient are solid phase techniques (see, e.g., Erikson et al., The Proteins (1976) v. 2, Academic Press, New York, p. 255). Automated solid phase synthesizers are commercially available. In addition, modifications in the sequence are easily made by substitution, addition or omission of appropriate residues. For example, a cysteine residue may be added at the carboxy terminus to provide a sulfhydryl group for convenient linkage to a carrier protein, or spacer elements, such as an additional glycine residue, may be incorporated into the sequence between the linking amino acid at the C-terminus and the remainder of the peptide.

The term "isolated" refers to a substance removed from, and essentially free of, the other components of the environment in which it naturally exists. For example, a polypeptide is separated from other cellular proteins or a DNA is separated from other DNA flanking it in a genome in which it naturally occurs.

Recombinant PilA protein (rPilA) may be generated to serve as a more readily renewable product. To do this, the published protocol of Keizer et al. (J. Biol. Chem., 276: 24186-14193, 2001), who studied a pilin which also had four Cys residues as it will be critical that rPilA similarly be properly folded so as to possess functional qualities of the native pilin subunit, is utilized. Briefly, a truncated pilin is engineered wherein the first 28 residues are removed from the N-terminus to prevent aggregation, and this truncated pilin will be further engineered to be transported to the periplasm by means of the incorporation of an OmpA leader sequence in the construct. Using this strategy Keizer et al. generated a recombinant soluble monomeric *P. aeruginosa* pilin protein that was able to bind to its receptor (asialo GM1) in in vitro assays and decrease morbidity and mortality in mice when the peptide was delivered 15 minutes prior to heterologous challenge. This soluble, monomeric, truncated form of NTHi PilA will be useful in the studies described herein.

The presently described subject matter also provides for synthetic chimeric proteins. The chimeric proteins may be synthesize, purified and sequenced using standard techniques. For example, the chimeric proteins may be assembled semi-manually by stepwise Fmoc-tert-butyl solid-phase synthesis and purified by HPLC. The composition and amino acid sequence of recombinant and synthetic chimeric proteins may be confirmed by amino acid analysis and/or mass spectral analysis.

Antibodies

The presently described subject matter provides antibodies which bind to antigenic epitopes of the chimeric proteins of the presently described subject matter. The antibodies may be polyclonal antibodies, monoclonal antibodies, antibody fragments which retain their ability to bind their unique epitope (e.g., Fv, Fab and F(ab)2 fragments), single chain antibodies and human or humanized antibodies. Antibodies may be generated by techniques standard in the art using chimeric protein(s) of the presently described subject matter or host cells expressing chimeric protein(s) of the presently described subject matter as antigens.

The presently described subject matter provides for antibodies specific for the chimeric proteins of the presently described subject matter and fragments thereof, which exhibit the ability to kill both *H. influenzae* bacteria and to protect humans from infection. The presently described subject matter also provides for antibodies specific for the chimeric proteins of the presently described subject matter which reduce the virulence, inhibit adherence, inhibit biofilm formation, inhibit twitching motility, inhibit cell division, and/or inhibit penetration into the epithelium of *H. influenzae* bacteria and/or enhance phagocytosis of the *H. influenzae* bacteria.

In vitro complement mediated bactericidal assay systems (Musher et al., Infect. In nun. 39: 297-304, 1983; Anderson et al., J. Clin. Invest. 51: 31-38, 1972) may be used to measure the bactericidal activity of anti-chimeric proteins antibodies.

It is also possible to confer short-term protection to a host by passive immunotherapy via the administration of preformed antibody against a chimeric protein of the presently described subject matter. Thus, antibodies of the presently described subject matter may be used in passive immunotherapy. Human immunoglobulin is preferred in human medicine because a heterologous immunoglobulin may provoke an immune response to its foreign immunogenic components. Such passive immunization can, for example, be used on an emergency basis for immediate protection of unimmunized individuals subject to special risks.

Antibodies of the presently described subject matter may be used in the production of anti-idiotypic antibody, which in turn can be used as an antigen to stimulate an immune response against the chimeric protein epitopes or *H. influenzae* epitopes.

Methods for Eliciting an Immune Response and Compositions Therefor

The presently described subject matter is directed to methods of eliciting in an individual an immune response to a bacteria. For example, the bacteria may be an NTHi bacteria, including, e,g., an *H. influenzae* bacteria. The bacteria may also be, e.g., a *Streptococcus pneumnoniae* and/or *Moraxella catarrhalis*, among others. *H. influenzae*. For example, the methods can elicit an immune response to the chimeric proteins of the presently described subject matter. These methods can elicit one or more immune responses, including but not limited to, immune responses which inhibit bacterial replication, immune responses which block *H. influenzae* adherence to cells, immune responses which prevent *H. influenzae* twitching, immune responses that kill *H. influenzae* bacteria and immune responses which prevent biofilm formation. The methods can comprise a step of topically administering an immunogenic dose of a composition comprising one or more chimeric proteins of the presently described subject matter. The methods can comprise topically administering an immunogenic dose of a composition comprising a cell expressing one or more chimeric proteins of the presently described subject matter. Further, the methods can comprise topically administering an immunogenic dose of a composition comprising one or more polynucleotides encoding one or more chimeric proteins of the presently described subject matter. The polynucleotide may be a naked polynucleotide not associated with any other nucleic acid or may be in a vector such as a plasmid or viral vector (e.g., adeno-associated virus vector or adenovirus vector). The methods may be used in combination in a single individual. The methods may be used prior or subsequent to *H. influenzae* infection of an individual. The methods and compositions of the presently described subject matter may be used to topically treat or prevent any pathological condition involving *H. influenzae* (typeable and nontypeable strains) such as OM, pneumonia, sinusitis, septicemia, endocarditis, epiglottitis, septic arthritis, meningitis, postpartum and neonatal infections, postpartum and neonatal sepsis, acute and chromic salpingitis, epiglottis, pericardis, cellulitis, osteomyelitis, endocarditis, cholecystitis, intraabdominal infections, urinary tract infection, mastoiditis, aortic graft infection, conjunctitivitis, Brazilian purpuric fever, occult bacteremia, and chronic obstructive pulmonary disease and exacerbation of underlying lung diseases such as chronic bronchitis, bronchietasis, and cystic fibrosis.

In methods of the presently described subject matter, a composition of the presently described subject matter can be topically administered as a priming dose followed by one or more topical booster doses. Proteins or polypeptides that beneficially enhance the immune response such as cytokines (e.g., IL-2, IL-12, GM-CSF), cytokine-inducing molecules (e.g. Leaf) or co-stimulatory molecules can be topically co-administered.

An "immunogenic dose" of a composition of the presently described subject matter is one that generates, after topical administration, a detectable humoral (antibody) and/or cellular (T cell) immune response in comparison to the immune response detectable before topical administration or in comparison to a standard immune response before topical administration. The immune response resulting from the presently described methods may be protective and/or therapeutic. The antibody and/or T cell immune response can protect the individual from *H. influenzae* infection, for example, infection of the middle ear and/or the nasopharynx or lower airway. In this use, the precise dose depends on the patient's state of health and weight, topical administration, the nature of the formulation, etc., but generally ranges from about 1.0 µg to about 5000 µg per 70 kilogram patient, more commonly from about 10 to about 500 µg per 70 kg of body weight.

Humoral immune response may be measured by many well known methods, such as Single Radial Immunodiffussion Assay (SRID), Enzyme Immunoassay (ETA) and Hemagglutination Inhibition Assay (HAI). In particular, SRID utilizes a layer of a gel, such as agarose, containing the immunogen being tested. A well is cut in the gel and the serum being tested is placed in the well. Diffusion of the antibody out into the gel leads to the formation of a precipitation ring whose area is proportional to the concentration of the antibody in the serum being tested. ETA, also known as ELISA (Enzyme Linked Immunoassay), is used to determine total antibodies in the sample. The immunogen is adsorbed to the surface of a microtiter plate. The test serum is exposed to the plate followed by an enzyme linked immunoglobulin, such as IgG. The enzyme activity adherent to the plate is quantified by any convenient means such as spectrophotometry and is proportional to the concentration of antibody directed against the immunogen present in the test sample. HAI utilizes the capability of an immunogen such as viral proteins to agglutinate chicken red blood cells (or the like). The assay detects neutralizing antibodies, i.e., those antibodies able to inhibit hemagglutination. Dilutions of the test serum are incubated with a standard concentration of immunogen, followed by the addition of the red blood cells. The presence of neutralizing antibodies will inhibit the agglutination of the red blood cells by the immunogen. Tests to measure cellular immune response include determination of delayed-type hypersensitivity or measuring the proliferative response of lymphocytes to target immunogen.

The presently described subject matter correspondingly provides topical compositions suitable for eliciting an immune response to chimeric proteins of the presently described subject matter. As noted above, the topical compositions can comprise one or more chimeric proteins, cells expressing one or more chimeric proteins, or one or more polynucleotides encoding one or more chimeric proteins. The topical compositions may also comprise one or more other ingredients such as pharmaceutically acceptable topical carriers and adjuvants.

In topical compositions of the presently described subject matter, a chimeric protein may be fused to another protein when produced by recombinant methods. For example, the other protein may not, by itself, elicit antibodies, but it may stabilize the first protein and forms a fusion protein retaining immunogenic activity. Further, the fusion protein can comprise another protein that is immunogenic, such as Glutathione-S-transferase (GST) or beta-galactosidase, relatively large co-proteins which solubilize the fusion protein and facilitate production and purification thereof. The other protein may act as an adjuvant in the sense of providing a generalized stimulation of the immune system. The other protein may be fused to either the amino or carboxy teminus of the chimeric proteins of the presently described subject matter.

In other topical compositions of the presently described subject matter, chimeric proteins may be otherwise linked to carrier substances. Any method of creating such linkages known in the art may be used. Linkages can be formed with hetero-bifunctional agents that generate a disulfide link at one functional group end and a peptide link at the other, such as a disulfide amide forming agent, e.g., N-succidimidyl-3-(2-pyridyldithio) proprionate (SPDP) (see, e.g., Jansen et al., Inimun. Rev. 62:185, 1982) and bifunctional coupling agents that form a thioether rather than a disulfide linkage such as reactive esters of 6-maleimidocaproic acid, 2-bromoacetic acid, 2-iodoacetic acid, 4-(N-maleimidomethyl) cyclohexane-1-carboxylic acid and the like, and coupling agent which activate carboxyl groups by combining them with succinimide or 1-hydroxy-2-nitro-4-sulfonic acid, for sodium salt such as succinimmidyl 4-(N-maleimido-methyl) cyclohexane-1-carobxylate (SMCC).

The present chimeric proteins may be formulated as neutral or salt forms. Pharmaceutically acceptable salts, include the acid addition salts (formed with the free amino groups of the peptide) and which are formed with inorganic acids such as, e.g., hydrochloric or phosphoric acids, or such organic acids as acetic, oxalic, tartaric, mandelic. Salts formed with the free carboxyl groups may also be derived from inorganic bases such as, e.g., sodium, potassium, ammonium, calcium, or ferric hydroxides, and such organic bases as isopropylamine, trimethylamine, 2-ethylamino ethanol, histidine, and procaine.

Topical compositions of the presently described subject matter may further comprise one or more adjuvants, including for example, known adjuvants. Known adjuvants include, for example, emulsions such as Freund's Adjuvants and other oil emulsions, Bordetella pertussis, MF59, purified saponin from Quillaja saponaria (QS21), aluminum salts such as hydroxide, phosphate and alum, calcium phosphate, (and other metal salts), gels such as aluminum hydroxide salts, mycobacterial products including muramyl dipeptides, solid materials, particles such as liposomes and virosomes. Examples of natural and bacterial products known to be used as adjuvants include monophosphoryl lipid A (MPL), RC-529 (synthetic MPL-like acylated monosaccharide), OM-174 which is a lipid A derivative from *E. coli*, holotoxins such as cholera toxin (CT) or one of its derivatives, pertussis toxin (PT) and heat-labile toxin (LT) of *E. coli* or one of its derivatives, and CpG oligonucleotides. Adjuvant activity can be affected by a number of factors, such as carrier effect, depot formation, altered lymphocyte recirculation, stimulation of T-25 lymphocytes, direct stimulation of B-lymphocytes and stimulation of macrophages.

Topical compositions of the presently described subject matter can be in any form suitable for topical delivery. Such formulations can be topically administered in combination with a flexible substrate. The active topically immunogenic ingredient can be encapsulated, for example, in the form of nanocapsules or microcapsules; can be mixed with excipients that are topically pharmaceutically acceptable and compatible with the active ingredient. Suitable excipients are, e.g., water, saline, dextrose, glycerol, or the like and combinations thereof. In addition, if desired, the topical vaccine may contain minor amounts of auxiliary substances such as wetting or emulsifying agents, pH buffering agents, or adjuvants, which can enhance the effectiveness of the topical vaccine. The topical vaccines are administered topically.

Topical formulations may include carriers, for example, polyalkalene glycols or triglycerides. Topical formulations may contain 10%-95% of active ingredient, or 25-70% of active ingredient.

Topical compositions may also be administered utilizing jet injectors, microneedles, electroporation, sonoporation, microencapsulation, polymers or liposomes, transmucosal routes and intranasal routes using nebulizers, aerosols and nasal sprays. Microencapsulation using natural or synthetic polymers such as starch, alginate and chitosan, D-poly L-lactate (PLA), D-poly DL-lactic-coglycolic microspheres, polycaprolactones, polyorthoesters, polyanhydrides and polyphosphazenes polyphosphatazanes are useful for both transdermal and transmucosal administration. Polymeric complexes comprising synthetic poly-omithate, poly-lysine and poly-arginine or amphipathic peptides are useful for transdermal delivery systems. In addition, due to their amphipathic nature, liposomes are contemplated for transdermal, transmucosal and intranasal vaccine delivery systems. Common lipids used for topical vaccine delivery include N-(1)2,3-(dioleyl-dihydroxypropyl)-N,N,N,-trimethylammonium-methyl sulfate (DOTAP), dioleyloxy-propyl trimethylammonium chloride DOTMA, dimystyloxpropyl-3-dimethyl-hydroxyethyl ammonium (DMRIE), dimethyldioctadecyl ammonium bromide (DDAB) and 9N(N',N-dimethylaminoethane) carbamoyl) cholesterol (DC-Chol). The combination of helper lipids and liposomes can enhance up-take of the liposomes through the skin. These helper lipids include dioleoyl phosphatidylethanolamine (DOPE), dilauroylphosphatidylethanolamine (DLPE), dimyristoyl phosphatidylethanolamine (DMPE), dipalmitoylphosphatidylethanolamine (DPPE). In addition, triterpenoid glycosides or saponins derived from the Chilean soap tree bark (Quillaja saponaria) and chitosan (deacetylated chitan) have been contemplated as useful adjuvants for intranasal and transmucosal topical vaccine delivery.

Topical formulations may be presented in unit-dose or multi-dose containers.

Methods of Inhibiting *H. influenzae*

The presently described subject matter also includes methods of inhibiting *H. influenzae* type IV pili function in an individual. The methods comprise topically administering to the individual, for example, one or more antibodies of the presently described subject matter and/or one or more chimeric proteins of the presently described subject matter; in an amount that inhibits function of the pili. In vitro assays may be used to demonstrate the ability to inhibit pili function. These methods can include, for example, methods using inhibitors of adherence mediated via type IV pili, inhibitors that disrupt existing biofilms mediated by type IV pili, and inhibitors of twitching.

Inhibition is contemplated for any pathological condition involving *H. influenzae*, for example, OM, pneumonia, sinusitis, septicemia, endocarditis, epiglottitis, septic arthritis, meningitis, postpartum and neonatal infections, postpartum and neonatal sepsis, acute and chromic salpingitis, epiglottis, pericardis, cellulitis, osteomyelitis, endocarditis, cholecystitis, intraabdominal infections, urinary tract infection, mastoiditis, aortic graft infection, conjunctitivitis, Brazilian purpuric fever, occult bacteremia, chronic obstructive pulmonary disease and exacerbation of underlying lung diseases such as chronic bronchitis, bronchietasis and cystic fibrosis.

Topical compositions comprising inhibitors of *H. influenzae* type IV pili function are provided. The topical compositions may comprise or consist of one of the foregoing active ingredients alone, may comprise combinations of the foregoing active ingredients or may comprise additional active ingredients used to treat bacterial infections. As discussed above, the topical compositions may comprise one or more additional ingredients such as pharmaceutically effective topical carriers. Also as discussed above, dosage and frequency of the topical administration of the topical compositions are determined by standard techniques and depend, for example, on the weight and age of the individual, area of topical administration, and the severity of symptoms. Topical administration of the pharmaceutical compositions may be, for example, by application to an area of skin, oral, buccal, nasal, rectal, intranasal, or vaginal.

Animal Model

Methods of the presently described subject matter may be demonstrated in a chinchilla model widely accepted as an experimental model for OM. In particular, a chinchilla model of NTHi-induced OM has been well characterized (Bakaletz et al., J Infect. Dis., 168: 865-872, 1993; Bakaletz and Holmes, Clin. Diagn. Lab. Immunol., 4: 223-225, 1997; Suzuki and Bakaletz, Infect. Imnzun., 62: 1710-1718, 1994; Mason et al., Infect. Immun., 71:3454-3462, 2003), and has been used to determine the protective efficacy of several NTHi outer membrane proteins, combinations of outer membrane proteins, chimeric synthetic peptide vaccine components, and adjuvant formulations against OM (Bakaletz et al., Vaccine, 15: 955-961, 1997; Bakaletz et al., Infect. Immun., 67: 2746-2762, 1999; Kennedy et al., Infect. IMMUII 68: 2756-2765, 2000; Kyd et al., Infect. Immun., 66:2272-2278, 2003; Novotny and Bakaletz, J. Immunol., 171, 19781983, 2003).

In the model, adenovirus predisposes chinchillas to *H. infiuenzae*-induced OM media, which allowed for the establishment of relevant cell, tissue and organ culture systems for the biological assessment of NTHi (Bakaletz et al., J Infect. Dis., 168: 865-72, 1993; Suzuki et al., Infect. Immunity 62: 1710-8, 1994). Adenovirus infection alone has been used to assess the transudation of induced serum antibodies into the tympanum (Bakaletz et al., Clin. Diagnostic Lab Immunol., 4(2): 223-5, 1997) and has been used as a co-pathogen with NTHi, to determine the protective efficacy of several active and passive immunization regimens targeting various NTHi outer membrane proteins, combinations of OMPs, chimeric synthetic peptide vaccine components, and adjuvant formulations as vaccinogens against otitis media (Bakaletz et al., Infect Immunity, 67(6): 2746-62, 1999; Kennedy et al., Infect. Immun., 68(5): 2756-65, 2000; Novotny et al., Infect Immunity 68(4): 2119-28, 2000; Poolman et al., Vaccine 19 (Suppl. 1): S108-15, 2000).

EXAMPLES

Example 1

Kinetic Analysis and Evaluation of the Mechanisms Involved in the Resolution of Experimental Nontypeable *Haemophilus influenza* ("NTHi")-Induced Otitis Media after Transcutaneous Immunization ("TCI")

The mechanisms for the observed rapid resolution of established NTHi-induced OM after TCI with chimV4+ dmLT in a chinchilla model (of nontypeable *Haemophilus influenzae* (NTHi)-induced otitis media) ("OM")) were analyzed. The kinetics of disease resolution were assessed over a period of 14 days via multiple parameters. Video otoscopy and tympanometry were performed as clinically-relevant evaluations of the incidence and severity of OM in addition to examination of mucosal biofilms within the middle ear to rank disease severity grossly. Culture of NTHi from middle ear fluids and mucosal biofilms provided an assessment of the bacterial load within both the planktonic and adherent populations, respectively, over time. The quantity of immunogen-specific antibody in middle ear fluids was determined to identify the point at which an adaptive immune response contributed to disease resolution. Moreover, as it became apparent that innate immune elements within the middle ear mucosa played a role early in this disease resolution process, the relative amount of the host defense molecule chinchilla 3-defensin-1 (cBD-1, an orthologue of human 3-defensin 3), was examined. Lastly, the functional activation of dermal DCs induced by TCI of chinchilla pinnae and the phenotype of the resultant CD4+ T-cell response was analyzed. Collectively, these data supported a proposed model wherein TCI with a chimeric immunogen directed against two critical NTHi adhesions and delivered with a potent adjuvant stimulated the activation and migration of dermal DCs to the NALT, the expansion and differentiation of CD4+ T-cells to a polyfunctional phenotype and subsequent production of specific antibody to facilitate the eradication of NTHi from the middle ear and resolution of both established mucosal biofilms resident within the middle ear and active disease.

A. Materials and Methods

A (i) Animals

Sixty-one adult chinchillas (Chinchilla lanigera; Rauscher's Chinchilla Ranch, LaRue, Ohio; mean mass 550±12 g) with no evidence of middle ear disease as determined by video otoscopy (MedRx, Largo, Fla.) and tympanometry (EarScan, Murphy, N.C.) were enrolled and divided into 3 cohorts of 20-21 chinchillas each. Animal care and all procedures were performed in concordance with institutional and federal guidelines, and were conducted under an approved protocol.

A (ii) Immunogen and Adjuvant chimV4 is a novel, chimeric immunogen wherein a modified and N-terminally truncated form of PilA, the majority subunit of Tfp, serves as an immunogenic carrier for 24 amino acids of a B-cell epitope from surface-exposed region 3 of OMP P5. A double mutant form of E. coli heat-labile enterotoxin, called LT(R192G-L211A) and abbreviated 'dmLT', wherein glycine is substituted for arginine at position 192 and alanine is substituted for lysine at position 211, served as the adjuvant. The amino acid substitutions render dmLT nontoxic while maintaining adjuvant properties.

A (iii) Bacterial Strain

NTHi strain 86-028NP was isolated from the nasopharynx of a child undergoing tympanostomy and tube insertion for chronic OM at Nationwide Children's Hospital, Columbus, Ohio. This strain has been characterized and extensively used in chinchilla models of OM, a rat model of pulmonary clearance and a murine model of OM.

A (iv) NTHi Challenge and Transcutaneous Immunization Regimen

Chinchillas were challenged with NTHi exclusively transbullarly with 1000 CFU strain 86-028NP delivered in 0.3 ml sterile, pyrogen-free 0.9% sodium chloride (Hospira, Inc., Lake Forest, Ill.) per bulla and the challenge dose was confirmed by plate count. This challenge model has been shown to result in the formation of a mucosal biofilm in >83% of middle ears within four days. Four days after challenge (day 0), all animals were immunized by TCI. The pinnae of alert animals was first hydrated by placement of gauze soaked in sterile, pyrogen-free 0.9% sodium chloride on the inner surface for 5 min. Pinnae were then blotted with dry gauze and 50 μl of each vaccine formulation was applied to the center of the inner face of each pinna using a pipet. The pinnae were then folded in half and opposing surfaces gently rubbed together. Formulations consisted of 10 μg chimV4 admixed with 10 μg dmLT, 10 μg dmLT alone or 50 μl pyrogen-free 0.9% sodium chloride and were delivered twice at a weekly interval (day 0 and day 7).

A (v) Otoscopy and Tympanometry

Video otoscopy using a 0-degree, 3-in. probe connected to a digital camera system (MedRx, Largo, Fla.) was utilized to monitor signs of tympanic membrane inflammation and/or presence of fluid within the middle ear space. Middle ear pressure, tympanic membrane compliance and tympanic width were monitored via tympanometry using a MADSEN OTOflex 100 (GN Otometrics, Schaumburg, Ill.). Overall signs of OM were blindly rated on a scale of 0 to 4+. Middle ears with a score of ≥2.0 were consistently considered positive for otitis media as middle ear fluid (MEF) was visible behind the tympanic membrane. Each middle ear was considered independent (n=4 middle ears per cohort on day 0, n=6 middle ears per cohort for days 3-14), and for each cohort, the percentage of middle ears with OM was calculated.

A (vi) Collection of Samples

On days 0, 3, 5, 7, 9, 11 and 14 after primary TCI, three chinchillas from each cohort were sacrificed. MEF was collected by epitympanic tap, serially diluted and plated on to chocolate agar to semi-quantitate CFU planktonic NTHi. Fluid from each middle ear was considered independent (n=4 middle ears per cohort on day 0, n=6 middle ears per cohort for days 3-14), and for each cohort, the mean CFU NTHi/ml middle ear fluid±SEM was presented. Middle ear mucosal biofilm, if present, was collected after evaluation as described below, homogenized and plated on to chocolate agar to semi-quantitate the CFU NTHi adherent to the middle ear mucosa. Each middle ear was considered independent (n=4 middle ears per cohort on day 0, n=6 middle ears per cohort for days 3-14) and for the cohort, the mean CFU NTHi/mg tissue±SEM was presented.

A (vii) Evaluation of Mucosal Biofilms within the Middle Ear

Upon sacrifice, the inferior bullae from each animal were dissected, opened to reveal the middle ear space and washed with 1.0 ml sterile, pyrogen-free 0.9% sodium chloride to remove residual MEF and loosely adherent bacterial biofilm. The bullae and remaining adherent mucosal biofilm were then imaged with a digital camera. Each image was blindly ranked on the relative amount of residual mucosal biofilm using a 0-4+ scale, wherein 0=no mucosal biofilm; 1=mucosal biofilm fills<25% of middle ear space; 2=mucosal biofilm fills 25-50% of middle ear space; 3=mucosal biofilm fills 50-75% of middle ear space and 4=mucosal biofilm fills 75-100% of middle ear space. The mean mucosal biofilm score±SEM for the cohort (n=4 middle ears per cohort on day 0, n=6 middle ears per cohort for days 3-14) was reported.

A (viii) Enzyme-Linked Immunosorbent Assays

To determine the relative quantity of immunogen-specific IgG and IgA in clarified, pooled MEFs, endpoint ELISA was performed. Samples were incubated in chimV4-coated wells (0.2 g protein/well) for 3 h at 25° C. and bound antibody was detected with HRP-conjugated goat anti-rat IgG or IgA (Bethyl Laboratories, Montgomery, Tex.). Color was developed with 3,3',5,5'-tetramethylbenzidine (TMB; Pierce Biotechnology, Rockford, Ill.). Endpoint reciprocal titers were defined as the dilution that yielded an $OD_{450\ nm}$ value of 0.1 above control wells that were incubated without sample fluids. Assays were performed a minimum of three times and reciprocal titers reported as the geometric mean (GMT) with 95% confidence intervals.

To quantitate the host defense peptide cBD-1 within mucosal homogenates collected on day 3, a sandwich ELISA was performed. Clarified homogenates of middle ear mucosa and mucosal biofilm were incubated in wells of a Microfluor 2 black U-bottom microtiter plate (Thermo Scientific, Rochester, N.Y.) coated with Protein G-purified rabbit anti-recombinant cBD-1 (0.5 g antibody/well) overnight at 4° C. Host defense peptide was detected by addition of FITC-conjugated purified rabbit anti-recombinant cBD-1. The concentration of cBD-1 in each mucosal sample was calculated by comparison of the mean fluorescence of each well versus a standard curve generated with purified recombinant cBD-1. The mean concentration of cBD-1±SEM for each cohort from three independent assays is reported.

A (ix) Functional Responses of Dermal DCs after TCI

To evaluate functional responses of cutaneous DCs induced by TCI, the efflux of dermal DCs from the chinchilla pinnae and secretion of immune effectors was examined. Three hours after TCI with chimV4 admixed with 10 μg dmLT, 10 examined g dmLT alone, or sterile, pyrogen-free 0.9% sodium chloride, three chinchillas per formulation were sacrificed and both pinnae removed, placed in 70% v/v ethanol for 5 min. and transferred to sterile petri dishes to dry. The pinnae were trimmed to 2.5 $cm^2$, the dorsal and ventral faces peeled apart, cartilage removed and the pinnae placed on to 8 μm pore size Transwell membranes. Two milliliters of RPMI 1640 (Corning cellgro, Manassas, Va.) plus 0.5% (w/v) bovine serum albumin (Sigma Aldrich) were added to the basolateral chamber and incubated for 20 h at 37° C., 5% $CO_2$, in a humidified atmosphere. Cells that had migrated into the basolateral chamber were separated based on expression of CD11c$^+$ using MACS magnetic microbeads (Miltenyi Biotech, Cambridge, Mass.) then incubated with antibody directed against CD11b (eBiosciences, Inc., San Diego, Calif.) and DC-SIGN (R&D Systems, Minneapolis, Minn.) for discrimination of dermal DCs. The number of dermal DC per ml culture medium was determined as the number of events detected within a 25 μl volume using a calibrated Accuri C6 flow cytometer (BD Biosciences, Sparks, Md.). Each pinna was considered independent and the mean±SEM for each cohort presented (N=6 pinnae per cohort).

The clarified supernatants from each of the six cultured pinnae per cohort described above were applied to Proteome profiler human cytokine array kit (R&D Systems) and assayed following the manufacturer's instructions. Relative pixel intensity was determined with a BioRad GS800 densitometer and analyzed with Quantity One software (Bio-Rad, Hercules, Calif.). The fold increase in pixel intensity between pinnae collected from chinchillas administered dmLT alone or chimV4+ dmLT was compared to pinnae administered saline.

A (x) Determination of T-Cell Phenotype

It has been shown that dendritic cells migrate to the NALT after TCI of the chinchilla pinnae, indicating that this lymphoid aggregate may serve as an immune inductive site. To examine the phenotype of the immune response induced following TCI, cytokine production by CD4$^+$ T-cells within the NALT was examined. One week after receipt of the second immunizing dose as described above, the NALT was collected from three chinchillas per cohort; homogenized individually using GentleMACS dissociator (Miltenyi Biotech) and CD3$^+$ cells isolated using MACS magnetic microbeads. A total of $1\times10^6$ cells/0.5 ml RPMi 1640 plus 0.5% (w/v) bovine serum albumin was incubated with Leukocyte activation cocktail plus GolgiPlug (BD Biosciences) for 5 h at 37° C., 5% $CO_2$ in a humidified atmosphere prior to stain with human Th1/Th2/Th17 phenotyping kit according to manufacturer's instructions (BD Biosciences). 20,000 CD4$^+$ lymphocytes were acquired using an Accuri C6 flow cytometer and data analyzed with FloJo software (Tree Star, Inc., Ashland, Oreg.). One of three representative assays is presented.

A (xi) Statistical Analyses

Data analyses were performed using GraphPad Prism v. 5.01 (La Jolla, Calif.). Statistical differences among cohorts in bacterial concentration within MEFs and mucosal biofilms, antibody titers and dendritic cell migration were determined using Kruskal-Wallis one-way analysis of variance on ranks and Dunn's method for multiple comparisons. A p-value of ≤0.05 was considered significant. Significant differences in the percentage of middle ears with OM and differences among mucosal biofilm scores were analyzed by repeated measures analysis of variance and Bonferroni's multiple comparison test. A p-value of 0.05 was considered significant.

B. Results

B (i) Resolution of Established Experimental Otitis Media

As a clinically-relevant assessment for the resolution of established experimental OM, each tympanic membrane was examined to document signs of disease including erythema, the presence of middle ear fluid behind the tympanic membrane and changes in tympanometric read outs. As expected, on day 0, 100% of middle ears (122/122) were positive for the presence of MEF behind the tympanic membrane as each middle ear had been directly inoculated with NTHi four days prior (FIG. 1). Within three days after receipt of the first immunizing dose, a 33% (2/6 middle ears) reduction in OM was observed after receipt of the adjuvant dmLT alone; however, within seven days after administration of the primary dose, the percentage of animals with OM increased to 100% (6/6 middle ears). The reduction in the incidence of OM after receipt of dmLT showed that an initial, non-specific immune response was induced following administration of this potent adjuvant, a trend observed again after receipt of the second immunizing dose on day 7. Delivery of chimV4 admixed with dmLT resulted in a greater reduction in the percentage of middle ears with OM to 50% (3/6 middle ears) three and five days after receipt of the first dose, statistically significant results compared to receipt of saline (p<0.05). Moreover, seven days after primary TCI with chimV4 admixed with dmLT only 17% (116 middle ears) demonstrated signs on OM and although this percentage increased to 33% (2/6 middle ears) on day nine, receipt of the second immunizing dose subsequently induced rapid and complete resolution of experimental disease. On each day after receipt of the second immunizing dose, significantly fewer middle ears in the cohort that received chimV4+ dmLT exhibited signs of experimental OM, compared to either cohort that received saline or dmLT alone (p<0.05). These results indicated that incorporation of chimV4 with dmLT facilitated an enhanced and NTHi-targeted immune response. Moreover, these data demonstrated that delivery of chimV4+ dmLT induced an immune response in which clinically-relevant signs of OM were abrogated by 50% within three days after administration and experimental disease had resolved within 14 days.

B (ii) Eradication of from Middle Ear Fluids

To examine clearance of planktonic NTHi after TCI, MEFs were collected when their presence was indicated by video otoscopy and cultured to determine the relative concentration of bacteria within these fluids. On day 0, four days after direct challenge of middle ears with 1000 CFU NTHi, and prior to administration of any vaccine formulation, the inoculum had multiplied to $9.7\times10^6$ to $1.1\times10^7$ CFU/ml in all animals (FIG. 2), as is expected in this challenge model.

Figure 2:
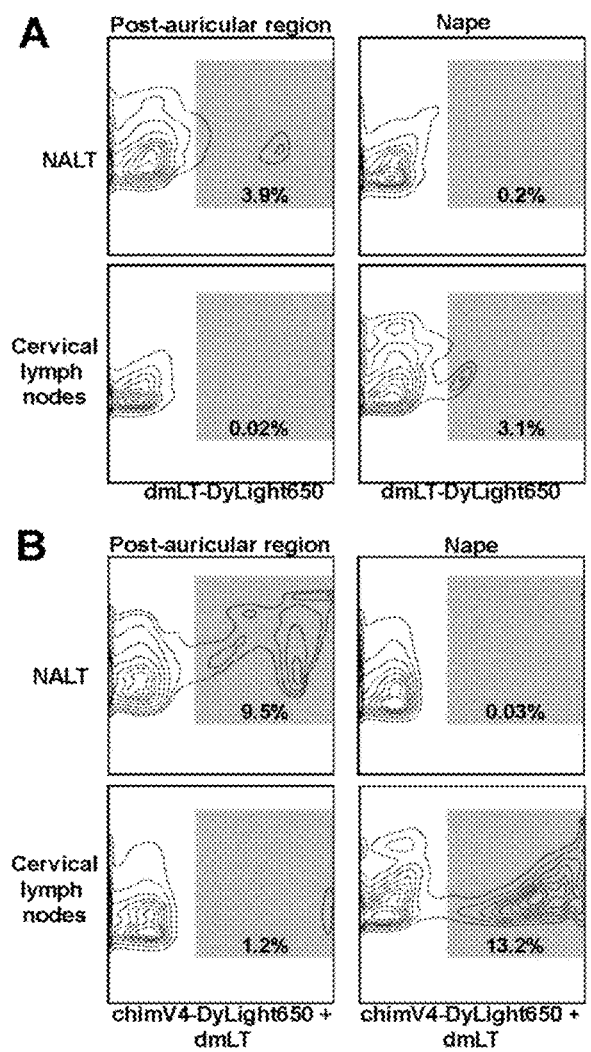
FIG. 2. is a graphical representation of eradication of from middle ear fluids. NTHi was inoculated into the middle ears of all chinchillas four days prior to primary immunization (inoc). Mean CFU per middle ear fluid±SEM for each cohort is presented. Boxes around days 0 and 7 on x-axis indicate days of vaccination. *$p<0.05$ compared to receipt of saline; +$p<0.05$ compared to receipt of dmLT alone. N=4 middle ears per cohort on day 0; N=6 middle ears per cohort on days 3-14.

No significant difference in bacterial concentration was observed among the three cohorts until one week after receipt of the primary immunizing dose. Whereas beginning on day 3 a significant 50% reduction in middle ears with signs of OM in the cohort that received chimV4+ dmLT was detected by video otoscopy and tympanometry (see FIG. 1), the bacterial concentration within the MEFs of chinchillas observed to have OM ranged from $2.4 \times 10^7$ to $5.0 \times 10^7$ CFU/ml and did not allow for statistical discrimination from the cohorts administered saline or dmLT only ($1.0 \times 10^7$ to $5.3 \times 10^7$ CFU/ml). However, as shown in FIG. 2, beginning seven days after primary TCI, and specifically upon receipt of the second immunizing dose, a rapid and significant 6-log reduction in NTHi concentration within middle ear fluids of animals administered chimV4+ dmLT was observed, compared to receipt of saline or dmLT alone ($p<0.05$), with complete eradication of NTHi from the middle ears of animals in this cohort by day 14. These data demonstrated that TCI with chimV4+ dmLT induced an immune response that effectively contributed to the elimination of planktonic NTHi within middle ear fluids, a response that was most effective after administration of the boosting dose.

Figure 3:
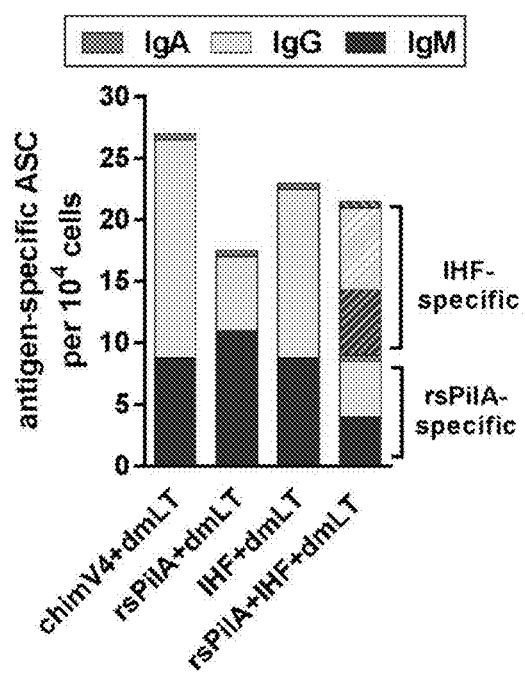
FIG. 3 is a graphical representation of resolution of established mucosal biofilms from within the middle ear. Mean mucosal biofilm scores±SEM for each cohort were based on a 0-4+ scale of relative residual mucosal biofilm. Boxes around days 0 and 7 on x-axis indicate days of vaccination. *$p<0.01$ compared to receipt of saline; +$p<0.01$ compared to receipt of dmLT alone. N=4 middle ears per cohort on day 0; N=6 middle ears per cohort on days 3-14.

B (iii) Resolution of Established Mucosal Biofilms from the Middle Ear after Direct Challenge To evaluate the kinetics of mucosal biofilm resolution afforded by TCI, the middle ears of all chinchillas were inoculated with and a robust biofilm allowed to form. In this model, >83% of middle ears develop a mucosal biofilm that fills 75-100% of the middle ear space within four days. Following immunization, any residual biofilm was evaluated and ranked on a 0 to 4+ scale wherein a score of 0 indicated that no mucosal biofilm was present and 4+ designated that 75-100% of the middle ear space contained an mucosal biofilm. As shown in FIG. 3, on day 0 (four days after direct challenge of the middle ear), the mean mucosal biofilm scores for each of the three cohorts ranged from 3.7 to 4.0, which indicated that 75-100% of the middle ear space of all animals contained a mucosal biofilm, as expected for this model. No change in rank was observed in the cohort that received saline, as a mean score of ≥3.0 was maintained for the duration of the study. Receipt of dmLT alone, however, afforded a 25% reduction in mucosal biofilm with scores of 2.3-2.8 detected after receipt of the second dose. These data provided additional evidence to support the induction of a nonspecific immune response by this powerful adjuvant.

Notably, administration of chimV4 with dmLT resulted in a statistically significant reduction in mucosal biofilm from the middle ear five days after primary ICI, compared to receipt of saline ($p<0.01$). At this time point, the mean biofilm score equaled 2.3±0.2 and indicated that approximately 50% of the middle ear space contained a mucosal biofilm. Over time, biofilm scores for this cohort consistently decreased; seven days after primary TCI, a rank of 1.7±0.2 was achieved (25-50% of the middle ear space had a mucosal biofilm) and by day 14, 75% of the biofilm was eliminated ($p<0.01$ compared to saline and dmLT cohorts). These data demonstrated that ICI with chimV4+ dmLT was effective to stimulate the resolution of an established mucosal biofilm from the middle ear.

B (iv) Eradication of NTHi from Established Mucosal Biofilms in the Middle Ear

Figure 4:
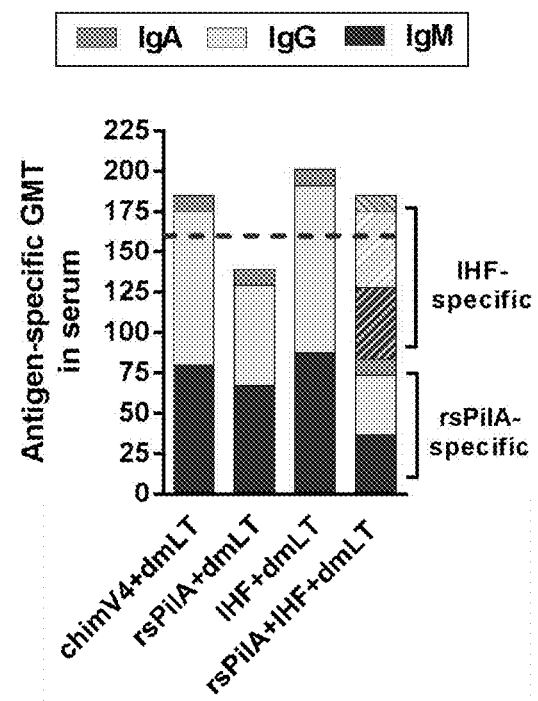
FIG. 4 is a graphical representation of relative concentration of adherent to middle ear mucosa. Mean CFU±SEM within biofilm that remained adherent to the middle ear mucosa over time is presented. Boxes around days 0 and 7 on x-axis indicate days of vaccination. *$p<0.05$ compared to receipt of saline; +$p<0.05$ compared to receipt of dmLT alone. N=4 middle ears per cohort on day 0; N=6 middle ears per cohort on days 3-14.

To examine the relative concentration of NTHi resident within a biofilm adherent to the mucosa in the middle ear, compared to the planktonic population available for culture from MEFs as described in FIG. 2, the middle ear mucosa and accompanying NTHi biofilm was collected, homogenized and cultured. Four days after direct inoculation of the middle ear, the mean bacterial concentration of NTHi was equivalent among the three cohorts as expected and ranged from $5.3 \times 10^3$ to $1.8 \times 10^4$ CFU NTHi/mg mucosa (FIG. 4). Within three days after primary ICI, significantly fewer NTHi were detected in mucosal homogenates from animals administered either dmLT alone or chimV4+ dmLT ($8.5 \times 10^2$ and $1.5 \times 10^3$ CFU/mg mucosa, respectively), compared to saline ($3.5 \times 10^4$ CFU; $p<0.05$). Moreover, the latter cohorts exhibited a 10-fold reduction in CFU NTHi relative to three days prior, influenced by administration of dmLT, as the two cohorts that received this adjuvant were distinct from the cohort administered saline, yet not significant from each other. Furthermore, this result could not be attributed to development of adaptive immune response, as only three days had passed since primary immunization and no immunogen-specific antibody was yet detectable within MEFs, as described below. Over the following four days, the cohort that received dmLT alone maintained a bacterial concentration of $1.5$-$1.8 \times 10^3$ CFU NTHi/mg mucosa, however middle ears from chinchillas immunized with chimV4+ dmLT exhibited a sequential 11- and 24-fold reduction in CFU on days 5 and 7 after primary ICI, respectively ($p<0.05$ compared to animals administered saline on days 5 and 7; $p<0.05$ compared to animals administered dmLT alone on day 7 only). Moreover, within the latter 7 days of the study, only 10-30 CFU NTHi/mg tissue were detected ($p<0.05$ compared to receipt of saline; $p<0.05$ compared to receipt of dmLT alone on day 14 only). Thus, while ICI with dmLT alone appeared to stimulate an initial reduction in CFU NTHi within mucosal biofilms in the middle ear, the combined influence of chimV4+ dmLT yielded consistently fewer NTHi at each subsequent time point.

B (v) Analysis of Immunogen-Specific Antibody and cBD-1 in MEFs

To begin to examine the mechanisms for the protective efficacy observed, the relative quantity of immunogen-specific IgG and IgA within MEFs was examined by ELISA. chimV4-specific IgG within MEFs collected from animals immunized with chimV4+ dmLT was detected at levels above background beginning 5 days after primary TCI (GMT=80; Table 1). Whereas a slight, but non-significant decrease in titer was observed on day 7, receipt of the second immunizing dose induced a 2.5-fold increase in specific IgG to a GMT of 160, which was maintained for an additional two days ($p<0.05$ compared to day 0). By day 14, seven days after receipt of the second immunizing dose, the GMT of chimV4-specific IgG in the middle ear equaled 190 ($p<0.05$ compared to day 0). Whereas chimV4-specific IgA was also detected within MEFs beginning five days after primary TCI, the relative quantity of this antibody isotype was 2.0-4.6-fold less than IgG at each time point tested and no significant increase in quantity of IgA was achieved relative to pre-immunization values (Table 2). The ability to eradicate NTHi from the middle ear was associated with a GMT value of at least 160 for IgG. Review of the kinetics of NTHi clearance from the MEF of chinchillas immunized with chimV4+ dmLT (FIG. 2) further supports this observation as on days 9-14, time points at which the GMT of chimV4-specific IgG≥160, significantly fewer NTHi were present within MEFs and a >5-log decrease in CFU was achieved.

TABLE 2

| Days | chimV4-specific IgG | chimV4-specific IgA |
|---|---|---|
| 0 (primary TCI) | 10 | 10 |
| 3 | 10 | 10 |
| 5 | 80 | 28 (15-53) |

TABLE 2-continued

| Days | chimV4-specific IgG | chimV4-specific IgA |
|---|---|---|
| 7 (boost) | 65 (24-171) | 32 (12-86) |
| 9 | 160* (56-459) | 35 (17-72) |
| 11 | 160* (65-394) | 50 (28-91) |
| 14 | 190* (66-546) | 56 (30-107) |

*$p < 0.05$ compared to day 0.

Geometric mean of the reciprocal titer for chimV4-specific IgG and IgA within MEFs collected from chinchillas immunized by TCI with chimV4+ dmLT. 95% confidence intervals of the geometric mean are indicated in brackets. N=4 middle ears for day 0, N=6 middle ears for days 3 to 14.

As reduction of established NTHi mucosal biofilms began within three days after primary TCI (FIG. 4) and prior to detection of antibody in MEFs (Table 1), it was hypothesized that production of innate host defense molecules by the middle ear epithelium contributed to this observation. One of many such effectors, cBD-1, the orthologue to human 3-defensin3, known to be expressed in the chinchilla uppermost respiratory tract that exhibits bactericidal activity against NTHi in vitro and shown to have a role in the control of NTHi during experimental colonization of the chinchilla nasopharynx. Three days after primary immunization (seven days after NTHi challenge), 50.3±16.7 ng cBD-1/ml was detected within homogenates of middle ear mucosa collected from animals that received saline, compared to 643.4±57.3 ng/ml and 849.8±49.0 ng/ml in mucosae from animals administered dmLT only or chimV4+ dmLT, respectively. These data show that the reduced bacterial concentration detected within mucosal biofilms adherent to the middle ear mucosa of animals immunized with dmLT alone and chimV4+ dmLT can be attributed to significantly more cBD-1 present within this milieu, compared to the cohort that received saline ($p<0.05$).

B (vi) Activation of Dermal DCs

As a means to examine the functional activation of dermal DCs after ICI, pinnae were collected 3 h after immunization and cultured ex vivo. At this arbitrarily selected time point, $1.5 \times 10^3$ CD11c$^+$CD11 b$^+$DC-SIGN$^+$ dermal DC/ml had emigrated from the pinnae into the culture medium, a value which can be considered as steady-state migration in this assay system. TCI with dmLT alone resulted in 12-times more dermal DCs ($1.9 \times 10^4$ cells/ml), although not a significant result. The greatest and significant efflux of dermal DCs was observed from pinnae on which chimV4+ dmLT was applied; a total of $6.8 \times 10^4$ cells/ml was observed, 44-and 4-fold more cells compared to application of saline or dmLT alone, respectively ($p<0.01$).

Figure 5:
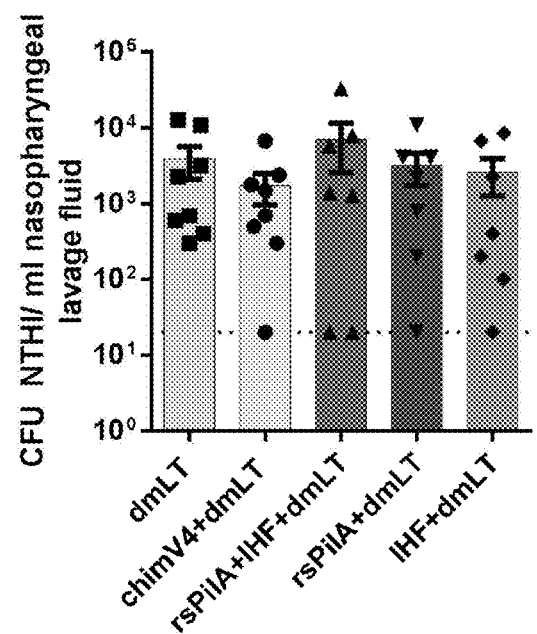
FIG. 5 is a graphical representation of secretion of cytokines and chemokines by dermal DCs activated by ICI. Supernatants collected from cultured chinchilla pinnae from which dermal DCs had emigrated were assessed for the production of inflammatory mediators by membrane array. The fold change in pixel intensity as determined by densitometry relative to the saline-treated pinnae is shown. N=6 pinnae for each cohort.

Activated DCs can secrete cytokines and chemokines as a means of functional modulation via autocrine or paracrine manner. The supernatants from the cultured pinnae were assayed for the presence of inflammatory mediators via membrane array. Of a panel of 36 effectors, seven were expressed at least 2-fold greater after TCI of pinnae with dmLT or chimV4+ dmLT compared to administration of saline (FIG. 5). Of note is the 10-and 5-fold increase in CCL4 induced by TCI with chimV4+ dmLT, compared to saline or dmLT alone, respectively. While many of the listed mediators are pluripotent and are involved in the induction of inflammatory responses, a majority of these factors share a common role as chemotactic agents for specific cell types. IL-23, IL-16, CCL5 and CCL4 in particular, are noted to induce the migration and differentiation of CD4+ T-cells, critical first steps toward the initiation of an immune response.

B (vii) Induction of Polyfunctional CD4+ T-Cells

Figure 6:
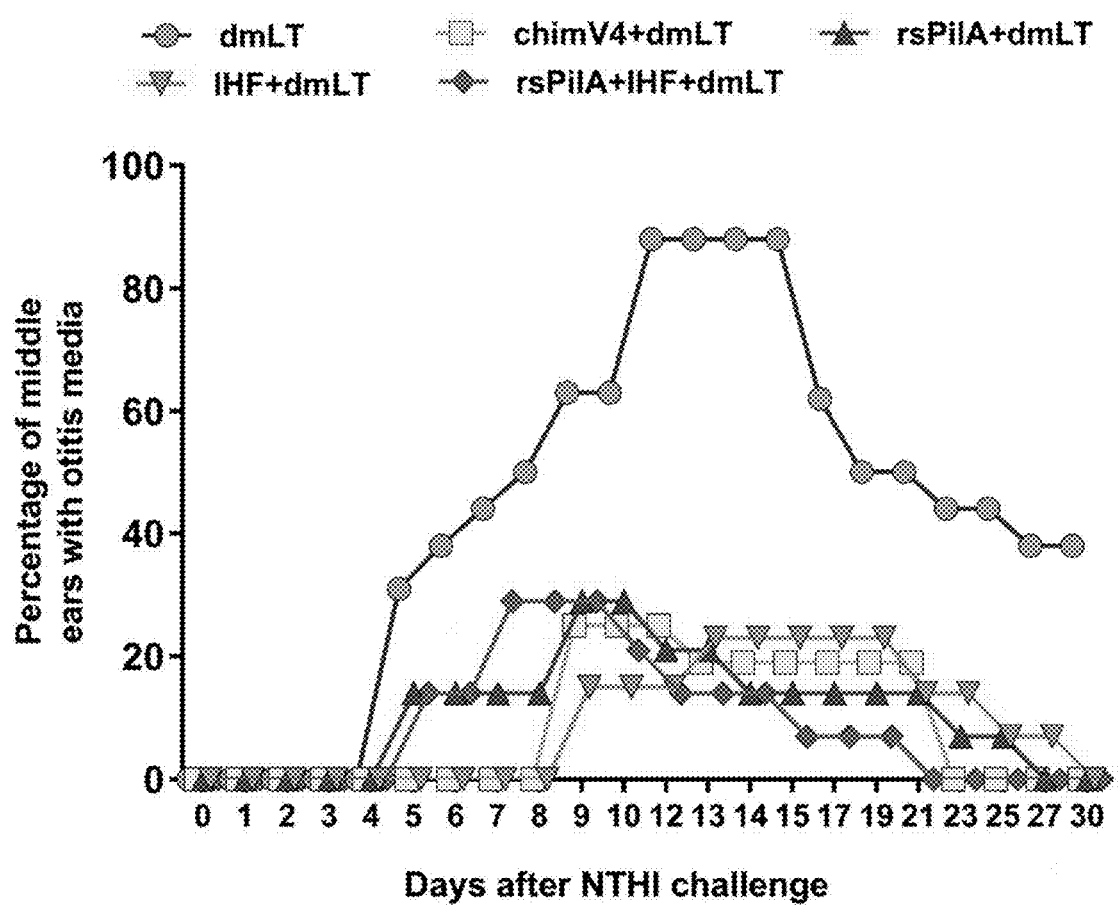
FIG. 6 is a graphical representation of induction of polyfunctional $CD4^+$ T-cells within the chinchilla NALT after ICI. One week after receipt of the second immunizing dose, the NALT from each chinchilla was collected and processed to examine intracellular cytokine production by $CD4^+$ T-cells in order to discern Th phenotype. The shaded region in each density plot indicates the positive staining for IFN-γ-and IL-17-producing $CD4^+$ T-cells, relative to isotype antibody controls. One of three representative plots is presented for each cohort.

The phenotype of the resultant immune response, specifically, the pattern of cytokine production by CD4+ T-cells within the NALT after TCI with any of the three vaccine formulations, was examined. The NALT was examined as the primary lymphoid aggregate to which dermal DCs trafficked after TCI in this model. Compared to the NALT isolated from chinchillas to which saline was applied, TCI with dmLT alone yielded 5.1% of CD4+ T-cells that produced both IFN-γ and IL-17 (FIG. 6), further support for the induction of a modest response by administration of this potent adjuvant alone. ChimV4 admixed with dmLT resulted in a 5.7-fold increase in the percentage of T-cells that produced both IFN-γ and IL-17—(29.3%), relative to receipt of dmLT alone. Moreover, within the positive population highlighted, two subtypes were observed; one of lesser dual fluorescence and one of greater dual fluorescence. Each population may represent CD4+ T-cells of greater and lesser activation states.

The greater percentage of CD4+ T-cells observed within the NALT of animals immunized by ICI with chimV4+ dmLT, compared to receipt of dmLT or saline alone, indicated that this immunization regime induced the greatest expansion of CD4+ T-cells resident within this lymphoid aggregate of the three formulations. Moreover, increase in the number of cells that expressed both IFN-y and IL-17, represented by the greater overall fluorescent signal within this population, demonstrated robust differentiation to cells that appeared functionally polarized toward a dual Th1-Th17 phenotype. These polyfunctional T-cells have the potential to further facilitate the development of a broadly protective and multifactorial immune response that could be highly efficacious against-induced experimental OM, an outcome which was observed herein.

C. Discussion

OM is a common disease of childhood and while the associated mortality is very limited at least in developed countries, the morbidity associated with this disease in terms of developmental delays, quality of life and economic impact is substantial. The chronic nature of OM may be attributed to the ability of the bacterial causative agents, including NTHi, to form mucosal biofilms within the middle ear space. These highly structured communities are recalcitrant to antibiotic therapies and resist immune-mediated clearance. Among many other proteins, and an abundance of host- and bacterial-derived extra-cellular DNA, NTHi OMP P5 and Tfp are identified as components of the biofilm matrix. TCI with chimV4, a chimeric immunogen designed to target both of these critical NTHi adhesions (outer membrane protein P5 and Tfp), delivered with dmLT by simply rubbing the formulations on to the pinnae of chinchillas was significantly efficacious to both prevent NTHi-induced OM and resolve active OM. The rapidity with which biofilms that had been established within the middle ear resolved was striking. TCI with NTHi adhesin-directed immunogens plus dmLT induced the activation and subsequent migration of cutaneous DCs to the NALT, which is located in close proximity to the site of experimental disease, and thereby facilitated the efficacy observed.

The mechanisms that afforded the observed efficacy and examine the kinetics of disease resolution were examined utilizing an established chinchilla model wherein cohorts of animals were first challenged by direct inoculation of the middle ear with NTHi to induce OM. The chinchilla serves as a relevant model for this pediatric disease as it is permissive to infection with the viral and bacterial agents that cause OM in humans and by appropriate viral-bacterial co-infection, one can experimentally mimic the natural disease course of OM observed in the child. It has shown reproducibility in numerous preclinical trials wherein the efficacy of NTHi-targeted immunogens to prevent or resolve-induced OM was assessed and is shown to be predictive of a clinical trial outcome in examined in children. Moreover, the chinchilla also serves as a robust host that both we and others employ to study characteristics of bacterial biofilms associated with OM.

In the rigorous challenge model described herein, after a period of four days to permit NTHi to establish robust biofilms within the middle ear, animals were immunized via TCI. The administration of saline served as a negative control and provided the ability to examine the immune response elicited by application of dmLT alone. This adjuvant is a form of *E. coli* heat-labile enterotoxin wherein two amino acid substitutions inactivate a trypsin cleavage site and modifies a potential pepsin cleavage site, thus rendering the molecule nontoxic, while adjuvant properties are retained. DmLT promotes activation of various cell types, including DCs, with a resultant mixed Th1/Th2-type immune response.

Compared to delivery of saline, three days after primary TCI with dmLT alone, an initial reduction in clinically-relevant signs of OM, in addition to a significant decrease in CFU NTHi within middle ear mucosal biofilms was achieved. However, this was a transient outcome, as two days later no differences were observed between the two cohorts. This early response likely reflected nonspecific activation and function of dermal DCs. However, without a sustained antigenic stimulus, this response appeared temporary. In contrast, the formulation in which chimV4 was administered with dmLT induced a similar, yet, prolonged and effective outcome. Significant differences in clinically-relevant signs of OM, significant reduction in the amount of mucosal biofilms within the middle ear space and significantly fewer NTHi were present within the biofilms beginning three days after receipt of the first immunizing dose. As immunogen specific IgG and IgA was not detected within the middle ear until 5 days after primary ICI, these early effects represent activation of innate immune elements, i.e. dendritic cell activation, production of host defense peptides, cytokine/chemokine signaling. The observed greater efflux of dDCs from the pinnae and detection of a greater concentration of cBD1 support this. Thus, our data shows that dmLT played an early, critical role in immune activation that was further enhanced and focused against NTHi with the addition of chimV4 in the vaccine formulation.

Host defense peptides are multifunctional proteins that possess both antimicrobial and immunomodulatory characteristics. The 3-defensins are one class of host defense peptide and are shown to be produced by epithelial cells, constitutively or immediately in response to infection. Middle ear mucosal homogenates were tested for the presence of cBD-1, the orthologue to human 3-defensin 3, as a potential innate immune factor that contributed to the early reduction in signs of OM and concentration of NTHi within mucosal biofilms. A correlation between a greater concentration of cBD-1 and fewer NTHi was detected, particularly within the middle ears of animals that received dmLT alone or chimV4+ dmLT. It is also reported that exposure of neutrophils to human 3-defensin-3 suppresses apoptosis of these critical immune cells; moreover this molecule is chemotactic for neutrophils and macrophages. While these functions are not yet described for cBD-1, this molecule may possess similar functional characteristics, the result of which would be the elimination of NTHi from the middle ear, as observed.

Specific to the kinetics of disease resolution, the first seven days after primary TCI yielded the most dramatic resolution of disease, shown by multiple assessments. Via video otoscopy and tympanometry, delivery of chimV4+ dmLT resulted in a 90% reduction in the percentage of middle ears with OM within this cohort. Grossly, by day 7 the mean mucosal biofilm score for this cohort equaled 1.7, a 50-75% reduction relative to day 0. Moreover, a >5-log reduction in CFU NTHi was detected within mucosal biofilms collected from the middle ear. The only assessment that did not follow this trend was the examination of CFU NTHi within MEFs. No differences were detected among the cohorts until beginning on day 7, at which time the planktonic NTHi were rapidly eradicated. Interestingly, the time point for resolution of NTHi from MEFs correlated with the detection of chimV4-specific IgG in MEFs at a GMT of ≥160. As previously mentioned, a GMT of ≥160 is associated with resolution of experimental OM in this model.

Collectively, our data demonstrated two phases of disease resolution in this experimental model: an early phase from days 0 to 7 after primary TCI in which dmLT-induced activation of dermal DCs with subsequent migration to the NALT, secretion of cytokines and chemokines by activated DCs to stimulate expansion and polarization of $CD4^+$ T-cells and production of at least one of many host defense peptides known to have activity against NTHi, cBD-1. Inclusion of chimV4 within the formulation prolonged this response.

Phase two began 7 days after primary ICI, upon administration of the second immunizing dose as immunogen-specific antibody that targets determinants expressed by NTHi was now detected. While the timeframe proposed by this model incorporates the basic tenets for the initiation of innate and adaptive immune responses, this is the first report of a kinetic analysis of disease resolution after TCI that also incorporates challenge with a biological agent.

Example 2

Synthesis of Chimeric Proteins

The chimeric proteins of the presently described subject matter were produced using standard 15 recombinant methods. Initially, a gene-synthesis company, (Blue Heron Biotechnology Inc.) was contracted to make the initial plasmid based on the chimeric protein amino acid sequences described herein that were optimized for *E. coli* preferred codon usage. Briefly, the native NTHi pilin protein sequence was modified by truncating the N-terminus (residues 1-39 of SEQ ID NO: 2) and adding a HIS-tag sequence and a thrombin cleavage site as set out in SEQ ID NO: 3. The HIS-tag was preceded by a sequence (MUSS) to assist in expression. The thrombin cleavage site allowed for release of the HIS-tag. These plasmids were then cloned into the *E. coli* expression vector pET-15b vector (Novagen). The plasmid were then transformed into *E. coli* strain "Origami (DE3)" (available from Novagen) as the host for expression of soluble His-tagged chimeric proteins. Another *E. coli* host cell expression stain that may be used is Origami B(DE3) (Novagen).

The His-tagged variants of the chimeric proteins will be recovered by nickel column chromatography, then used for initial studies to determine if they are reactive with antisera directed against any of the following: native OMP P5-fimbrin, LB1 (full length 40 amino acid peptide), LB1(1) (a synthetic peptide representing just the 19 amino acid B-cell epitope of LB1), recombinant PilA protein or native PilA protein. Once the His-tag is removed by thrombin site cleavage, the recombinant huneric proteins will be used as immunogens to determine their immunogenicity and protective capability.

Exemplary chimeric proteins of the presently described subject matter have the sequences as set out in Table 2 below. The chimeric proteins having the amino acid sequences of SEQ ID NOS: 10, 12 and 14 have been expressed by *E. coli* as described above.

TABLE 2

| SEQ ID NO: | Chimeric Protein Amino Acid Sequence |
|---|---|
| 9 | MGSSHHHHHSSGLVPRGSHMTKKAAVSELLQASAPYKADVELCRSDYKFYEDANGTRDHKKGCTGGKNGIAADITTAKGYVKSVTSNGAITVKGDGTLANMEYILQATGNAATGVTWTTCKGTDASLFPANFCGSVTQ |
| 10 | MGSSHHHHHSSGLVPRGSHMTKKAAVSELLQASAPYKADVELCLVRSDYKFYEDANGTRDHKKGHTCTGGKNGIAADITTAKGYVKSVTTSNGAITVKGDGTLANMEYILQATGNAATGVTWTTCKGTDASLFPANFCGSVTQ |
| 11 | MGSSHHHHHSSGLVPRGSHMTKKAAVSELLQASAPYKADVELCVTSTNETTNCTGGKNGIAADITTAKGYVKSVTTSNGAITVKGDGTLANMEYILQATGNAATGVTWTTCRSDYKFYEDANGTRDHKKGCGSVTQ |
| 12 | MGSSHHHHHSSGLVPRGSHMTKKAAVSELLQASAPYKADVELCVTSTNETTNCTGGKNGIAADITTAKGYVKSVTTSNGAITVKGDGTLANMEYILQATGNAATGVTWTTCLVRSDYKFYEDANGTRDHKKGRHTCGSVTQ |
| 13 | MGSSHHHHHSSGLVPRGSHMTKKAAVSELLQASAPYKADVELCVTSTNETTNCTGGKNGIAADITTAKGYVKSVTTSNGAITVKGDGTLANMEYILQATGNAATGVTWTTCKGTDASLFPANFCGSVTQRSDYKFYEDANGTRDHKK |
| 14 | MGSSHHHHHSSGLVPRGSHMTKKAAVSELLQASAPYKADVELCVTSTNETTNCTGGKNGIAADITTAKGYVKSVTTSNGAITVKGDGTLANMEYILQATGNAATGVTWTTCKGTDASLFPANFCGSVTQLVRSDYKFYEDANGTRDHKKGRHT |
| 15 | MGSSHHHHHSSGLVPRGSHMTKKAAVSELLQASAPYKADVELCRSDYKLYNKNSSSNSTLKNLGECTGGKNGIAADITTAKGYVKSVTTSNGAITVKGDGTLANMEYILQATGNAATGVTWTTCKGTDASLFPANFCGSVTQ |
| 16 | MGSSHHHHHSSGLVPRGSHMTKKAAVSELLQASAPYKADVELCLVRSDYKLYNKNSSSNSTLKNLGERHTCTGGKNGIAADITTAKGYVKSVITSNGAITVKGDGTLANMEYILQATGNAATGVTWTTCKGTDASLFPANFCGSVTQ |
| 17 | MGSSHHHHHSSGLVPRGSHMTKKAAVSELLQASAPYKADVELCVTSTNETTNCTGGKNGIAADITTAKGYVKSVTTSNGAITVKGDGTLANMEYTLQATGNAATGVTWTTCRSDYKLYNKNSSSNSTLKNLGECGSVTQ |
| 18 | MGSSHHHHHSSGLVPRGSHMTKKAAVSELLQASAPYKADVELCVTSTNETTNCTGGKNGIAADITTAKGYVKSVTTSNGAITVKGDGTLANMEYILQATGNAATGVTWTTCLVRSDYKLYNKNSSSNSTLKNLGERHTCGSVTQ |
| 19 | MGSSHHHHHSSGLVPRGSHMTKKAAVSELLQASAPYKADVELCVTSTNETTNCTGGKNGIAADITTAKGYVKSVTTSNGAITVKGDGTLANMEYILQATGNAATGVTWTTCKGTDASLFPANFCGSVTQRSDYKLYNKNSSSNSTLKNLGE |
| 20 | MGSSHHHHHSSGLVPRGSHMTKKAAVSELLQASAPYKADVELCVTSTNETTNCTGGKNGIAADITTAKGYVKSVTTSNGAITVKGDGTLANMEYILQATGNAATGVTWTTCKGTDASLFPANFCGSVTQLVRSDYKLYNKNSSSNSTLKNLGERHT |
| 21 | MGSSHHHHHSSGLVPRGSHMTKKAAVSELLQASAPYKADVELCRSDYKLYNKNSSSLKNLGECTGGKNGIAADITTAKGYVKSVTTSNGAITVKGDGTLANMEYILQATGNAATGVTWTTCKGTDASLFPANFCGSVTQ |
| 22 | MGSSHHHHHSSGLVPRGSHMTKKAAVSELLQASAPYKADVELCLVRSDYKLYNKNSSTLKNLGERHTCTGGKNGIAADITTAKGYVKSVTTSNGAITVKGDGTLANMEYILQATGNAATGVTWTTCKGTDASLFPANFCGSVTQ |
| 23 | MGSSHHHHHSSGLVPRGSHMTKKAAVSELLQASAPYKADVELVTSTNETTNCTGGKNGIAADITTAKGYVKSVTTSNGAITVKGDGTLANMEYILQATGNAATGVTWTTCRSDYKLYNKNSSTLKNLGECGSVTQ |
| 24 | MGSSHHHHHSSGLVPRGSHMTKKAAVSELLQASAPYKADVELCVTSTNETTNCTGGKNGIAADITTAKGYVKSVTTSNGAITVKGDGTLANMEYILQATGNAATGVTWTTCLVRSDYKLYNKNSSTLKNLGERHTCGSVTQ |
| 25 | MGSSHHHHHSSGLVPRGSHMTKKAAVSELLQASAPYKADVELCVTSTNETTNCTGGKNGIAADITTAKGYVKSVTTSNGAITVKGDGTLANMEYILQATGNAATGVTWTTCKGTDASLFPANFCGSVTQRSDYKLYNKNSSTLKNLGE |
| 26 | MGSSHHHHHSSGLVPRGSHMTKKAAVSELLQASAPYKADVELCVTSTNETTNCTGGKNGIAADITTAKGYVKSVTTSNGAITVKGDGTLANMEYILQATGNAATGVTWTTCKGTDASLFPANFCGSVTQLVRSDYKLYNKNSSTLKNLGERHT |
| 27 | MGSSHHHHHSSGLVPRGSHMTKKAAVSELLQASAPYKADVELCRSDYKFYDNKRIDCTGGKNGIAADITTAKGYVKSVTTSNGAITVKGDGTLANMEYILQATGNAATGVTWTTCKGTDASLFPANFCGSVTQ |
| 28 | MGSSHHHHHSSGLVPRGSHMTKKAAVSELLQASAPYKADVELCLVRSDYKFYDNKRIDRHTCTGGKNGIAADITTAKGYVKSVTTSNGAITVKGDGTLANMEYILQATGNAATGVTWTTCKGTDASLFPANFCGSVTQ |
| 29 | MGSSHHHHHSSGLVPRGSHMTKKAAVSELLQASAPYKADVELCVTSTNETTNCTGGKNGIAADITTAKGYVKSVTTSNGAITVKGDGTLANMEYILQATGNAATGVTWTTCRSDYKFYDNKRIDCGSVTQ |
| 30 | MGSSHHHHHSSGLVPRGSHMTKKAAVSELLQASAPYKADVELCVTSTNETTNCTGGKNGIAADITTAKGYVKSVTTSNGAITVKGDGTLANMEYILQATGNAATGVTWTTCLVRSDYKFYDNKRIDRHTCGSVTQ |
| 31 | MGSSHHHHHSSGLVPRGSHMTKKAAVSELLQASAPYKADVELCVTSTNETTNCTGGKNGIAADITTAKGYVKSVTTSNGAITVKGDGTLANMEYILQATGNAATGVTWTTCKGTDASLFPANFCGSVTQRSDYKFYDNKRID |
| 32 | MGSSHHHHHSSGLVPRGSHMTKKAAVSELLQASAPYKADVELCVTSTNETTNCTGGKNGIAADITTAKGYVKSVTTSNGAITVKGDGTLANMEYILQATGNAATGVTWTTCKGTDASLFPANFCGSVTQLVRSDYKFYDNKRIDRHT |

Additional exemplary chimeric proteins of the presently described subject matter have the amino acid sequences as set forth in Table 3 below. These chimeric proteins have been expressed by *E. coli* and purified using a HIS-tag, as described above. The chimeric proteins set out in Table 3 have the His tag sequence removed for use as an immunogen. The chimeric protein having the amino acid sequence of SEQ ID NO: 56 was used in the studies described in Example 5.

TABLE 3

| SEQ ID NO: | Chimeric Protein Amino Acid Sequence |
|---|---|
| 54 | GSHMTKKAAVSELLQASAPYKADVELCLVRSDYKFYEDANGT RDHKKGRHTCTGGKNGIAADITTAKGYVKSVTTSNGAITVKGD GTLANMEYILQATGNAATGVTWTTTCKGTDASLFPANFCGSV TQ |
| 55 | GSHMTKKAAVSELLQASAPYKADVELCVYSTNETTNCTGGKN GIAADITTAKGYVKSVTTSNGAITVKGDGTLANMEYILQATGNA ATGVTWTTTCLVRSDYKFYEDANGTRDHKKGRHTCGSVTQ |
| 56 | GSHMTKKAAVSELLQASAPYKADVELCVYSTNETTNCTGGKN GIAADITTAKGYVKSVTTSNGAITVKGDGTLANMEYILQATGNA ATGVTWTTTCKGTDASLFPANFCGSVTQLVRSDYKFYEDAN GTRDHKKGRHT |

TABLE 3-continued

| SEQ ID NO: | Chimeric Protein Amino Acid Sequence |
|---|---|
| 57 | GSHMLVRSDYKFYEDANGTRDHKKGRHTGPSLKLTKKAAVS ELLQASAPYKADVELCVYSTNETTNCTGGKNGIAADITTAKGY VKSVTTSNGAITVKGDGTLANMEYILQATGNAATGVTWTTTC KGTDASLFPANFCGSVTQ |

All publications cited in the specification are indicative of the level of skill of those skilled in the art to which the presently described subject matter pertains. All of these publications are hereby incorporated by reference herein to the same extent as if each individual publication were specifically and individually indicated as being incorporated by reference.

The present subject matter being thus described, it will be apparent that the same may be modified or varied in many ways. Such modifications and variations are not to be regarded as a departure from the spirit and scope of the present subject matter, and all such modifications and variations are intended to be included within the scope of the following claims.

What is claimed:

1. A topical delivery system, comprising:
a topical immunogenic composition comprising a therapeutically effective amount of a pharmaceutical composition comprising at least one *Haemophilus influenzae* vaccine agent and a pharmaceutically acceptable topical carrier and/or adjuvant and
a flexible substrate in communication with the topical immunogenic composition, wherein the flexible substrate is a bandage, cotton pad, gauze pad, poultice, tape or skin patch, and
wherein the topical delivery system is configured for application to the intact surface of the skin of a subject at a location in the post-auricular region of the subject.

2. The topical delivery system according to claim 1, wherein the topical immunogenic composition comprises at least one adjuvant comprising a mucosal adjuvant.

3. The topical delivery system according to claim 2, wherein the mucosal adjuvant is dmLT.

4. The topical delivery system according to claim 1, wherein the flexible substrate comprises a skin-contacting surface.

5. The topical delivery system according to claim 4, wherein the flexible substrate comprises the topical pharmaceutical composition.

6. The topical delivery system according to claim 4, wherein the topical immunogenic composition is provided on the skin-contacting surface.

7. The topical delivery system according to claim 1, wherein the flexible substrate comprises an backing having a lower surface and at least one active agent containing layer comprising the at least one active agent or the topical immunogenic composition, the active agent containing layer having a skin-contacting surface, the active agent containing layer provided on the lower surface of the backing such that during use the skin-contacting surface is in contact with a skin surface of a subject.

8. The topical delivery system according to claim 7, wherein the at least one active agent containing layer comprises a polymeric matrix layer.

9. The topical delivery system according to claim 8, wherein the active agent or the topical immunogenic composition is dispersed or suspended in the polymeric matrix layer.

10. The topical delivery system according to claim 8, wherein the polymeric matrix layer is a pressure-sensitive adhesive matrix layer.

11. The topical delivery system according to claim 10, wherein the wherein the active agent or the topical immunogenic composition is dispersed or suspended in the pressure-sensitive adhesive matrix layer.

12. The topical delivery system according to claim 8, wherein the polymeric matrix layer releases the active agent at a predetermined controlled rate.

13. The topical delivery system according to claim 8, wherein the polymeric matrix layer comprises one or more biodegradable or bioerodable polymers.

14. The topical delivery system according to claim 7, wherein the backing is an adhesive backing or an occlusive adhesive backing.

15. The topical delivery system according to claim 7, wherein the backing is an occlusive backing.

16. The topical delivery system according to claim 1, wherein the post-auricular region does not comprise any portion of the subject's pinnae.

17. The topical delivery system according to claim 16, wherein the subject is a pediatric subject.

* * * * *

UNITED STATES PATENT AND TRADEMARK OFFICE
CERTIFICATE OF CORRECTION

PATENT NO.        : 10,722,568 B2
APPLICATION NO.   : 15/824387
DATED             : July 28, 2020
INVENTOR(S)       : Lauren O. Bakaletz Page 1 of 1

It is certified that error appears in the above-identified patent and that said Letters Patent is hereby corrected as shown below:

On the Title Page

At item (54), Line 1, "Haemophilius" should be --Haemophilus--.

In the Claims

At Column 89, Line 42, replace "adjuvant and" with --adjuvant, and--.

At Column 89, Line 65, replace "an backing" with --a backing--.

At Column 90, Line 51, replace "wherein the wherein the active" with --wherein the active--.

Signed and Sealed this
First Day of June, 2021

Drew Hirshfeld
*Performing the Functions and Duties of the*
*Under Secretary of Commerce for Intellectual Property and*
*Director of the United States Patent and Trademark Office*